United States Patent [19]

Dumas et al.

[11] Patent Number: 4,752,322

[45] Date of Patent: Jun. 21, 1988

[54] HERBICIDAL SULFONAMIDES

[76] Inventors: Donald J. Dumas, 407 Baynard Blvd., Wilmington, Del. 19803; Marcus P. Moon, 1703 N. Union St., Wilmington, Del. 19806

[21] Appl. No.: 926,732

[22] Filed: Nov. 4, 1986

Related U.S. Application Data

[63] Continuation-in-part of Ser. No. 845,703, Apr. 2, 1986, abandoned, which is a continuation-in-part of Ser. No. 733,906, May 14, 1985, abandoned.

[51] Int. Cl.⁴ .................. C07D 239/69; C07D 401/12; C07D 409/12; A01N 43/54
[52] U.S. Cl. ............................................ 71/90; 71/91; 71/92; 71/87; 544/243; 544/229; 544/321; 544/323; 544/324; 544/331; 544/332; 544/122; 544/123
[58] Field of Search .................. 71/90, 91, 92, 87; 544/243, 229, 321, 323, 324, 331, 332, 122, 123

[56] References Cited

U.S. PATENT DOCUMENTS

| | | | |
|---|---|---|---|
| 4,369,320 | 1/1983 | Levitt et al. | 544/320 |
| 4,370,479 | 1/1983 | Levitt | 544/278 |
| 4,465,506 | 8/1984 | Welch | 71/92 |
| 4,492,596 | 1/1985 | Pasteris | 71/92 |
| 4,514,211 | 4/1985 | Rorer | 71/92 |
| 4,589,911 | 5/1986 | Ehrenfreund et al. | 71/91 |
| 4,634,465 | 1/1987 | Ehrenfreund et al. | 71/92 |

FOREIGN PATENT DOCUMENTS

| | | |
|---|---|---|
| 123303 | 10/1984 | European Pat. Off. . |
| 835165 | 1/1984 | South Africa . |
| 843522 | 11/1984 | South Africa . |

*Primary Examiner*—John M. Ford
*Attorney, Agent, or Firm*—Theodore C. Gregory

[57] ABSTRACT

This invention relates to herbicidally active sulfonylurea compounds, agriculturally suitable compositions thereof and their method of use as herbicides or plant growth regulants.

30 Claims, No Drawings

HERBICIDAL SULFONAMIDES

RELATED APPLICATION

This application is a continuation-in-part of application U.S. Ser. No. 845,703, filed Apr. 2, 1986 which is a continuation-in-part of U.S. Ser. No. 733,906 filed May 14, 1985, both now abandoned.

BACKGROUND OF THE INVENTION

This invention relates to herbicidally active sulfonylurea compounds, agriculturally suitable compositions containing such compounds and a method of their use as herbicides or plant growth regulants.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around fuel storage tanks, ammunition depots and industrial storage areas. There are many products commercially available for these purposes, but the search continues for products which are more effective, less costly and environmentally safe.

Even though there are sulfonylurea herbicides which exhibit excellent selectivity on a number of crops while controlling weeds at very low application rates there continues to be a need for herbicides that display such selectivity while controlling weeds.

U.S. Pat. No. 4,514,211 discloses herbicidal sulfonamides of formula wherein
L is $$\overset{W}{\underset{R_{12}}{\overset{\|}{SO_2NHCNA}}};$$

$R_1$ is H or $C_1$–$C_4$ alkyl;
$R_2$ is H or $C_1$–$CH_4$ alkyl;
$R_3$ is H or $CH_3$;
$R_4$ is H, Cl, $CH_3$, $CF_3$, $OCH_3$, Br, F, $SCH_3$ or $OCF_2H$;
$R_5$ is H, $CH_3$, $OCH_3$, Cl, Br, $NO_2$, $CO_2R_7$, $SO_2R_8$, $OSO_2R_9$, $SO_2NR_{10}R_{11}$, F, $CF_3$, $SCH_3$, $OCF_2H$ or $SO_2N(OCH_3)CH_3$; and
Q is O, S, SO or $SO_2$.

U.S. Pat. No. 4,492,596 discloses, in part, herbicidal sulfonamides of formula wherein
Q is O, S or $SO_2$;
R is H or $CH_3$;
$R_1$ is H, $CH_3$, $OCH_3$, Cl, Br, $CO_2R_5$, $SO_2R_6$, $OSO_2R_7$ or $SO_2NR_8R_9$;
$R_2$ and $R_3$ are independently H or $C_1$–$CH_3$ alkyl; and
$R_4$ is H or $CH_3$.

U.S. Pat. No. 4,370,479 discloses herbicidal sulfonamides of formula wherein
$A^1$ is H, F, Cl, Br, $CH_3O$ or $NO_2$;
A and $A^2$ are independently $C(O)QR^8$, $C(T)R^9$, Cl, F, Br, $NO_2$, $CH_3$, $SO_2NR^1R^2$, $SO_2N(CH_3)(OCH_3)$, $S(O)_nR^3$, $OR^3$, $OSO_2R^3$ Or $OSO_2CF_3$;
B is $SO_2NHC(W)NR^4R^5$ or $SO_2N=C(WR^6)NHR^5$.

U.S. Pat. No. 4,465,506 discloses, in part, herbicidal sulfonamides of formula wherein
L is $SO_2NHC(O)NR_{10}R_1$;
R is H, Cl, Br, $NO_2$, $QR_2$, $CO_2R_3$, $SO_2NR_5R_6$, $SO_2N(OCH_3)CH_3$, $OSO_2R_7$ or $C_1$–$C_3$ alkyl;
$R_8$ is H, $CH_3$ or Cl; and
$R_9$ is H or $CH_3$.

U.S. Pat. No. 4,369,320 discloses, in part, herbicidal sulfonamides of formula wherein
A is $$SO_2NHC(W)NH-\!\!\!\!\!\!\!\!\!\!\!\!\bigcirc\!\!\!\!\!\!\!\!\!\!\!\!\begin{array}{c} N\overset{X}{\diagup} \\ Z \text{ or} \\ N\overset{\diagdown}{Y} \end{array}$$

-continued

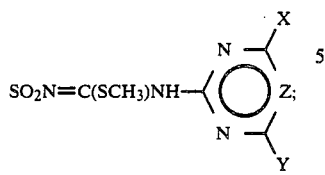

and

R₁ is H, F, Cl, Br, OCH₃, CH₃, NO₂, CO₂R₂, S(O)$_n$R₃, SO₂NR₄R₅, SO₂N(OCH₃)CH₃ or OSO₂R₆.

No. EP-A-107,979 (published May 9, 1984) discloses herbicidal sulfonamides of formula

wherein
J is, in part,

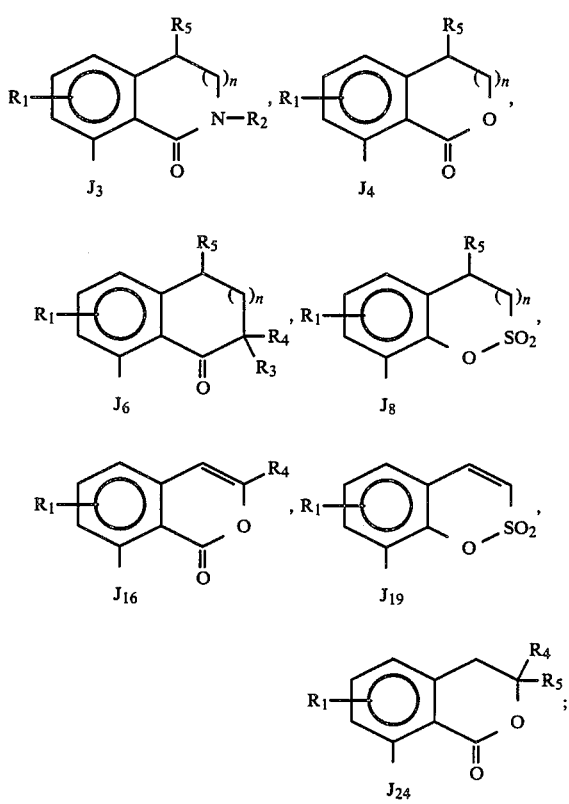

R₁ is H, F, Cl, Br, CH₃, OCH₃, CF₃, SCH₃ or OCF₂H;
R₂ is H or CH₁-C₄ alkyl;
R₃ and R₄ are independently H, C₁-C₄ alkyl, Cl or Br; and
R₅ is H or CH₃.

South African Patent Application No. 83/5165, published Jan. 16, 1984, discloses herbicidal sulfonylureas of the general structure shown below:

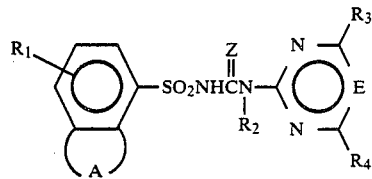

wherein
A is an unsubstituted or substituted bridge of 3 or 4 atoms which contains 1 or 2 oxygen, sulfur or nitrogen atoms and, together with the linking carbon atom, forms a non-aromatic 5- or 6-membered heterocyclic ring system, with the proviso that two oxygen atoms are separated by at least one carbon atom and that oxygen and sulfur atoms are only linked to each other if the sulfur atom takes the form of the —SO— or SO₂— group; and
R₁ is H, halogen, NO₂, C₁-C₄ alkyl, C₁-C₄ haloalkyl, C₁-C₄ alkoxy, C₁-C₄ haloalkoxy, C₁-C₄ alkoxycarbonyl, C₁-C₄ alkylthio, C₁-C₄ alkylsulfinyl, C₁-C₄ alkylsulfonyl or C₂-C₅ alkoxyalkoxy.

No. EP-A-123,303 (published Oct. 31, 1984) discloses herbicidal sulfonamides of formula

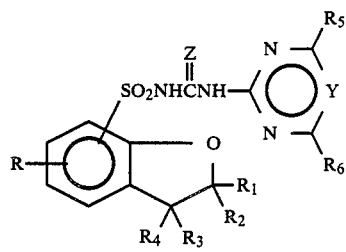

wherein
R is H, halogen, CH₃, NO₂, alkoxycarbonyl, alkylsulphonyl, aminocarbonyl, mono- or dialkylaminocarbonyl, alkoxy (optionally substituted by 1-3 halogen), alkynyloxy, aryloxy or NR₇COR₈;
R₁, R₂, R₃ and R₄ are H or CH₃; or CR₁R₂ and CR₃R₄ are C=O.

South African Patent Application No. 84/3522 (published Nov. 11, 1984) discloses herbicidal sulfonamides of formula

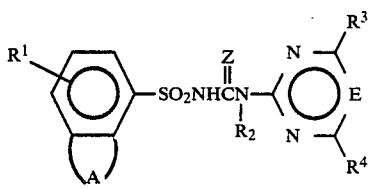

wherein
R₁ is H, halogen, NO₂, C₁-C₄ alkyl, C₁-C₄ haloalkyl, CN, XR⁵, COXR⁶, CONR⁷R⁸, SOR⁹ or SO₂R¹⁰;
A is an unsubstituted or substituted unsaturated bridge of 4 atoms, of the formula —CH=CH—Y—, wherein Y is a bridge member of 2 atoms which is selected from the series consisting of —NH—CO—, —NH—SO₂—, —S—CO—, —S—SO₂—, —O—CO— or —O—SO₂—.

A part of this disclosure is carried by U.S. Pat. No. 4,589,911, issued May 20, 1986.

SUMMARY OF THE INVENTION

Novel compounds have been found of the formula

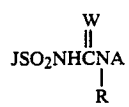

I wherein
J is

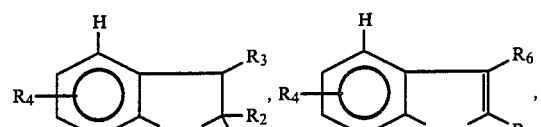

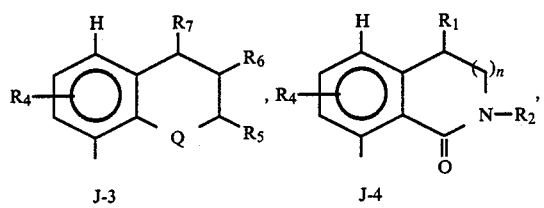

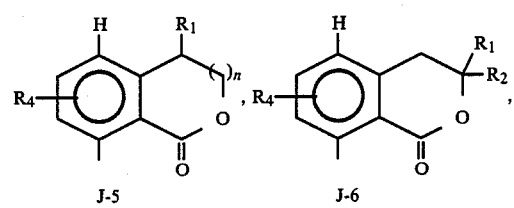

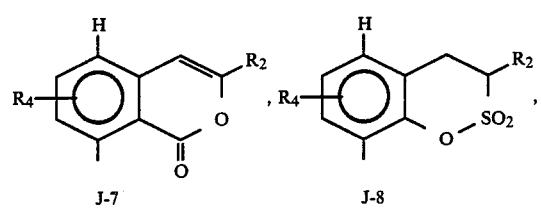

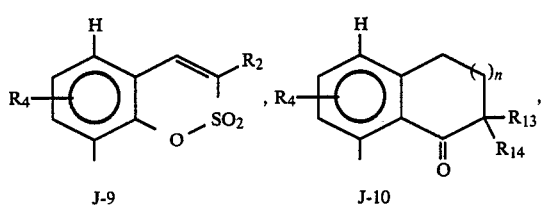

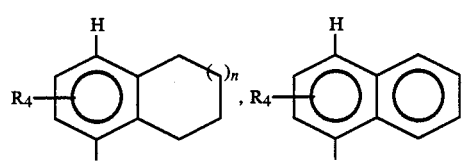

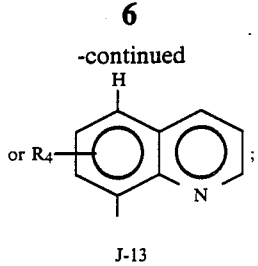

n is 0 or 1;
W is O or S;
Q is O, S, SO or $SO_2$;
R is H or $CH_3$;
$R_1$ is H or $CH_3$;
$R_2$ is H or $C_1$–$C_3$ alkyl;
$R_3$ is H or $CH_3$;
$R_4$ is $C_3$–$C_6$ cycloalkyl, $C_5$–$C_6$ cycloalkenyl,

$Si(CH_3)_2(C_1$–$C_4$ alkyl), $Si(CH_3)_2(C_2$–$C_4$ alkenyl), $Si(CH_3)_2(C_1$–$C_3$ alkoxy),

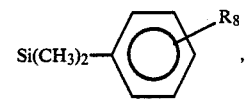

$P(O)(CH_3)_2$, $P(O)(OCH_3)_2$, CN, $C_1$–$C_4$ alkylcarbonyl, $C_3$–$C_4$ cycloalkylcarbonyl, $NR_9R_{10}$ or $C_1$–$C_2$ alkyl substituted with $C_3$–$C_5$ cycloalkyl, $C_1$–$C_3$ alkoxy, $C_1$–$C_3$ haloalkoxy, $C_2$–$C_3$ alkenyloxy, $C_2$–$C_3$ haloalkenyloxy, $C_1$–$C_3$ alkylthio, $C_1$–$C_3$ haloalkylthio, $C_1$–$C_3$ alkylsulfinyl, $C_1$–$C_3$ alkylsulfonyl, $C_1$–$C_3$ haloalkylsulfinyl, $C_1$–$C_3$ haloalkylsulfonyl, $Si(CH_3)_2(C_1$–$C_4$ alkyl), $NO_2$, CN, $C_1$–$C_2$ alkylcarbonyl, OH, $NR_9R_{10}$, $CO_2(C_1$–$C_3$ alkyl), SCN, $P(O)(OCH_3)_2$ or $SO_2NR_{11}R_{12}$;
$R_5$ is H or $C_1$–$C_2$ alkyl;
$R_6$ is H or $CH_3$;
$R_7$ is H or $CH_3$;
$R_8$ is H, F, Cl, Br, $CH_3$, $OCH_3$ or $SCH_3$;
$R_9$ is H or $C_1$–$C_3$ alkyl;
$R_{10}$ is H or $C_1$–$C_3$ alkyl; or
$R_9$ and $R_{10}$ may be taken together to form $(CH_2)_4$, $(CH_2)_5$ or $CH_2CH_2OCH_2CH_2$;
$R_{11}$ and $R_{12}$ are independently H or $C_1$–$C_3$ alkyl;
$R_{13}$ is H, $C_1$–$C_3$ alkyl, Cl or Br;
$R_{14}$ is H, $CH_3$, Cl or Br;
A is

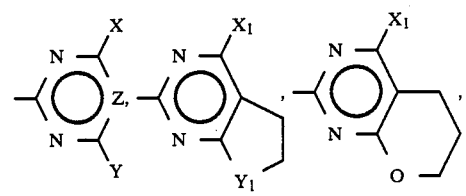

-continued

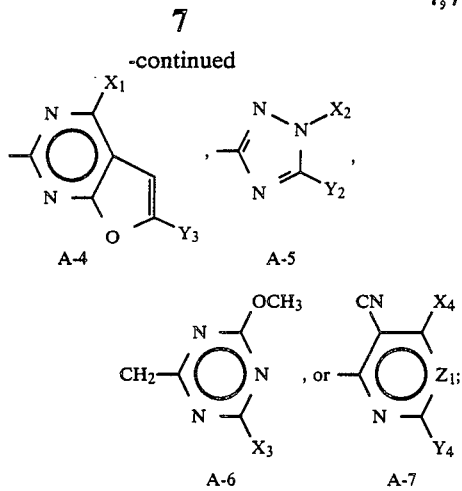

X is H, $C_1-C_4$ alkyl, $C_1-C_4$ alkoxy, $C_1-C_4$ haloalkoxy, $C_1-C_4$ haloalkyl, $C_1-C_4$ haloalkylthio, $C_1-C_4$ alkylthio, halogen, $C_2-C_5$ alkoxyalkyl, $C_2-C_5$ alkoxyalkoxy, amino, $C_1-C_3$ alkylamino, di($C_1-C_3$ alkyl)amino or $C_3-C_5$ cycloalkyl;

Y is H, $C_1-C_4$ alkyl, $C_1-C_4$ alkoxy, $C_1-C_4$ haloalkoxy, $C_1-C_4$ haloalkylthio, $C_1-C_4$ alkylthio, $C_2-C_5$ alkoxyalkyl, $C_2-C_5$ alkoxyalkoxy, amino, $C_1-C_3$ alkylamino, di($C_1-C_3$ alkyl)amino, $C_3-C_4$ alkenyloxy, $C_3-C_4$ alkynyloxy, $C_2-C_5$ alkylthioalkyl, $C_2-C_5$ alkylsulfinylalkyl, $C_2-C_5$ alkylsulfonylalkyl, $C_1-C_4$ haloalkyl, $C_2-C_4$ alkynyl, azido, cyano,

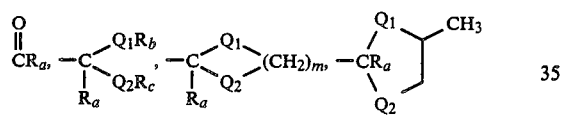

or $N(OCH_3)CH_3$;

m is 2 or 3;
$Q_1$ and $Q_2$ are independently O or S;
$R_a$ is H or $C_1-C_3$ alkyl;
$R_b$ and $R_c$ are independently $C_1-C_3$ alkyl;
Z is CH, N, $CCH_3$, $CC_2H_5$, CCl or CBr;
$Y_1$ is O or $CH_2$;
$X_1$ is $CH_3$, $OCH_3$, $OC_2H_5$ or $OCF_2H$;
$X_2$ is $CH_3$, $C_2H_5$ or $CH_2CF_3$;
$Y_2$ is $OCH_3$, $OC_2H_5$, $SCH_3$, $SC_2H_5$, $CH_3$ or $CH_2CH_3$;
$X_3$ is $CH_3$ or $OCH_3$;
$Y_3$ is H or $CH_3$;
$X_4$ is $CH_3$, $OCH_3$, $OC_2H_5$, $CH_2OCH_3$ or Cl;
$Y_4$ is $CH_3$, $OCH_3$, $OC_2H_5$ or Cl; and
$Z_1$ is CH or N;
and their agriculturally suitable salts; provided that
(a) when X is Cl, F, Br or I, then Z is CH and Y is $OCH_3$, $OC_2H_5$, $N(OCH_3)CH_3$, $NHCH_3$, $N(CH_3)_2$ or $OCF_2H$; and
(b) when X or Y is $C_1$ haloalkoxy, then Z is CH;
(c) when W is S, then R is H, A is A-1, Z is CH or N, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2C-H_2OCH_3$, $CH(OCH_3)_2$ or

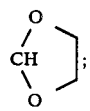

(d) when $R_1$ is $CH_3$, then n is 0;
(e) when J is J-6, then $R_1$ and $R_2$ are not both H;
(f) when the total number of carbons of X and Y is greater than four, then the number of carbons of $R_4$ must be less than or equal to three;
(g) $X_4$ and $Y_4$ may not simultaneously be Cl;
(h) when J is J-12, then $R_4$ is other than $C_1-C_4$ alkylcarbonyl; and
(i) when J is J-9, then $R_4$ is other than CN.

An embodiment of the invention are compounds of Formula I as defined above wherein:
J is J-1, J-2 or J-3;
$R_2$ is H or $CH_1-C_2$ alkyl;
$R_4$ is $C_3-C_6$ cycloalkyl, $C_5-C_6$ cycloalkenyl,

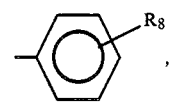

$Si(CH_3)_2(C_1-C_4$ alkyl), $Si(CH_3)_2(C_2-C_4$ alkenyl), $Si(CH_3)_2(C_1-C_3$ alkoxy),

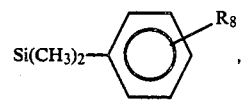

$P(O)(CH_3)_2$, $P(O)(OCH_3)_2$, $NR_8R_9$ or $C_1-C_2$ alkyl substituted with $C_3-C_5$ cycloalkyl, $C_1-C_3$ alkoxy, $C_1-C_3$ haloalkoxy, $C_2-C_3$ alkenyloxy, $C_2-C_3$ haloalkenyloxy, $C_1-C_3$ alkylthio, $C_1-C_3$ haloalkylthio, $C_1-C_3$ alkylsulfinyl, $C_1-C_3$ alkylsulfonyl, $C_1-C_3$ haloalkylsulfinyl, $C_1-C_3$ haloalkylsulfonyl, $Si(CH_3)_2(C_1-C_4$ alkyl), $NO_2$, CN, $CO_2(C_1-C_3$ alkyl), SCN, $P(O)(OCH_3)_2$ or $SO_2NR_{10}R_{11}$;

A is

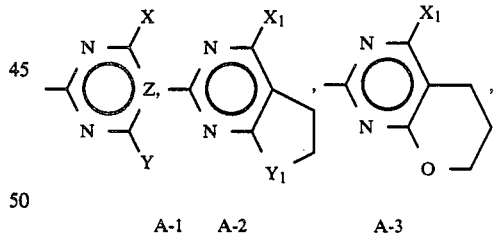

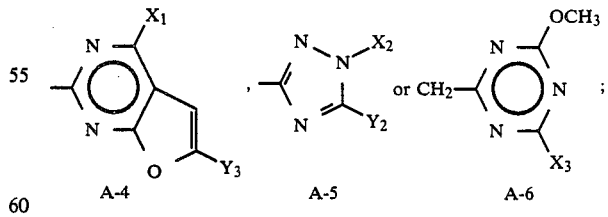

Y is H, $C_1-C_4$ alkyl, $C_1-C_4$ alkoxy, $C_1-C_4$ haloalkoxy, $C_1-C_4$ haloalkylthio, $C_1-C_4$ alkylthio, halogen, $C_2-C_5$ alkoxyalkyl, $C_2-C_5$ alkoxyalkoxy, amino, $C_1-C_3$ alkylamino, di($C_1-C_3$ alkyl)amino, $C_3-C_4$ alkenyloxy, $C_3-C_4$ alkynyloxy, $C_2-C_5$ alkylthioalkyl, $C_1-C_4$ haloalkyl, $C_2-C_4$ alkynyl, azido, cyano,

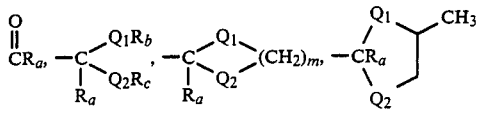

or N(OCH$_3$)CH$_3$;
provided that
(a) when X is Cl, F, Br or I, then Z is CH and Y is OCH$_3$, OC$_2$H$_5$, N(OCH$_3$)CH$_3$, NHCH$_3$, N(CH$_3$)$_2$ or OCF$_2$H; and
(b) when X or Y is OCF$_2$H, then Z is CH.

Compounds preferred for reasons relating to priority are compounds of Formula I wherein
J is J-1, J-2, J-3, J-4, J-5 or J-6;
R$_4$ is C$_3$-C$_6$ cycloalkyl, C$_5$-C$_6$ cycloalkenyl,

Si(CH$_3$)$_2$(C$_1$-C$_4$ alkyl), Si(CH$_3$)$_2$(C$_2$-C$_4$ alkenyl), Si(CH$_3$)$_2$(C$_1$-C$_3$ alkoxy),

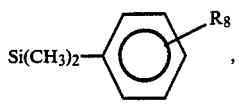

P(O)(CH$_3$)$_2$, P(O)(OCH$_3$)$_2$, CN, NR$_9$R$_{10}$ or C$_1$-C$_2$ alkyl substituted with C$_3$-C$_5$ cycloalkyl, C$_1$-C$_3$ alkoxy, C$_1$-C$_3$ haloalkoxy, C$_2$-C$_3$ alkenyloxy, C$_2$-C$_3$ haloalkenyloxy, C$_1$-C$_3$ alkylthio, C$_1$-C$_3$ haloalkylthio, C$_1$-C$_3$ alkylsulfinyl, C$_1$-C$_3$ alkylsulfonyl, C$_1$-C$_3$ haloalkylsulfinyl, C$_1$-C$_3$ haloalkylsulfonyl, Si(CH$_3$)$_2$(C$_1$-C$_4$ alkyl), NO$_2$, CN, NR$_9$R$_{10}$, CO$_2$(C$_1$-C$_3$ alkyl), SCN, P(O)(OCH$_3$)$_2$ or SO$_2$NR$_{11}$R$_{12}$; and
Y is H, C$_1$-C$_4$ alkyl, C$_1$-C$_4$ alkoxy, C$_1$-C$_4$ haloalkoxy, C$_1$-C$_4$ haloalkylthio, C$_1$-C$_4$ alkylthio, halogen, C$_2$-C$_5$ alkoxyalkykl, C$_2$-C$_5$ alkoxyalkoxy, amino, C$_1$-C$_3$ alkylamino, C$_2$-C$_5$ alkylsufinylalkyl, di(C$_1$-C$_3$ alkyl)amino, C$_3$-C$_4$ alkenyloxy, C$_3$-C$_4$ alkynyloxy, C$_2$-C$_5$ alkylthioalkyl, C$_2$-C$_5$ alkylsulfonylalkyl, C$_1$-C$_4$ haloalkyl, C$_2$-C$_4$ alkynyl, azido, cyano,

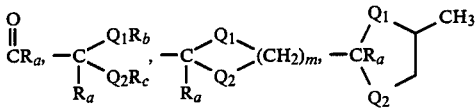

or N(OCH$_3$)CH$_3$;
under the provisos (a) through (f) except that in proviso (b), Z is CH when X or Y is OCF$_2$H.

In the above definitions, the term "alkyl", used either alone or in compound words such as "alkylthio" or "haloalkyl", denotes straight chain or branched alkyl, e.g. methyl, ethyl, n-propyl, isopropyl or the different butyl isomers.

Alkoxy denotes methoxy, ethoxy, n-propyloxy, isopropyloxy and the different butyl isomers.

Alkenyl denotes straight chain or branched alkenes, e.g. vinyl, 1-propenyl, 2-propenyl, 3-propenyl and the different butenyl isomers.

Alkynyl denotes straight chain or branched alkynes, e.g. ethynyl, 1-propynyl, 2-propynyl and the different butynyl isomers.

Alkylsulfonyl denotes methylsulfonyl, ethylsulfonyl and the different propylsulfonyl and butylsulfonyl isomers.

Alkylthio, alkylsulfinyl, alkylamino, etc. are defined analogously to the above examples.

Cycloalkyl denotes cyclopropyl, cyclobutyl, cyclopentyl and cyclohexyl.

The term "halogen", either alone or in compound words such as "haloalkyl", denotes fluorine, chlorine, bromine or iodine. Further, when used in compound words such as "haloalkyl" said alkyl may be partially halogenated or fully substituted with halogen atoms and said halogen atoms may be the same or different. Examples of haloalkyl include CH$_2$CH$_2$F, CF$_2$CF$_3$ and CH$_2$CHFCl.

The total number of carbon atoms in a substituent group is indicated by the C$_i$-C$_j$ prefix where i and j are numbers from 1 to 6. For example, C$_1$-C$_3$ alkylsulfonyl would designate methylsulfonyl through propylsulfonyl, C$_2$ alkoxyalkoxy would designate OCH$_2$OCH$_3$, C$_2$ cyanoalkyl would designate CH$_2$CN and C$_3$ cyanoalkyl would designate CH$_2$CH$_2$CN and CH(CN)CH$_3$.

Preferred for reasons of increased ease of synthesis and/or greater herbicidal efficacy are:
(1) Compounds of Formula I where
R$_4$ is C$_3$-C$_6$ cycloalkyl, C$_5$-C$_6$ cycloalkenyl,

Si(CH$_3$)$_2$(C$_1$-C$_4$ alkyl), Si(CH$_3$)$_2$(C$_2$-C$_4$ alkenyl), Si(CH$_3$)$_2$(C$_1$-C$_3$ alkoxy),

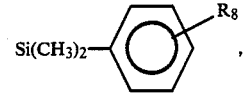

P(O)(CH$_3$)$_2$, P(O)(OCH$_3$)$_2$, C$_1$-C$_4$ alkylcarbonyl, C$_3$-C$_4$ cycloalkylcarbonyl, NR$_9$R$_{10}$ or C$_1$-C$_2$ alkyl substituted with C$_3$-C$_5$ cycloalkyl, C$_1$-C$_3$ alkoxy, C$_1$-C$_3$ haloalkoxy, C$_2$-C$_3$ alkenyloxy, C$_2$-C$_3$ haloalkenyloxy, C$_1$-C$_3$ alkylthio, C$_1$-C$_3$ haloalkylthio, C$_1$-C$_3$ alkylsulfinyl, C$_1$-C$_3$ alkylsulfonyl, C$_1$-C$_3$ haloalkylsulfinyl, C$_1$-C$_3$ haloalkylsulfonyl, Si(CH$_3$)$_2$(C$_1$-C$_4$ alkyl), NO$_2$, CN, C$_1$-C$_2$ alkylcarbonyl, OH, NR$_9$R$_{10}$, CO$_2$(C$_1$-C$_3$ alkyl), SCN, P(O)(OCH$_3$)$_2$ or SO$_2$NR$_{11}$R$_{12}$.
(2) Compounds of Formula I where
W is O;
R is H;
X is C$_1$-C$_2$ alkyl, C$_1$-C$_2$ alkoxy, Cl, F, Br, I, OCF$_2$H, CH$_2$F, CF$_3$, OCH$_2$CH$_2$F, OCH$_2$CHF$_2$, OCH$_2$CF$_3$, CH$_2$Cl or CH$_2$Br; and
Y is H, C$_1$-C$_2$ alkyl, C$_1$-C$_2$ alkoxy, CH$_2$OCH$_3$, CH$_2$OCH$_2$CH$_3$, NHCH$_3$, N(OCH$_3$)CH$_3$, N(CH$_3$)$_2$, CF$_3$, SCH$_3$, OCH$_2$CH=CH$_2$, OCH$_2$C≡CH, OCH$_2$CH$_2$OCH$_3$, CH$_2$SCH$_3$, CH$_2$SCH$_2$CH$_3$, OCH$_2$CH$_2$OCH$_3$,

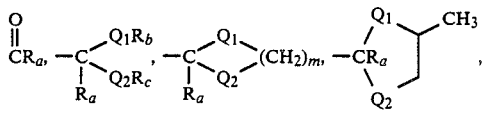

OCF$_2$H, SCF$_2$H, C≡CH or C≡CCH$_3$; and

Z is CH or N; and when R$_4$ is meta to the sulfonylurea bridge, then it is selected from CH$_2$OCH$_3$, CH$_2$OCH$_2$CH$_3$, CH$_2$CH$_2$OCH$_3$, CH$_2$SCH$_3$, CH$_2$SCH$_2$CH$_3$, CH$_2$CH$_2$SCH$_3$, CH$_2$CN, NH$_2$, NHCH$_3$, N(CH$_3$)$_2$ or CH$_2$OH.

(3) Compounds of Preferred 2 where

R$_4$ is C$_3$–C$_6$ cycloalkyl, C$_5$–C$_6$ cyclolkenyl, cyclopropylmethyl, Si(CH$_3$)$_3$, NH$_2$, NHCH$_3$, N(CH$_3$)$_2$, CH$_2$P(O)(OCH$_3$)$_2$, CHO, C(O)CH$_3$, CH$_2$CHO, CH$_2$CO$_2$CH$_3$ or C$_1$–C$_2$ alkyl substituted with C$_1$–C$_2$ alkoxy, C$_1$–C$_2$ alkylthio, C$_1$–C$_2$ alkylsulfinyl, C$_1$–C$_2$alkylsulfonyl, CN, OH or SO$_2$N(CH$_3$)$_2$.

(4) Compounds of Preferred 3 where A is A-1.

(5) Compounds of Preferred 4 where

R$_1$ is H;

R$_2$ is H or CH$_3$;

R$_3$ is H;

R$_5$ is H or CH$_3$;

R$_6$ is H;

R$_7$ is H;

R$_8$ is H;

R$_{13}$ is H, CH$_3$ or Cl;

R$_{14}$ is H, CH$_3$ or Cl; and

Q is O, S or SO$_2$.

(6) Compounds of Preferred 5 where

R$_4$ is ortho to the sulfonylurea bridge and is selected from Si(CH$_3$)$_3$, NH$_2$, NHCH$_3$, N(CH$_3$)$_2$, CH$_2$OCH$_3$, CH$_2$OCH$_2$CH$_3$, CH$_2$CH$_2$OCH$_3$, CH$_2$SCH$_3$, CH$_2$SCH$_2$CH$_3$, CH$_2$CH$_2$SCH$_3$, CH$_2$SO$_2$CH$_3$, CH$_2$SO$_2$CH$_2$CH$_3$, CH$_2$CH$_2$SO$_2$CH$_3$, CH$_2$CN, CH$_2$CH$_2$CN or CH$_2$CH$_2$SO$_2$N(CH$_3$)$_2$;

X is CH$_3$, OCH$_3$, OCH$_2$CH$_3$, Cl, OCF$_2$H or OCH$_2$CF$_3$; and

Y is CH$_3$, OCH$_3$, C$_2$H$_5$, CH$_2$OCH$_3$, NHCH$_3$, CH(OCH$_3$)$_2$ or cyclopropyl.

(7) Compounds of Preferred 6 where J is J-1.
(8) Compounds of Preferred 6 where J is J-2.
(9) Compounds of Preferred 6 where J is J-3.
(10) Compounds of Preferred 6 where J is J-4.
(11) Compounds of Preferred 6 where J is J-5.
(12) Compounds of Preferred 6 where J is J-6.
(13) Compounds of Preferred 6 where J is J-7.
(14) Compounds of Preferred 6 where J is J-8.
(15) Compounds of Preferred 6 where J is J-9.
(16) Compounds of Preferred 6 where J is J-10.
(17) Compounds of Preferred 6 where J is J-11.
(18) Compounds of Preferred 6 where J is J-12.
(19) Compounds of Preferred 6 where J is J-13.
(20) Compounds of Preferred 7 where Q is SO$_2$.
(21) Compounds of Formula I where J is J-1, J-2, J-3, J-4, J-5 or J-6; and R$_4$ is C$_3$–C$_6$ cycloalkyl, C$_5$–C$_6$ cycloalkenyl,

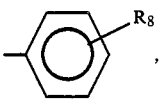

Si(CH$_3$)$_2$(C$_1$–C$_4$ alkyl), Si(CH$_3$)$_2$(C$_2$–C$_4$ alkenyl), Si(CH$_3$)$_2$(C$_1$–C$_3$ alkoxy),

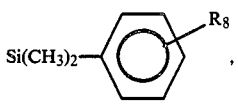

P(O)(CH$_3$)$_2$, P(O)(OCH$_3$)$_2$, CN, NR$_9$R$_{10}$ or C$_1$–C$_2$ alkyl substituted with C$_3$–C$_5$ cycloalkyl, C$_1$–C$_3$ alkoxy, C$_1$–C$_3$ haloalkoxy, C$_2$–C$_3$ alkenyloxy, C$_2$–C$_3$ haloalkenyloxy, C$_1$–C$_3$ alkylthio, C$_1$–C$_3$ haloalkylthio, C$_1$–C$_3$ alkylsulfinyl, C$_1$–C$_3$ alkylsulfonyl, C$_1$–C$_3$ haloalkylsulfinyl, C$_1$–C$_3$ haloalkylsulfonyl, Si(CH$_3$)$_2$(C$_1$–C$_4$ alkyl), NO$_2$, CN, NR$_9$R$_{10}$, CO$_2$(C$_1$–C$_3$ alkyl), SCN, P(O)(OCH$_3$)$_2$ or SO$_2$NR$_{11}$R$_{12}$.

Specifically preferred for reasons of their expected greatest ease of synthesis and/or greatest herbicidal efficacy are:

N-[(4,6-dimethoxypyrimidin-2-yl)aminocarbonyl]-2,3-dihydro-6-(methoxymethyl)-2-methylbenzo[b]thiophene-7-sulfonamide, 1,1-dioxide, m.p. 206°–208° C.;

N-[(4,6-dimethoxypyrimidin-2-yl)aminocarbonyl]-2,3-dihydro-2-methyl-6-(trimethylsilyl)benzo[b]thiophene7-sulfonamide, 1,1-dioxide, m.p. 188°–190° C.;

N-[(4-methoxy-6-methyl-1,3,5-triazin-2-yl)aminocarbonyl]-2,3-dihydro-6-(methoxymethyl)-2-methylbenzo[b]thiophene-7-sulfonamide, 1,1-dioxide, m.p. 184°–186° C.; and N-[(4,6-dimethoxypyrimidin-2-yl)aminocarbonyl]-2,3-dihydro-6-(cyanomethyl)-2-methylbenzo[b]thiophene-7-sulfonamide, 1,1-dioxide, m.p. 207°–209° C.

The present invention also includes agriculturally suitable compositions for controlling the growth of undesirable vegetation comprising an effective amount of the compounds of the invention and at least one of a surfactant, solid or liquid diluent.

Another embodiment of the present invention involves a method of using said compounds and compositions in controlling the growth of undesired vegetation by applying them to the locus to be protected in an effective amount.

DETAILED DESCRIPTION OF THE INVENTION

Synthesis

The following discussion represents a general outline for the preparation of the compounds of this invention. All of the syntheses described below are multistep with one or more methods being taught for each step. This allows for a wide variety of possible synthetic pathways to prepare a particular compound of Formula I. The proper choice of the synthetic pathway and the best ordering of the reaction sequences for each individual compound will be known to one skilled in the art.

The compounds of Formula I can be prepared by one or more of the methods described below in Equations 1 through 5.

As shown in Equation 1, many of the compounds of Formula I where J is $J_1$ to $J_{13}$, but is not $J_{10}$, can be prepared by reacting a sulfonyl isocyanate (W=O) or, a sulfonyl isothiocyanate (W=S) of Formula II with an appropriate heterocyclic amine of Formula III. R, A and W are as previously defined.

Equation 1

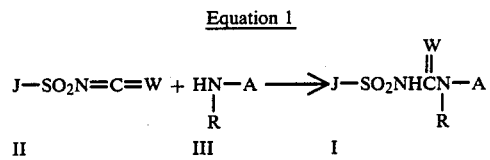

The reaction is carried out at 25° to 100° C. in an inert, aprotic solvent such as methylene chloride or xylene for 0.5 to 24 hours as taught in U.S. Pat. No. 4,127,405.

Many of the compounds of Formula I, where J is $J_1$ to $J_9$ or $J_{11}$ to $J_{13}$ and where W is S and R is H, (Ia) can be prepared by reacting the appropriate sulfonamide of Formula IV with a heterocyclic isothiocyanate of Formula V, as shown in Equation 2.

Equation 2

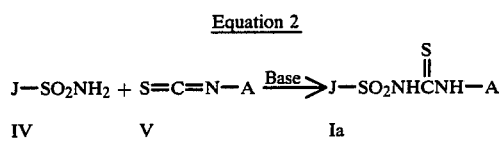

The reaction is carried out at 25° to 80° C. in an inert, aprotic solvent such as acetone or acetonitrile in the presence of a base such as potassium carbonate for 0.5 to 24 hours. The required heterocyclic isothiocyanates V are prepared from the corresponding amines III which would be known to one skilled in the art as taught in EPO Publication No. 35,893.

Many of the compounds of Formula I, where J is $J_1$ to $J_{13}$ and W is O (Ib), can be prepared by reacting a sulfonylcarbamate of Formula VI with an appropriate amine of Formula III, as shown in Equation 3.

Equation 3

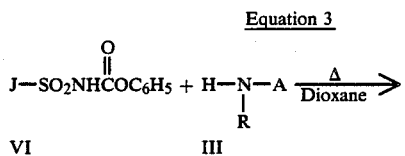

The reaction is carried out at 50° to 100° C. in a solvent such as dioxane for 0.5 to 24 hours. The required carbamates VII are prepared by reacting the corresponding sulfonamides IV with diphenylcarbonate in the presence of a strong base.

Compounds of Formula Ib can also be prepared, as shown in Equation 4, by reacting a heterocyclic carbamate of Formula VII with an appropriate sulfonamide of Formula IV.

Equation 4

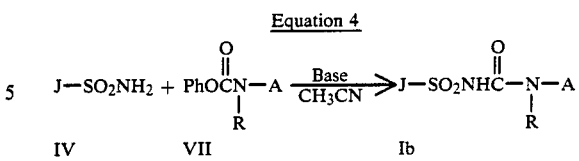

The reaction is carried out at 0° to 50° C. in a solvent such as acetonitrile or dioxane in the presence of a non-nucleophilic base such as DBU for 0.2 to 24 hours. The required phenylcarbamate VII are prepared by reacting the corresponding heterocyclic amines III with diphenylcarbonate or phenylchloroformate in the presence of a strong base.

Many of the compounds of Formula Ib where J is $J_1$ to $J_3$ and $J_8$ to $J_{13}$ can be prepared by reacting the sulfonamides of Formula IV with an appropriate methylcarbamate of Formula VIII in the presence of an equimolar amount of trimethylaluminum, as shown in Equation 5.

Equation 5

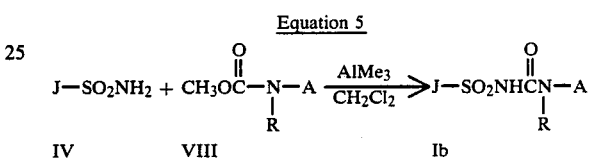

The reaction is carried out at 25° to 40° C. in a solvent such as methylene chloride for 10 to 96 hours under an inert atmosphere. The required carbamates VIII are prepared by reacting the corresponding amines III with dimethylcarbonate or methyl chloroformate in the presence of a strong base.

The intermediate sulfonyl isocyanates (W=O) and sulfonyl isothiocyanates (W=S) of Formula II from Equation 1 can be prepared as shown in Equations 6 through 9.

As shown in Equation 6, many of the sulfonyl isocyanates of Formula IIa where J is $J_1$ to $J_3$ and $J_5$ to $J_{13}$ can be prepared by the reaction of sulfonamides of Formula IV with phosgene, in the presence of n-butylisocyanate and a tertiary amine catalyst, at reflux in a solvent such as xylene by the method of U.S. Pat. No. 4,238,621.

Equation 6

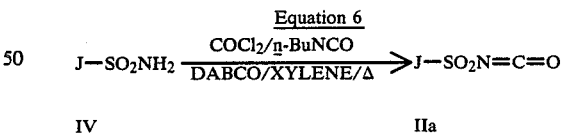

The sulfonylisocyanates can also be prepared from the sulfonamides by a two step procedure involving (a) reacting the sulfonamides with n-butylisocyanate in the presence of a base such as $K_2CO_3$ at reflux in an inert solvent such as 2-butanone forming a n-butylsulfonylurea; and (b) reacting this compound with phosgene and a tertiary amine catalyst at reflux in xylene solvent. The method is similar to a procedure taught by Ulrich and Sayigh, *Newer Methods of Preparative Organic Chemistry*, Vol. VI, p. 223–241, Academic Press, New York and London, W. Foerst Ed.

An alternative two step procedure for preparing sulfonylisocyanates of Formula IIa where J is $J_1$ to $J_9$ and $J_{11}$ to $J_{13}$ is shown in Equation 7.

Equation 7

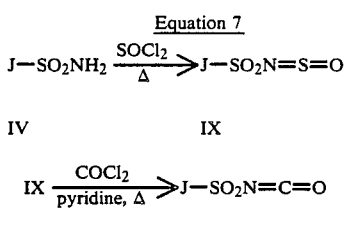

The sulfonamides of Formula IV are heated with excess thionyl chloride forming N-sulfinyl sulfonamides of Formula IX. The intermediate N-sulfinyl sulfonamides are heated in an inert solvent such as toluene with phosgene (e.g. 2-3 equivalents) and pyridine (e.g. 0.1 equivalents) to give sulfonyl isocyanates of Formula IIa. The method is similar to that taught by Ulrich et al. *J. Org. Chem.* 34, 3200 (1969).

Alternatively, as shown in Equation 8, many of the sulfonyl isocyanates of Formula IIa where J is $J_1$ to $J_{13}$ can be prepared by reacting the corresponding sulfonyl chlorides X with cyanic acid salts.

Equation 8

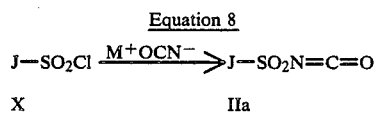

The reaction is carried out at 25° to 100° C. in an inert aprotic solvent such as acetonitrile for 0.5-24 hours in the presence of phosphorus pentoxide and an alkali metal salt such as lithium iodide.

Many of the sulfonyl isothiocyanates of Formula IIb where J is $J_1$ to $J_9$ and $J_{11}$ and $J_{13}$ can be prepared, as shown in Equation 9, by contacting the sulfonamides of Formula IV with carbon disulfide in the presence of two equivalents of a strong base. The resulting salt is then reacted with phosgene according to the teachings of K. Hartke, *Arch. Pharm.*, 299, 174 (1966).

Equation 9

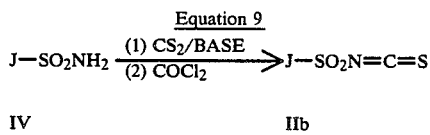

The sulfonamides of Formula IV where J is $J_1$ to $J_{13}$ of Equations 2, 4, 5, 6, 7 and 9 as well as the other sulfonamides required to prepare the compounds of this invention can be prepared from the corresponding sulfonyl chlorides of Formula X by contacting with either anhydrous or aqueous ammonia as shown in Equation 10.

Equation 10

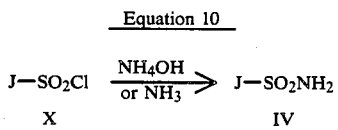

The preparation of sulfonamides from sulfonyl chlorides is widely reported in the literature, for reviews see: F. Hawking and J. S. Lawrence, "The Sulfonamides," H. K. Lewis and Co., London, 1950 and E. H. Northey, "The Sulfonamides and Allied Compounds," Reinhold Publishing Corp., New York, 1948.

Alternatively, many sulfonamides IV can be prepared by dealkylation of their corresponding N-t-butyl sulfonamides XI as shown in Equation 11.

Equation 11

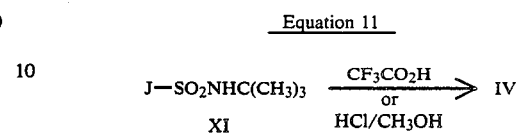

The reaction is carried out by contacting the N-t-butyl sulfonamide XI with a strong acid such as trifluoroacetic acid or methanolic HCl at 0° to 50° C. for 0.5 to 24 hours. The N-t-butyl sulfonamides XI are readily prepared by reacting sulfonyl chlorides X with t-butylamine and are useful either as an aid in purification, to enhance solubility for subsequent reactions such as Equation 12 below or to protect the sulfonamide function from competing with reactions at other parts of the molecule.

Many of the sulfonamides of Formula XI in which $R_4$ is ortho to the sulfonamide group can be prepared as in Equations 12, 13 and 14.

Equation 12

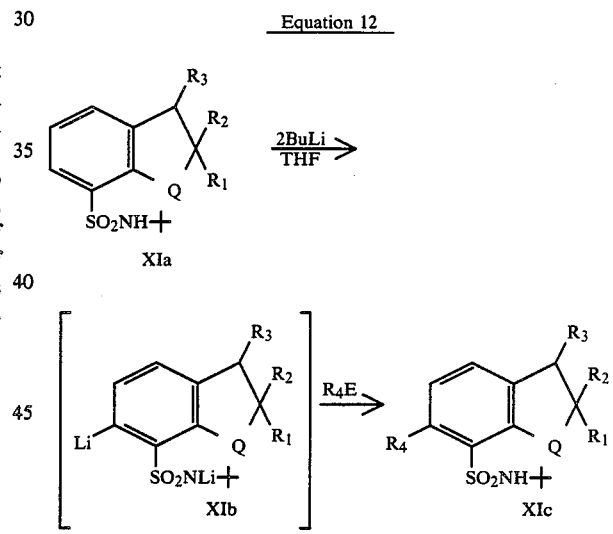

The reaction is carried out by contacting sulfonamides XIa with an appropriate organolithium reagent such as n-butyl lithium in an inert aprotic solvent such as tetrahydrofuran at −78° to 30° C. for 0.5 to 5 hours. The dilithiated intermediate XIb is contacted with an electrophile ($R_4E$) for 1 to 48 hours at −78° to 50° C. to give XIc. The nature of the $R_4$ group will determine which of the standard isolation and purification methods one uses. Similar reaction methods are described by Lombardino, *J. Org. Chem.* 36, 1843 (1971). Examples of appropriate electrophiles are described by Gschwend and Rodriguez *Org. React.* 26, 1 (1979).

By methods similar to those described for Equation 12, many sulfonamides of Formula XIe and XIg can be prepared from sulfonamides XId and XIf, respectively as shown Equation 13.

Equation 13

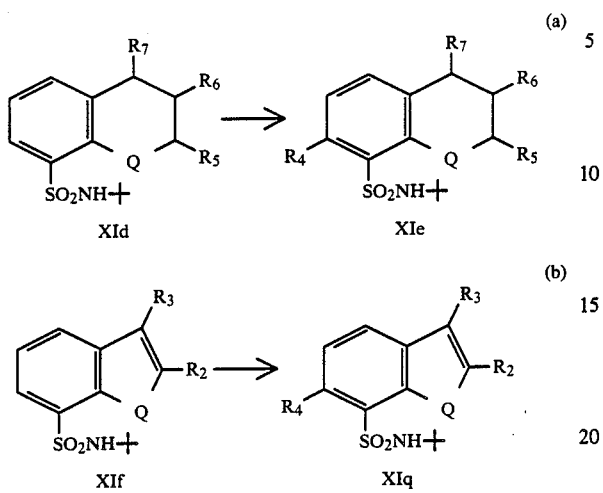

Alternatively, sulfonamides of Formula XIg can be prepared by dehydrogenating sulfonamides of Formula XIc ($R_1$=H) using such reagents as 2,3dichloro-5,6-dicyano-b 1,4-benzoquinone, nickel peroxide, or platinum. Use of such reagents to dehydrogenate heterocycles is described in Bianchi, *J. Chem. Res(S)*, 311 (1971); Evans, *J. Org. Chem.* 44, 497 (1979); and Karakhanov, *Get. Katal. Reakt, Poluch. Prev. Geteros. Soedin*, 81 (1971).

Many examples of other t-butyl sulfonamides of Formula XI where $R_4$ is ortho to the sulfonamide group may be prepared by the method outlined in Equations 12 and 13. The reaction conditions will vary depending upon the nature of J and the $R_4$ groups will be obvious to one skilled in the art.

While many of the $R_4$ groups can be introduced directly, as described above, some of the $R_4$ groups may best be prepared by standard functional group manipulations upon compounds of Formulae XIc, XIe, and XIg containing an appropriate $R_4$ group pecursor as will be known to one skilled in the art. Some examples of these manipulations are the preparation of XIc where $R_4$ contains a sulfone by the oxidation of XIc where $R_4$ contains a thioether function, the preparation of XIg where $R_4$ contains CN by a displacement reaction on XIg where $R_4$ contains a reactive halogen, or by the preparation of XIe where $R_4$ contains $NH_2$ by the reduction of XIe where $R_4$ contains $NO_2$.

Many of the sulfonamides of Formula XI in which $R_4$ is attached ortho to the sulfonamide group via a single methylene unit can be prepared as exemplified in Equation 14.

Equation 14

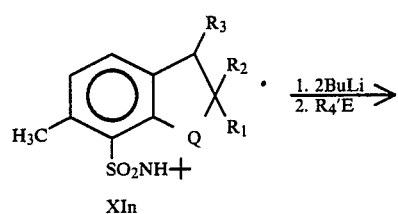

Equation 14 -continued

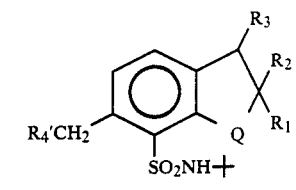

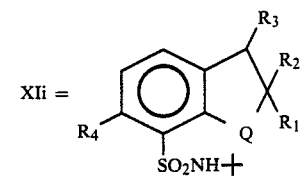

In Equation 14 $R_4'E$ represents a suitable electrophile which reacts to give the $R_4'CH_2$ (equivalent to $R_4$) group. The reaction is carried out under reaction conditions similar to those of Equation 12. Many sulfonamides of Formula XI may be prepared similarly from the appropriate ortho-methyl-t-butyl sulfonamides. The preparation of appropriate orthomethylsulfonamides is well known in the literature and is taught in U.S. Pat. No. 4,514,211, U.S. Pat. No. 4,492,596, U.S. Pat. No. 4,370,479, U.S. Pat. No. 4,465,506, U.S. Pat. No. 4,369,320, No. EP-A-107,979, No. EP-A-123,303, South African Patent Appln. No. 84/3522, South African Patent Appln. No. 83/5165, and the literature references cited therein.

Many sulfonamides of Formula XI can be prepared as exemplified in Equation 15.

Equation 15

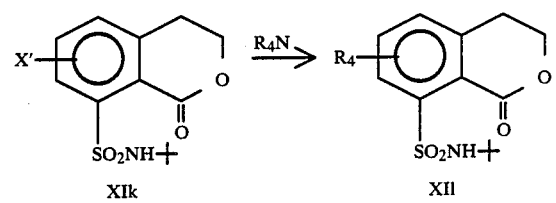

In Equation 15, X' represents a halogen (F, Cl, Br, or I) or a pseudo halogen. $R_4N$ represents a suitable nucleophile which will be known to one skilled in the art. The halosulfonamide XIk is reacted with a suitable nucleophile $R_4N$ in an inert solvent such as dimethylformamide between 0° C. and 190° C. at atmospheric pressure or above for 1 to 24 hours. In some cases a catalyst may be required. Procedures for such substitutions are described in *Advanced Organic Chemistry*, 3rd Ed., Ch. 13, John Wiley and Sons, New York, J. March, Ed. and the references cited therein.

Many sulfonamides of Formula XI can be similarly prepared from their analogous halosubstituted sulfonamides. The appropriate halosubstituted sulfonamides are well known in the literature and may be prepared as taught in U.S. Pat. No. 4,514,211, U.S. Pat. No. 4,492,596, U.S. Pat. No. 4,370,479, U.S. Pat. No. 4,465,506, U.S. Pat. No. 4,369,320, No. EP-A-107,979, No. EP-A-123,303, South African Pat. Appln. No.

84/3522, South African Pat. Appln. No. 83/5165, and the references cited therein.

Many of the t-butyl sulfonamides of Formula XIa (Q=S) in Equation 12 and of Formula XId (Q=S) in Equation 13 can be prepared by the sequence of reactions shown in Equation 16.

Equation 16

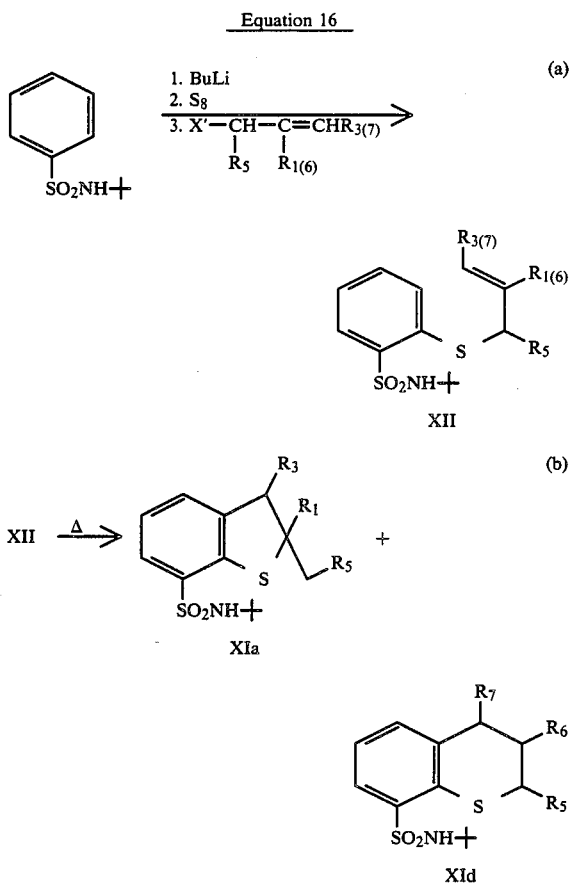

wherein
$R_1$, $R_3$, $R_5$, $R_6$ and $R_7$ are as previously defined and in XIa the $CH_2R_5$ unit is equivalent to $R_2$ as previously defined.

$X'$ is a reactive halogen.

The reactions of Equation 16(a) are run in-situ. The dilithio salt of t-butylbenzenesulfonamide is prepared according to the teachings of Lombardino, *J. Org. Chem.* 36, 1843 (1971) and is contacted with elemental sulfur and an appropriate allyl halide to afford XII. The method is similar to those taught by Gronowitz, *Acta. Chem. Scand.* 21, 812 (1967). The allylthioether XII in Equation 16(b) is heated either neat or in a solvent such as quinoline at 150°-300° C. for 0.25 to 2.0 hours to cause cyclization to both XIa and XId which can be separated and purified by standard chromatography and recrystallization procedures.

Sulfonamides of Formula IV (Q=SO, SO₂) and XI (Q=SO, SO₂) can be prepared from the corresponding sulfonamides IV (Q=S) and XI (Q=S) by well known oxidation procedures. Barnard et al. have reviewed such procedures in *Organic Sulfur Compounds Vol. 1*, 229 Kharasch ed., Pergamon Press 1961.

Sulfonamides of Formula IV (J=J-2, Q=SO₂) can be reduced stepwise to sulfonamide IV (J=J-1, Q=S) by methods taught by Bordwell, *J. Am. Chem. Soc.* 77, 5939 (1955) and Bordwell, *J. Amer. Chem. Soc.* 73, 2251 (1951).

The sulfonyl chlorides of Formula X of Equations 8 and 10 are important intermediates for the preparation of the compounds of this invention. The syntheses of the required sulfonyl chloride intermediates where J is $J_1$ to $J_{13}$ are described in Equations 17 through 20.

As shown in Equation 17, many of the sulfonyl chlorides of Formula X can be prepared from the corresponding amines XIII.

Equation 17

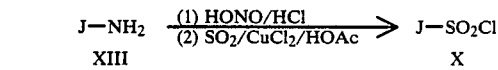

The reaction involves diazotization of the amine XIII with sodium nitrite in HCl, followed by reaction of the diazonium salt with sulfur dioxide and cupric chloride in acetic acid analogous to the teachings of Yale and Sowinski, *J. Org. Chem.*, 25, 1824 (1960).

Alternatively, sulfonyl chlorides of Formula X can be prepared by a modification of the above procedure whereby the diazotization reaction is carried out in dilute sulfuric acid and the resulting diazonium salt is reacted with sulfur dioxide, HCl and cupric chloride in a cosolvent mixture consisting of acetic acid-water (1:1) and an immiscible, inert solvent such as 1-chlorobutane or methylene chloride at 0°-40° C. for 1 to 24 hours. The method for preparing diazonium salts from benzofuranamines and benzo[b]thiopheneamines is widely reported in the literature, e.g., Bordwell and Stange, *J. Am. Chem. Soc.*, 27, 5939 (1955); Arnold and McCool, ibid 64, 1315 (1942); Neth. Appl. No. 6,602,601; and U.S. Pat. No. 4,032,649.

Many of the sulfonyl chlorides of Formula X can also be prepared by oxidative chlorination of the corresponding thio compounds of Formula XIV as shown in Equation 18. R' is H, alkyl, benzyl or carbamoyl, $R_4$ does not have a thio or sulfinyl linkage and Q is not S or SO.

Equation 18

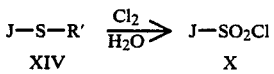

The reaction is carried out by addition of molecular chlorine or a chlorine equivalent to the thio compound in the presence of water at 0° to 80° C. in an aliphatic carboxylic acid solvent such as acetic acid or an inert organic solvent such as dichloroethane for 1 to 24 hours.

Alternatively, many of the sulfonyl chlorides of Formula X can be prepared by the two-step sequence shown in Equation 19 starting from the thio compounds XIV where R' is H (XIVa) and $R_4$ does not have a thio or sulfinyl linkage.

Equation 19

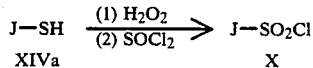

The thiol XIVa is contacted with excess hydrogen peroxide in the presence of base to give a sulfonic acid salt which in turn is converted to the desired sulfonyl chloride by contacting with a suitable reagent such as thionyl chloride or phosphorous pentachloride as known to one skilled in the art.

Many of the sulfonyl chlorides of Formula X where J is $J_1$, $J_2$, $J_3$, $J_{11}$, $J_{12}$, or $J_{13}$ and Q is O or S can be prepared from the corresponding lithium or Grignard reagent of Formula XV and sulfuryl chloride as shown in Equation 20. J is $J_1$, $J_2$, $J_3$, $J_{11}$, $J_{12}$, or $J_{13}$ and M represents either the lithium or MgX' moiety of the metalated reagent.

Equation 20

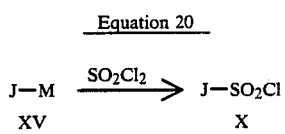

The metalated intermediates XV are contacted with sulfuryl chloride to afford sulfonyl chlorides X. The procedure for preparing similar sulfonyl chlorides by this method is taught by Bhattacharya et al., *J. Chem. Soc.* (C), 1265 (1968).

Some of the sulfonyl chlorides of Formula X may best be prepared by direct chlorosulfonation depending on the substitution pattern on the ring and the nature of the substituent as will be known to one skilled in the art. Methods for preparing many sulfonyl chlorides X by reaction with chlorosulfonic acid are taught by Hoffman, *Org. Syn* 60, 121 (1981); Young, *J. Amer. Chem. Soc.* 59, 811 (1937); and Radzhabov, *Dokl. Akad. Nauk. Tadzh. SSR* 16, 35 (1973).

Many of the S-arylthiocarbamates of Formula XIVb (XIV, R'=CON(CH$_3$)$_2$) can be prepared by the Newman-Kwart rearrangement starting with the corresponding phenols XVI as shown in Equation 21.

Equation 21

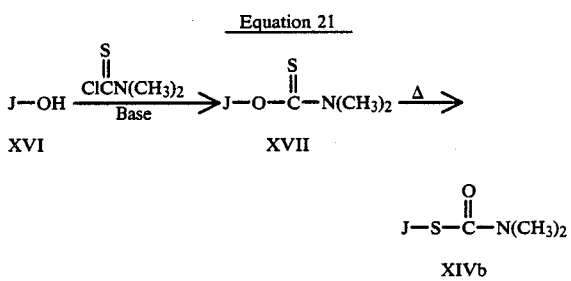

The phenol XVI is first reacted with N,N-dimethyl-thiocarbamoyl chloride in the presence of a base. The resulting O-aryl-N,N-dimethylthiocarbamate XIV is then heated at 150° C. to 300° C. for 2 to 24 hours as taught by Newman and Karnes *J. Org. Chem.*, 31, 3980 (1966) to give the desired S-aryl-N,N-dimethylthiocarbamate XIVb. The corresponding thiols XIVa can be obtained by hydrolysis of the thiocarbamates XIVb.

Many of the sulfides of Formula XIV where R' is alkyl or benzyl can be prepared by reacting a halocompound of Formula XVIII with an appropriate mercaptan in the presence of a base as shown in Equation 22. R' is alkyl or benzyl and X' is F, Cl, Br or I.

Equation 22

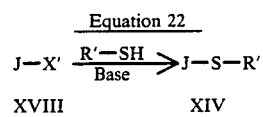

The reaction is carried out in a solvent such as DMF at 25° to 150° C. for 0.5 to 24 hours. The halocompounds XVIII must not contain functionality which can be attacked by a mercaptide anion as will be known to one skilled in the art. An example of this would be where J is $J_1$ and $R_4$ was a haloalkyl group.

Many of the sulfides of Formula XIV where J is $J_4$, $J_5$ or $J_6$ can be prepared by methods taught in Eup. Appl. No. 107979, or simple modifications thereof, by one skilled in the art. As an example, Equation 23 outlines the preparation of sulfide XIVc (XIV: J=J-4, n=0) from an appropriately substituted sulfide of Formula XIX.

Equation 23

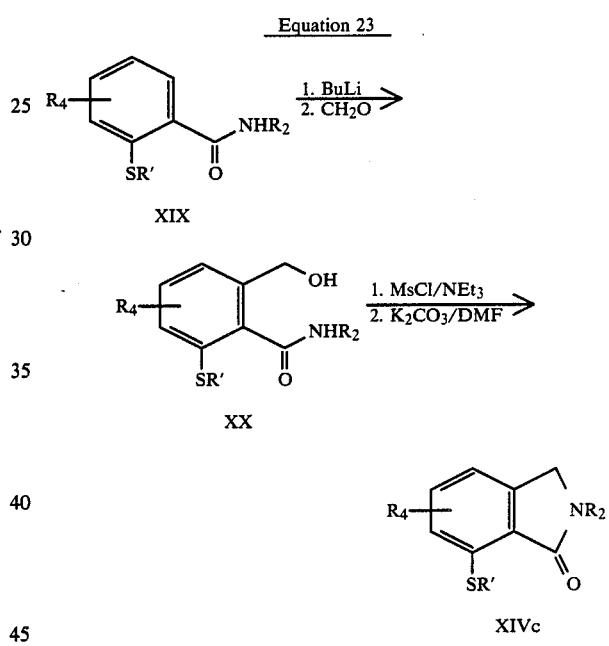

Many of the halocompounds XVIII of Equation 22 where J is $J_1$, $J_2$ and $J_3$ and Q is S or O can be prepared by the reaction sequence exemplified by the synthesis of halocompound XVIIIa (XVIII, J=J-3, $R_7$=H) in Equation 24.

Equation 24

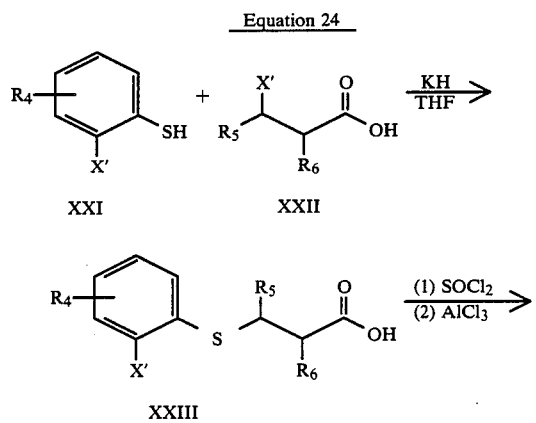

-continued
Equation 24

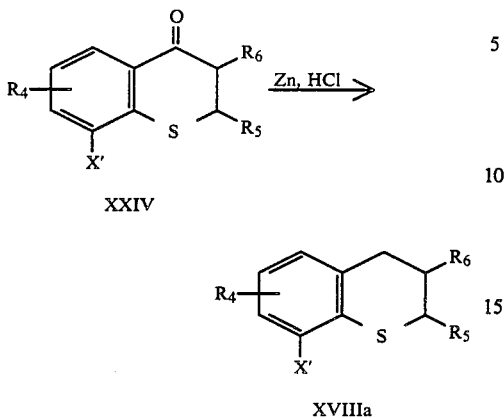

The thiophenol XXI is contacted with two equivalents of a base, such as sodium or potassium hydride, and an appropriately substituted halo acid of Formula XXII in an inert polar aprotic solvent such as THF at reflux for 2 to 24 hours. The substituted acid XXIII is formed and can be isolated and purified by standard methods well known to one skilled in the art. Acid XXIII is converted to its acid chloride and cyclized to ketone XXIV by methods similar to those described by Ong, Eur. Pat. Appl. No. 0050326. Ketone XXIV can be reduced to give halocompound XVIIIa by methods described by Martin, J. Am. Chem. Soc. 58, 1438 (1936).

By methods analogous to those described in Equation 24, one can prepare halocompounds of Formula XVIIIb ($R_3 = H$) from thiophenols XXI and halo acids XXIIa as shown in Equation 25.

Equation 25

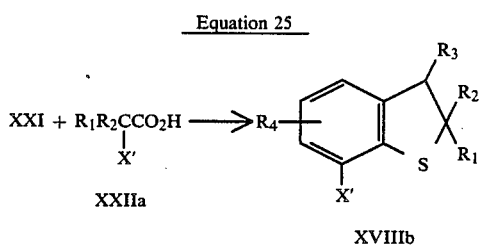

The reaction methods exemplified by Equations 23, 24, and 25 can be used to prepare intermediates toward sulfonylureas of Formula I in which $R_4$ is meta to the sulfonamide group. These methods can also be used to prepare sulfonylureas I in which an ortho $R_4$ group cannot be introduced by the methods described in Equations 12, 13, 14 and 15.

Methods for preparing examples of halocompounds of Formula XVIII where $J=J-2$ and $Q=S$, SO, $SO_2$ are described in Ong, Eup. Pat. Appl. No. 0050326. Methods for preparing halocompounds of Formula XVIII where $J=J-1$ ($Q=O$) and $J=J-2$ ($Q=O$) are well known and are described in Goldenberg, Chim. Therap. 221 (1961) and Mustafa, Heterocyclic Compounds Vol. 29, Weisberger and Taylor eds. (1974). Methods for preparing halocompounds of Formula XVIII where $J=J_4$, $J_5$ or $J_6$ are described in Eup. Appl. No. 107979.

Many halocompounds of Formula XVIII in Equation 22 are also intermediates toward compounds of Formula XV of Equation 20. They can be prepared by functional group modifications of intermediate halocompounds which are known in the art. As an example, Equation 26 outlines the preparation of XVIIIa from an appropriately substituted aryl halide XXV.

Equation 26

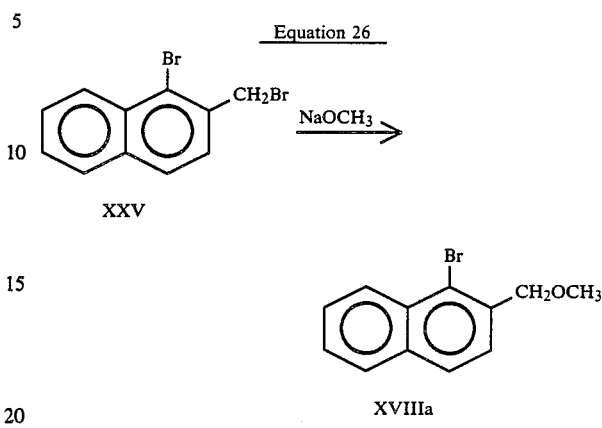

The preparation of a variety of halocompounds which can be precursors to halocompounds of Formula XVIII is described in the literature. For example, see U.S. Pat. No. 4,465,506 and U.S. Pat. No. 4,370,479.

The amines of Formula XIII in Equation 17 can be prepared by reduction of the corresponding nitro compounds of Formula XXVI as shown in Equation 27.

Equation 27

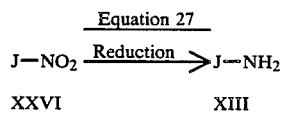

XXVI      XIII

The reduction of nitro compounds to amines can be carried out by any of several known methods as described in Preparative Organic Chemistry, 4 Ed., p. 557–563, John Wiley and Sons, New York and London, G. Hilgetag and A. Martini Ed.

Several methods for preparing amines of Formula XIII and their precursor nitro compounds XXV where $J=J_1$, $J_2$ and $J_3$ are described in No. EP-A-79683, U.S. Pat. No. 4,492,596, and the references cited therein. Methods for preparing nitro compounds of Formula XXVI where $J=J_4$, $J_5$, $J_6$, $J_7$, $J_8$ and $J_9$ are described in No. EP-A-107,979, U.S. Pat. No. 4,514,211 and the references cited therein.

The heterocyclic amines of Formula III in Equations 1 and 3 can be prepared by methods known in the literature, or simple modifications thereof, by one skilled in the art.

For a review of the synthesis and reactions of 2-amino- and 2-methylaminopyrimidines III (A=A-1, Z=CH) see The Chemistry of Heterocyclic Compounds, Vol. 16, Wiley-Interscience, New York (1962). For a review of the synthesis and reactions of 2-amino- and 2-methylamino-s-triazines III (A=A-1, Z=N) see The Chemistry of Heterocyclic Compounds, Vol. 13, Wiley-Interscience, New York (1959), F. C. Schaefer, U.S. Pat. No. 3,154,547 and F. C. Schaefer and K. R. Huffman, J. Org. Chem., 28, 1812 (1963). EP-A No. 84,224 and W. Braker et al., J. Chem. Soc., 69, 3072 (1947) describes methods for preparing aminopyrimidines and triazines substituted by acetal groups such as dialkoxymethyl or 1,3-dioxolan-2-yl. U.S. Pat. No. 4,515,626 describes methods for the synthesis of cyclopropylpyrimidines and triazines substituted by such groups as alkyl, haloalkyl, alkoxy, haloalkoxy, alkylamino, dialkylamino or alkoxyalkyl.

The 5,6-dihydrofuro[2.3-d]pyrimidine-2-amines, the cyclopenta[d]pyrimidines-2-amines (III, A is A-2) and the 6,7-dihydro-5H-pyrano[2.3-d]pyrimidin-2-amines (III, A is A-3) can be prepared as taught in U.S. Pat. No. 4,339,267. The furo[2.3-d]pyrimidin-2-amines (III, A is A-4) are described in U.S. Pat. No. 4,487,626.

Compounds of Formula III, where A is A-5, are described in No. EP-A-73,562. Compounds of Formula III, where A is A-6, are described in U.S. Pat. No. 4,496,392.

The amines of Formula III where A is A-7 can be prepared by methods taught in European Publication No. 125,864 (published Nov. 21, 1984 or by suitable modifications that would be obvious to one skilled in the art.

The preparation of the compounds of this invention is further illustrated by the following examples.

EXAMPLE 1

N-t-Butyl-2-(2-propenylthio)benzenesulfonamide

To a solution of 85.3 g of N-t-butylbenzenesulfonamide in 900 ml of dry tetrahydrofuran was added 525 ml of a 1.6M hexane solution of n-butyllithium at $-20°$ C. under an inert atmosphere. The mixture was allowed to come to room temperature and was stirred for 2 hours. The resulting mixture was recooled to $-60°$ C., was contacted with 13 g of sulfur, was allowed to come to room temperature, and was stirred for 2 hours. It was again cooled to $-20°$ C., was contacted with 36 ml of allyl bromide, and was stirred overnight at room temperature. The reaction mixture was contacted with 120 ml of 6N hydrochloric acid and 30 ml of concentrated hydrochloric acid. The mixture was extracted with chlorobutane, dried over magnesium sulfate, concentrated, and recrystallized from hexanechlorobutane to give 89.9 g of the title compound as an orange-brown solid.

60 MHz NMR (CDCl$_3$)δ: 1.20 (s, 9H; CH$_3$); 3.72 (m, 2H, CH$_2$); 5.0–6.0 (m, 3H, vinyl H); 7.5 (m, 3H, arom); and 8.1 (m, 1H, arom).

IR (nujol) 3370 cm$^{-1}$.

EXAMPLE 2

(a)

N-t-Butyl-2,3-dihydro-2-methylbenzo[b]thiophene-7-sulfonamide

A mixture of 89.9 g of N-t-butyl-2-(2-propenylthio)benzenesulfonamide and quinoline (90 ml) were heated at 220° C. for 2 hours under an inert atmosphere. The mixture was cooled, was poured into ice-water (500 ml) and was extracted with several portions of a 1:1 mixture of chlorobutane and tetrahydrofuran. The combined extracts were washed with 6N hydrochloric acid and brine. The organic mixture was dried over magnesium sulfate and was concentrated. The residue was distilled in a kugelrohr apparatus at 170°–200° C. (1 torr), giving after trituration with chlorobutane and hexane a yellow solid. Chromatography of the mixture on silica gel eluting with 20% ethyl acetate in hexane afforded after recrystallization from hexanechlorobutane the title compound as a white solid, m.p. 97°–98° C.

90 MHz NMR (CDCl$_3$)δ: 1.21 (s, 9H, CH$_3$); 1.44 (d, 3H, CH$_3$); 3.00 (m, 1H, CH); 3.47 (m, 1H, CH); 4.02 (m, 1H, CH); 5.03 (s, 1H, NH); 7.27 (m, 2H, arom); and 7.80 (m, 1H, arom).

IR (nujol) 3250 cm$^{-1}$.

(b)

N-t-Butyl-3,4-dihydro-2H-1-benzothiopyran-8-sulfonamide

The chromatography described in part (a) also afforded after recrystallization from chlorobutane/hexane the title compound as a yellow solid, m.p. 137°–139° C.

90 MHz NMR (CDCl$_3$)δ: 1.20 (s, 9H, CH$_3$); 2.16 (m, 2H, CH$_2$); 2.86 (m, 4H, CH$_2$); 5.37 (s, 1H, NH); 7.19 (m, 2H, arom); and 7.83 (m, 1H, arom).

IR (nujol) 3300 cm$^{-1}$.

EXAMPLE 3

N-t-Butyl-2,3-dihydro-6-methoxymethyl-2-methylbenzo[b]thiophene-7-sulfonamide

To a solution of 7.14 g of N-t-butyl-2,3-dihydro-2-methylbenzo[b]thiophene-7-sulfonamide in 175 ml of dry tetrahydrofuran was added 34 ml of a 1.6M hexane solution of n-butyl lithium at $-40°$ C. to $-30°$ C. under an inert atmosphere. The mixture was allowed to warm and was stirred at room temperature for 30 minutes. It was recooled to $-30°$ C. and was contacted with 2.2 ml of bromomethyl methyl ether. The mixture was allowed to come to room temperature overnight and was acidified with 10 ml of 6N hydrochloric acid. The organic layer was separated, was dried over magnesium sulfate, and was concentrated to give 7.4 g of the title compound as a brown oil.

60 MHz NMR (CDCl$_3$)δ: 1.22 (s, 9H, CH$_3$); 1.40 (d, 3H, CH$_3$); 3.43 (s, 3H, CH$_3$); 2.5–3.9 (m, 3H, CH, CH$_2$); 4.80 (s, 2H, CH$_2$O); 5.28 (s, 1H, NH); and 7.27 (m, 2H, arom).

IR (neat) 3320 cm$^{-1}$.

EXAMPLE 4

N-t-Butyl-2,3-dihydro-2-methyl-6-trimethylsilylbenzo[b]thiophene-7-sulfonamide

To a solution of 4.0 g of N-t-butyl-2,3-dihydro-2-methylbenzo[b]thiophene-7-sulfonamide in 175 ml of dry tetrahydrofuran was added 20 ml of a 1.6M hexane solution of n-butyl lithium at $-40°$ C. to $-30°$ C. under an inert atmosphere. The mixture was allowed to warm and was stirred at room temperature for 30 minutes. It was recooled to $-30°$ C. and was contacted with 3.0 ml of chlorotrimethylsilane. The mixture was stirred at room temperature for 2 hours and was acidified with 10 ml of 6N hydrochloric acid. The organic layer was separated, was dried over magnesium sulfate, and was concentrated to a crude solid which was suspended in chlorobutane/hexane and filtered to give 2.0 g of the title compound as a beige solid, m.p. 119°–124° C.

90 MHz NMR (CDCl$_3$)δ: 0.37 (s, 9H, SiH$_3$); 1.14 (s, 9H, C—CH$_3$); 1.43 (d, 3H, CH$_3$); 2.84–4.10 (m, 3H, CH, CH$_2$); 5.27 (s, 1H, NH); and 7.35 (d of d, 2H, arom).

EXAMPLE 5

2,3-Dihydro-6-methoxymethyl-2-methylbenzo[b]thiophene-7-sulfonamide

A mixture of N-t-butyl-2,3-dihydro-6-methylbenzo[b]thiophene-7-sulfonamide (7.4 g) and trifluoroacetic acid (100 ml) was stirred at room temperature for 15 hours. The reaction solution concentrated to an oil which was chromatographed on silica gel eluting with 45% ethyl acetate and 55% hexane to give 2.4 g of the title compound as a tan solid.

90 MHz NMR (CDCl$_3$)δ: 1.49 (d, 2H, CH$_3$); 3.53 (s, 3H, OCH$_3$); 2.87-3.97 (m, 3H, CH, CH$_2$); 4.80 (s, 2H, OCH$_2$); 5.47 (br s, 2H, NH$_2$); and 7.20 (d of d, 2H, arom).

EXAMPLE 6

2,3-Dihydro-6-methoxymethyl-2-methylbenzo[b]thiophene-7-sulfonamide-1,1-dioxide A mixture of 2,3-dihydro-6-methoxymethyl-2-methylbenzo[b]thiophene-7-sulfonamide (2.4 g), acetic acid (25 ml), and 30% hydrogen peroxide (10 ml) was heated at 85°-90° C. for 2 hours. The mixture was cooled to room temperature, poured into ice-water (125 ml), and extracted with ether-tetrahydrofuran (1:1). The organic extracts were washed with aqueous sodium bicarbonate until neutral, dried over magnesium sulfate, and concentrated to a residue which was washed with ether and filtered to give 1.3 g of the title compound as a pale yellow solid, m.p. 115° C. with decomposition.

90 MHz NMR (CDCl$_3$-DMSO)δ: 1.49 (d, 2H, CH$_3$); 3.48 (s, 3H, OCH$_3$); 2.5-3.8 (m, 3H, CH, CH$_2$); 4.92 (s, 2H, OCH$_2$); 6.7 (br s, 2H, NH$_2$); and 7.73 (d of d, 2H, arom).

EXAMPLE 7

2,3-Dihydro-2-methyl-6-trimethylsilylbenzo[b]thiophene-7-sulfonamide-1,1-dioxide A mixture of N-t-butyl-2,3-dihydro-2-methyl-6-trimethylsilylbenzo[b]thiophene-7-sulfonamide (2.2 g) and trifluoroacetic acid (40 ml) was stirred at ambient temperature for 2 hours. The reaction solution was concentrated to a crude residue which was dissolved in acetic acid (25 ml) and 30% hydrogen peroxide (10 ml) and heated at 80° to 90° C. for 2 hours. The cooled reaction mixture was poured into ice-water (150 ml) and stirred, giving, after filtration and drying, 0.7 g of the title compound as a white solid, m.p. 171°-172° C.

90 MHz NMR (CDCl$_3$)δ: 0.41 (s, 9H, SiCH$_3$); 1.54 (d, 3H, CH$_3$); 2.88-3.72 (m, 3H, CH$_2$); 5.67 (s, 2H, NH$_2$); and 7.78 (d of d, 2H, arom).

IR (nujol) 3300, 3200 cm$^{-1}$.

EXAMPLE 8

N-[(4-Methoxy-6-methylpyrimidin-2-yl)aminocarbonyl]-2,3-dihydro-2-methyl-6-methoxymethylbenzo[b]thiophene-7-sulfonamide-1,1-dioxide A solution of 2,3-dihydro-2-methyl-6-methoxymethylbenzo[b]thiophene-7-sulfonamide-1,1-dioxide (0.25 g) and of O-phenyl-N-(4-methoxy-6-methylpyrimidin-2-yl)carbamate (0.22 g) in 10 ml of dry dioxane was treated with 0.12 ml of 1,8-diazabicyclo[5.4.0]undec-7-ene. The solution was stirred at room temperature overnight, was diluted with water (25 ml), and was acidified with concentrated hydrochloric acid. The resulting precipitate was filtered, was washed with water and ether, and was air dried to give 0.17 g of the title compound as an off-white solid, m.p. 215°-216° C.

200 MHz NMR (CDCl$_3$)δ: 1.50 (d, 3H, CH$_3$); 2.45 (s, 3H, CH$_3$); 2.88-3.6 (m, 3H, CH, CH$_2$); 3.53 (s, 3H, OCH$_3$); 4.01 (s, 3H, OCH$_3$); 5.25 (d of d, 2H, OCH$_2$); 6.28 (s, 1H, CH); 7.48 (s, 1H, NH); 7.82 (d of d, 2H, arom); and 13.37 (s, 1H, NH).

IR(nujol) 1720 cm$^{-1}$.

EXAMPLE 9

N-[(4,6-Dimethoxypyrimidin-2-yl)aminocarbonyl]-2,3-dihydro-2-methyl-6-trimethylsilylbenzo[b]thiophene-7-sulfonamide-1,1-dioxide A solution of 2,3-dihydro-2-methyl-6-trimethylsilylbenzo[b]thiophene-7-sulfonamide-1,1-dioxide (0.23 g) and of O-phenyl-N-(4,6-dimethoxypyrimidin-2-yl)carbamate (0.21 g) in 10 ml of dry p-dioxane was treated with 0.11 ml of 1,8-diazabicyclo[5.4.0]undec-7-ene. The solution was stirred for 4 hours, was diluted with 25 ml of water, and was acidified with concentrated hydrochloric acid. The resulting precipitate was filtered, was washed with water and ether, and was air dried to give 0.25 g of the title compound as a white solid, m.p. 188°-190° C.

200 MHz NMR (CDCl$_3$)δ: 0.49 (s, 9H, SiCH$_3$); 1.48 (d, 3H, CH$_3$); 2.88-3.6 (m, 3H, CH, CH$_2$); 4.02 (s, 6H, OCH$_3$); 5.78 (s, 1H, CH); 7.25 (s, 1H, NH); 7.75 (d of d, 2H, arom); and 13.08 (s, 1H, NH).

IR(nujol) 1730 cm$^{-1}$.

Using the procedures of Examples 1 to 9 and the methods described herein, the following compounds in Tables I to VI can be prepared.

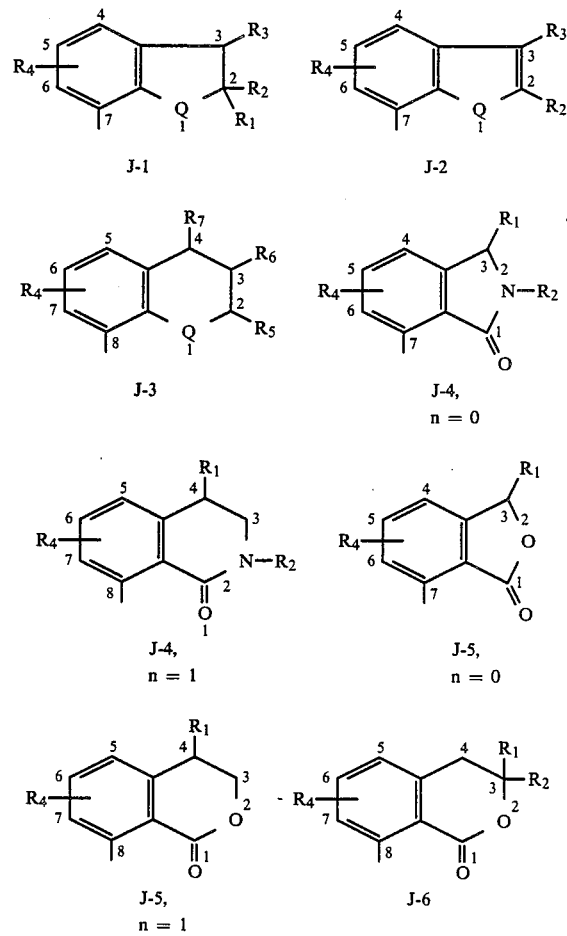

General Structures for Tables I-VIII

-continued
General Structures for Tables I-VIII

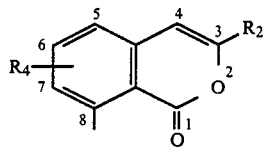
J-7

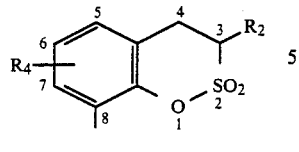
J-8

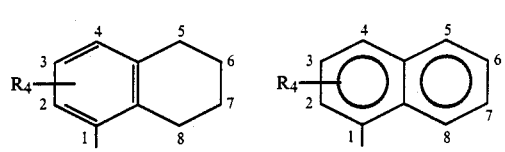
J-11, n = 1    J-12

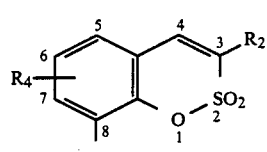
J-9

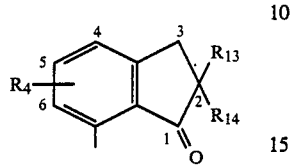
J-10, n = 0

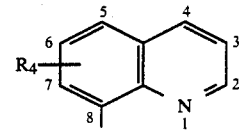
J-13

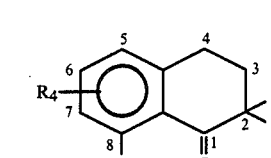
J-10, n = 1

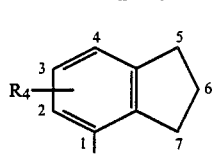
J-11, n = 0

TABLE I $$\text{JSO}_2\text{NHCNA} \overset{W}{\underset{R}{\|}}$$

J = J-1, A = A-1

| W | R | R₁ | R₂ | R₃ | R₄ | Q | X | Y | Z | m.p. (°C.) |
|---|---|----|----|----|-----|---|---|---|---|------------|
| O | H | H | H | H | 6-cyclopropyl | O | CH₃ | CH₃ | CH | |
| O | H | H | H | H | 6-cyclopropyl | O | OCH₃ | CH₃ | CH | |
| O | H | H | H | H | 6-Si(CH₃)₃ | O | OCH₃ | CH₃ | CH | |
| O | H | H | H | H | 6-Si(CH₃)₃ | S | OCH₃ | OCH₃ | N | |
| O | H | H | H | H | 6-CH₂OC₂H₅ | O | OCH₃ | CH₃ | N | |
| O | H | H | H | H | 6-CH₂OC₂H₅ | O | OCH₃ | CH₃ | CH | |
| O | H | H | H | H | 6-CH₂SO₂CH₃ | SO₂ | OCH₃ | CH₃ | N | |
| O | H | H | H | H | 6-CH₂SO₂CH₃ | SO₂ | OCH₃ | CH₃ | CH | |
| O | H | H | H | H | 5-(4'-ClC₆H₄) | S | CH₃ | CH₃ | CH | |
| O | H | H | H | H | 5-(4'-ClC₆H₄) | O | CH₃ | CH₃ | CH | |
| O | H | H | H | H | 5-CH₂OCH₃ | O | OCH₃ | OCH₃ | N | |
| O | H | H | H | H | 5-CH₂OCH₃ | SO₂ | CH₃ | OCH₃ | CH | |
| O | H | H | H | CH₃ | 5-CH₂OCH₃ | SO₂ | OCH₃ | OCH₃ | CH | |
| O | H | H | H | CH₃ | 5-CH₂OCH₃ | SO₂ | OCH₃ | OCH₃ | N | |
| O | H | H | H | CH₃ | 5-CH₂OCH₃ | SO₂ | CH₃ | OCH₃ | N | |
| O | H | H | H | CH₃ | 6-CH₂OCH₃ | SO₂ | CH₃ | OCH₃ | N | |
| O | H | H | H | CH₃ | 6-CH₂OCH₃ | SO₂ | CH₃ | OCH₃ | CH | |
| O | H | H | H | CH₃ | 6-CH₂OCH₃ | O | OCH₃ | OCH₃ | CH | |
| O | H | H | H | CH₃ | 6-CH₂SCH₃ | S | OCH₃ | OCH₃ | CH | |
| O | H | H | H | CH₃ | 6-CH₂SCH₃ | S | CH₃ | OCH₃ | CH | |
| O | H | H | H | CH₃ | 6-CH₂SCH₃ | O | CH₃ | OCH₃ | CH | |
| O | H | H | CH₃ | H | 5-CH₂OCH₃ | O | OCH₃ | OCH₃ | CH | |
| O | H | H | CH₃ | H | 5-CH₂OCH₂CH₃ | O | OCH₃ | OCH₃ | CH | |
| O | H | H | CH₃ | H | 5-CH₂CH₂OCH₃ | O | OCH₃ | OCH₃ | CH | |
| O | H | H | CH₃ | H | 5-Si(CH₃)₃ | O | OCH₃ | OCH₃ | CH | |
| O | H | H | CH₃ | H | 5-N(CH₃)₂ | O | OCH₃ | OCH₃ | CH | |
| O | H | H | CH₃ | H | 5-N(CH₃)₂ | S | OCH₃ | OCH₃ | CH | |
| O | H | H | CH₃ | H | 5-NH₂ | S | OCH₃ | OCH₃ | CH | |
| O | H | H | CH₃ | H | 5-CH₂CH₂OCH₂CH₃ | S | OCH₃ | OCH₃ | CH | |
| O | H | H | CH₃ | H | 5-CH₂CH₂OCH₃ | SO | OCH₃ | OCH₃ | CH | |
| O | H | H | CH₃ | H | 5-CH₂CN | SO | OCH₃ | OCH₃ | CH | |
| O | H | H | CH₃ | H | 5-CH₂SOCH₃ | SO | OCH₃ | OCH₃ | CH | |
| O | H | H | CH₃ | H | 5-NH₂ | SO₂ | OCH₃ | OCH₃ | CH | |
| O | H | H | CH₃ | H | 5-SO₂N(C₂H₅)₂ | SO₂ | OCH₃ | OCH₃ | CH | |
| O | H | H | CH₃ | H | 5-SO₂CH₃ | SO₂ | OCH₃ | OCH₃ | CH | |
| O | H | H | CH₃ | H | 5-SO₂CH₃ | SO₂ | CH₃ | OCH₃ | CH | |
| O | H | H | CH₃ | H | 5-SO₂CH₃ | SO₂ | CH₃ | OCH₃ | N | |
| O | H | H | CH₃ | H | 6-cyclopentyl | O | CH₃ | CH₃ | CH | |
| O | H | H | CH₃ | H | 6-cyclohexenyl | O | CH₃ | CH₃ | CH | |
| O | H | H | CH₃ | H | 6-(3'-BrC₆H₄) | O | CH₃ | CH₃ | CH | |
| O | H | H | CH₃ | H | 6-Si(CH₃)₃ | O | CH₃ | CH₃ | CH | |

TABLE I-continued $$\text{JSO}_2\text{NHCNA} \overset{\overset{W}{\|}}{\underset{R}{|}}$$

J = J-1, A = A-1

| W | R | R$_1$ | R$_2$ | R$_3$ | R$_4$ | Q | X | Y | Z | m.p. (°C.) |
|---|---|-------|-------|-------|-------|---|---|---|---|------------|
| O | H | H | CH$_3$ | H | 6-Si(CH$_3$)$_3$ | O | OCH$_3$ | CH$_3$ | CH | |
| O | H | H | CH$_3$ | H | 6-Si(CH$_3$)$_3$ | O | OCH$_3$ | OCH$_3$ | CH | |
| O | H | H | CH$_3$ | H | 6-Si(CH$_3$)$_3$ | O | Cl | OCH$_3$ | CH | |
| O | H | H | CH$_3$ | H | 6-Si(CH$_3$)$_3$ | O | OCH$_3$ | OCH$_3$ | N | |
| O | H | H | CH$_3$ | H | 6-Si(CH$_3$)$_3$ | O | CH$_3$ | OCH$_3$ | N | |
| O | H | H | CH$_3$ | H | 6-Si(CH$_3$)$_3$ | O | CH$_3$ | CH$_3$ | N | |
| O | H | H | CH$_3$ | H | 6-Si(CH$_3$)$_3$ | O | N(CH$_3$)$_2$ | CH$_3$ | N | |
| O | H | H | CH$_3$ | H | 6-Si(CH$_3$)$_3$ | O | NH(CH$_3$) | OCH$_3$ | N | |
| O | H | H | CH$_3$ | H | 6-Si(CH$_3$)$_3$ | O | NH(CH$_3$) | OC$_2$H$_7$ | N | |
| O | H | H | CH$_3$ | H | 6-Si(CH$_3$)$_3$ | O | OCF$_2$H | OC$_2$H$_7$ | CH | |
| O | H | H | CH$_3$ | H | 6-Si(CH$_3$)$_3$ | O | OCF$_3$ | OCF$_3$ | CH | |
| O | H | H | CH$_3$ | H | 6-Si(CH$_3$)$_3$(n-C$_4$H$_9$) | O | OCH$_3$ | OCH$_3$ | CH | |
| O | H | H | CH$_3$ | H | 6-Si(CH$_3$)$_2$OC$_2$H$_5$ | O | OCH$_3$ | OCH$_3$ | CH | |
| O | H | H | CH$_3$ | H | 6-Si(CH$_3$)$_2$C$_6$H$_5$ | O | OCH$_3$ | OCH$_3$ | CH | |
| O | H | H | CH$_3$ | H | 6-Si(CH$_3$)$_2$(2'-CH$_3$C$_6$H$_4$) | O | OCH$_3$ | OCH$_3$ | CH | |
| O | H | H | CH$_3$ | H | 6-P(O)(CH$_3$)$_2$ | O | OCH$_3$ | OCH$_3$ | CH | |
| O | H | H | CH$_3$ | H | 6-P(O)(OCH$_3$)$_2$ | O | OCH$_3$ | OCH$_3$ | CH | |
| O | H | H | CH$_3$ | H | 6-CN | O | OCH$_3$ | OCH$_3$ | CH | |
| O | H | H | CH$_3$ | H | 6-CN | O | CH$_3$ | OCH$_3$ | CH | |
| O | H | H | CH$_3$ | H | 6-CN | O | Cl | OCH$_3$ | CH | |
| O | H | H | CH$_3$ | H | 6-CN | O | CH$_3$ | CH$_3$ | N | |
| O | H | H | CH$_3$ | H | 6-CN | O | CH$_3$ | OCH$_3$ | N | |
| O | H | H | CH$_3$ | H | 6-CN | O | OCH$_3$ | OCH$_3$ | N | |
| O | H | H | CH$_3$ | H | 6-CN | O | OCH$_3$ | O—n-C$_3$H$_7$ | N | |
| O | H | H | CH$_3$ | H | 6-NH$_2$ | O | OCH$_3$ | OCH$_3$ | N | |
| O | H | H | CH$_3$ | H | 6-NH$_2$ | O | OCH$_3$ | CH$_3$ | N | |
| O | H | H | CH$_3$ | H | 6-NH$_2$ | O | CH$_3$ | CH$_3$ | CH | |
| O | H | H | CH$_3$ | H | 6-NH$_2$ | O | CH$_3$ | OCH$_3$ | CH | |
| O | H | H | CH$_3$ | H | 6-NH$_2$ | O | OCH$_3$ | OCH$_3$ | CH | |
| O | H | H | CH$_3$ | H | 6-NHCH$_3$ | O | OCH$_3$ | OCH$_3$ | CH | |
| O | H | H | CH$_3$ | H | 6-NHCH$_3$ | O | OCH$_3$ | CH$_3$ | N | |
| O | H | H | CH$_3$ | H | 6-N(C$_2$H$_5$)$_2$ | O | OCH$_3$ | CH$_3$ | N | |
| O | H | H | CH$_3$ | H | 6-NCH$_3$(n-C$_3$H$_7$) | O | OCH$_3$ | CH$_3$ | N | |
| O | H | H | CH$_3$ | H | 6-CH$_2$—cyclopropyl | O | OCH$_3$ | OCH$_3$ | CH | |
| O | H | H | CH$_3$ | H | 6-CH$_2$—cyclohexyl | O | OCH$_3$ | OCH$_3$ | CH | |
| O | H | H | CH$_3$ | H | 6-CH$_2$OC$_2$H$_5$ | O | OCH$_3$ | OCH$_3$ | CH | |
| O | H | H | CH$_3$ | H | 6-CH$_2$O—i-C$_3$H$_7$ | O | OCH$_3$ | OCH$_3$ | CH | |
| O | H | H | CH$_3$ | H | 6-CH$_2$OCF$_2$CF$_3$ | O | OCH$_3$ | OCH$_3$ | CH | |
| O | H | H | CH$_3$ | H | 6-CH$_2$OCH$_2$CH=CH$_2$ | O | OCH$_3$ | OCH$_3$ | CH | |
| O | H | H | CH$_3$ | H | 6-CH$_2$SCH$_3$ | O | OCH$_3$ | OCH$_3$ | CH | |
| O | H | H | CH$_3$ | H | 6-CH$_2$SCH$_3$ | O | CH$_3$ | OCH$_3$ | CH | |
| O | H | H | CH$_3$ | H | 6-CH$_2$SCH$_3$ | O | CH$_3$ | CH$_3$ | CH | |
| O | H | H | CH$_3$ | H | 6-CH$_2$SCH$_3$ | O | CH$_3$ | CH$_3$ | N | |
| O | H | H | CH$_3$ | H | 6-CH$_2$SCH$_3$ | O | CH$_3$ | OCH$_3$ | N | |
| O | H | H | CH$_3$ | H | 6-CH$_2$SCH$_3$ | O | OCH$_3$ | OCH$_3$ | N | |
| O | H | H | CH$_3$ | H | 6-CH$_2$SOC$_2$H$_5$ | O | OCH$_3$ | OCH$_3$ | N | |
| O | H | H | CH$_3$ | H | 6-CH$_2$SOCF$_3$ | O | OCH$_3$ | OCH$_3$ | N | |
| O | H | H | CH$_3$ | H | 6-CH$_2$SO$_2$CF$_3$ | O | OCH$_3$ | OCH$_3$ | N | |
| O | H | H | CH$_3$ | H | 6-C$_2$H$_4$SO$_2$CH$_3$ | O | OCH$_3$ | OCH$_3$ | N | |
| O | H | H | CH$_3$ | H | 6-C$_2$H$_4$SO$_2$CH$_3$ | O | CH$_3$ | OCH$_3$ | N | |
| O | H | H | CH$_3$ | H | 6-C$_2$H$_4$SO$_4$CH$_3$ | O | CH$_3$ | CH$_3$ | N | |
| O | H | H | CH$_3$ | H | 6-C$_2$H$_4$SO$_2$CH$_3$ | O | CH$_3$ | CH$_3$ | CH | |
| O | H | H | CH$_3$ | H | 6-C$_2$H$_4$SO$_2$CH$_3$ | O | CH$_3$ | OCH$_3$ | CH | |
| O | H | H | CH$_3$ | H | 6-C$_2$H$_4$SO$_2$CH$_3$ | O | OCH$_3$ | OCH$_3$ | CH | |
| O | H | H | CH$_3$ | H | 6-C$_2$H$_4$SO$_2$CH$_3$ | O | Cl | OCH$_3$ | CH | |
| O | H | H | CH$_3$ | H | 6-C$_2$H$_4$SO$_2$CH$_3$ | O | NHCH$_3$ | OC$_2$H$_5$ | N | |
| O | H | H | CH$_3$ | H | 6-CH$_2$CN | O | OCH$_3$ | OCH$_3$ | CH | |
| O | H | H | CH$_3$ | H | 6-N(CH$_3$)$_2$ | O | OCH$_3$ | OCH$_3$ | CH | |
| O | H | H | CH$_3$ | H | 6-cyclohexyl | S | OCH$_3$ | OCH$_3$ | CH | |
| O | H | H | CH$_3$ | H | 6-cyclopropyl | S | OCH$_3$ | OCH$_3$ | CH | |
| O | H | H | CH$_3$ | H | 6-cyclopropyl | S | OCH$_3$ | CH$_3$ | N | |
| O | H | H | CH$_3$ | H | 6-cyclohexenyl | S | OCH$_3$ | CH$_3$ | N | |
| O | H | H | CH$_3$ | H | 6-cyclohexenyl | S | OCH$_3$ | OCH$_3$ | CH | |
| O | H | H | CH$_3$ | H | 6-(4'-FC$_6$H$_4$) | S | OCH$_3$ | OCH$_3$ | CH | |
| O | H | H | CH$_3$ | H | 6-(4'-FC$_6$H$_4$) | S | CH$_3$ | OCH$_3$ | N | |
| O | H | H | CH$_3$ | H | 6-Si(CH$_3$)$_3$ | S | CH$_3$ | CH$_3$ | N | |
| O | H | H | CH$_3$ | H | 6-Si(CH$_3$)$_3$ | S | OCH$_3$ | CH$_3$ | N | |
| O | H | H | CH$_3$ | H | 6-Si(CH$_3$)$_3$ | S | OCH$_3$ | OC$_2$H$_5$ | N | |
| O | H | H | CH$_3$ | H | 6-Si(CH$_3$)$_3$ | S | NHCH$_3$ | OC$_2$H$_5$ | N | |
| O | H | H | CH$_3$ | H | 6-Si(CH$_3$)$_3$ | S | N(CH$_3$)$_2$ | N(CH$_3$)$_2$ | N | |
| O | H | H | CH$_3$ | H | 6-Si(CH$_3$)$_2$(4-BrC$_6$H$_4$) | S | OCH$_3$ | OCH$_3$ | CH | |
| O | H | H | CH$_3$ | H | 6-CN | S | OCH$_3$ | OCH$_3$ | CH | |
| O | H | H | CH$_3$ | H | 6-CN | S | CH$_3$ | CH$_3$ | N | |
| O | H | H | CH$_3$ | H | 6-P(O)(OCH$_3$)$_2$ | S | OCH$_3$ | CH$_3$ | N | |

TABLE I-continued $$JSO_2NHC(=W)NA-R$$

J = J-1, A = A-1

| W | R | R₁ | R₂ | R₃ | R₄ | Q | X | Y | Z | m.p. (°C.) |
|---|---|----|----|----|----|----|----|----|----|-----------|
| O | H | H | CH₃ | H | 6-P(O)(OCH₃)₂ | S | OCH₃ | OCH₃ | CH | |
| O | H | H | CH₃ | H | 6-CH₂OC₂H₅ | S | OCH₃ | OCH₃ | CH | |
| O | H | H | CH₃ | H | 6-CH₂OC₂H₅ | S | CH₃ | OCH₃ | N | |
| O | H | H | CH₃ | H | 6-CH₂OCH=CH₂ | S | CH₃ | OCH₃ | N | |
| O | H | H | CH₃ | H | 6-CH₂SCH₃ | S | CH₃ | OCH₃ | N | |
| O | H | H | CH₃ | H | 6-CH₂CH₂SO₂CH₃ | S | CH₃ | OCH₃ | N | |
| O | H | H | CH₃ | H | 6-CH₂CH₂SO₂CH₃ | S | OCH₃ | OCH₃ | CH | |
| O | H | H | CH₃ | H | 6-CH₂CH₂NO₂ | S | OCH₃ | OCH₃ | CH | |
| O | H | H | CH₃ | H | 6-cyclopropyl | SO | OCH₃ | OCH₃ | CH | |
| O | H | H | CH₃ | H | 6-cyclopropyl | SO | OCH₃ | CH₃ | N | |
| O | H | H | CH₃ | H | 6-cyclohexyl | SO | OCH₃ | CH₃ | N | |
| O | H | H | CH₃ | H | 6-cyclohexyl | SO | OCH₃ | OCH₃ | CH | |
| O | H | H | CH₃ | H | 6-cyclopenten-1-yl | SO | OCH₃ | OCH₃ | CH | |
| O | H | H | CH₃ | H | 6-cyclopenten-1-yl | SO | CH₃ | OCH₃ | N | |
| O | H | H | CH₃ | H | 6-OCH₃C₆H₄ | SO | CH₃ | OCH₃ | N | |
| O | H | H | CH₃ | H | 6-OCH₃C₆H₄ | SO | OCH₃ | OCH₃ | CH | |
| O | H | H | CH₃ | H | 6-Si(CH₃)₂C₂H₅ | SO | OCH₃ | OCH₃ | CH | |
| O | H | H | CH₃ | H | 6-Si(CH₃)₂C₂H₅ | SO | OCH₃ | CH₃ | N | |
| O | H | H | CH₃ | H | 6-Si(CH₃)₂CH₂CH=CH₂ | SO | OCH₃ | CH₃ | N | |
| O | H | H | CH₃ | H | 6-Si(CH₃)₂CH₂CH=CH₂ | SO | OCH₃ | OCH₃ | CH | |
| O | H | H | CH₃ | H | 6-Si(CH₃)₂OC₂H₅ | SO | OCH₃ | OCH₃ | CH | |
| O | H | H | CH₃ | H | 6-Si(CH₃)₂OC₂H₅ | SO | CH₃ | OCH₃ | N | |
| O | H | H | CH₃ | H | 6-N(CH₃)C₂H₅ | SO | CH₃ | OCH₃ | N | |
| O | H | H | CH₃ | H | 6-N(CH₃)C₂H₅ | SO | OCH₃ | OCH₃ | CH | |
| O | H | H | CH₃ | H | 6-pyrrolidin-1-yl | SO | OCH₃ | OCH₃ | CH | |
| O | H | H | CH₃ | H | 6-pyrrolidin-1-yl | SO | OCH₃ | CH₃ | N | |
| O | H | H | CH₃ | H | 6-CH₂—cyclopropyl | SO | OCH₃ | CH₃ | N | |
| O | H | H | CH₃ | H | 6-CH₂—cyclopropyl | SO | OCH₃ | OCH₃ | CH | |
| O | H | H | CH₃ | H | 6-CH₂OCH₃ | SO | OCH₃ | OCH₃ | CH | |
| O | H | H | CH₃ | H | 6-CH₂OCH₃ | SO | OCH₃ | OCH₃ | N | |
| O | H | H | CH₃ | H | 6-CH₂CH₂OCH₂CF₃ | SO | OCH₃ | OCH₃ | N | |
| O | H | H | CH₃ | H | 6-CH₂CH₂OCH₂CF₃ | SO | OCH₃ | OCH₃ | CH | |
| O | H | H | CH₃ | H | 6-CH₂OCF=CF₂ | SO | OCH₃ | OCH₃ | CH | |
| O | H | H | CH₃ | H | 6-CH₂SC₂H₅ | SO | OCH₃ | OCH₃ | CH | |
| O | H | H | CH₃ | H | 6-CH₂SCH₂CH₂F | SO | OCH₃ | OCH₃ | CH | |
| O | H | H | CH₃ | H | 6-CH₂SCH₂CH₂CH₂F | SO | OCH₃ | OCH₃ | CH | |
| O | H | H | CH₃ | H | 6-CH₂SOCH₃ | SO | OCH₃ | OCH₃ | CH | |
| O | H | H | CH₃ | H | 6-CH₂CH₂SOCH₃ | SO | OCH₃ | OCH₃ | CH | |
| O | H | H | CH₃ | H | 6-CH₂SO₂—i-C₃H₇ | SO | OCH₃ | OCH₃ | CH | |
| O | H | H | CH₃ | H | 6-CH₂CH₂SO₂CH₂CH₃ | SO | OCH₃ | OCH₃ | CH | |
| O | H | H | CH₃ | H | 6-CH₂Si(CH₃)₃ | SO | OCH₃ | OCH₃ | CH | |
| O | H | H | CH₃ | H | 6-CH₂Si(CH₃)₂—t-C₄H₉ | SO | OCH₃ | OCH₃ | CH | |
| O | H | H | CH₃ | H | 6-CH₂Si(CH₃)₂—t-C₄H₉ | SO | CH₃ | OCH₃ | N | |
| O | H | H | CH₃ | H | 6-CH₂CH₂NO₂ | SO | CH₃ | OCH₃ | N | |
| O | H | H | CH₃ | H | 6-CH₂CH₂CN | SO | CH₃ | OCH₃ | N | |
| O | H | H | CH₃ | H | 6-CH₂N(CH₃)₂ | SO | CH₃ | OCH₃ | N | |
| O | H | H | CH₃ | H | 6-CH₂N(CH₃)₂ | SO | OCH₃ | OCH₃ | CH | |
| O | H | H | CH₃ | H | 6-CH₂—N—morpholino | SO | OCH₃ | OCH₃ | CH | |
| O | H | H | CH₃ | H | 6-CH₂—N—morpholino | SO | OCH₃ | CH₃ | N | |
| O | H | H | CH₃ | H | 6-CH₂CH₂C(O)OCH₃ | SO | OCH₃ | CH₃ | N | |
| O | H | H | CH₃ | H | 6-CH₂SCN | SO | OCH₃ | CH₃ | N | |
| O | H | H | CH₃ | H | 6-CH₂PO(CH₃)₂ | SO | OCH₃ | CH₃ | N | |
| O | H | H | CH₃ | H | 6-CH₂PO(OCH₃)₂ | SO | OCH₃ | CH₃ | N | |
| O | H | H | CH₃ | H | 6-SO₂NHCH₃ | SO | OCH₃ | CH₃ | N | |
| O | H | H | CH₃ | H | 6-cyclopropyl | SO₂ | OCH₃ | OCH₃ | CH | |
| O | H | H | CH₃ | H | 6-cyclohexyl | SO₂ | OCH₃ | OCH₃ | CH | |
| O | H | H | CH₃ | H | 6-cyclohexen-1-yl | SO₂ | OCH₃ | OCH₃ | CH | |
| O | H | H | CH₃ | H | 6-(2'-FC₆H₄) | SO₂ | OCH₃ | OCH₃ | CH | |
| O | H | H | CH₃ | H | 6-(3'-CH₃C₆H₄) | SO₂ | OCH₃ | OCH₃ | CH | |
| O | H | H | CH₃ | H | 6-(3'-CH₃C₆H₄) | SO₂ | OCH₃ | OCH₃ | N | |
| O | H | H | CH₃ | H | 6-(4'-CH₃C₆H₄) | SO₂ | OCH₃ | OCH₃ | N | |
| O | H | H | CH₃ | H | 6-(4'-CH₃C₆H₄) | SO₂ | OCH₃ | OCH₃ | CH | |
| O | H | H | CH₃ | H | 6-Si(CH₃)₃ | SO₂ | CH₃ | OCH₃ | CH | |
| O | H | H | CH₃ | H | 6-Si(CH₃)₃ | SO₂ | n-C₄H₉ | OCH₃ | CH | |
| O | H | H | CH₃ | H | 6-Si(CH₃)₃ | SO₂ | OCH₃ | OCH₃ | CH | 188–190 |
| O | H | H | CH₃ | H | 6-Si(CH₃)₃ | SO₂ | OC₂H₅ | OCH₃ | CCH₃ | |
| O | H | H | CH₃ | H | 6-Si(CH₃)₃ | SO₂ | OCH₂CH₂F | OCH₃ | CH | |
| O | H | H | CH₃ | H | 6-Si(CH₃)₃ | SO₂ | CH₃ | OCH₃ | CCl | |
| O | H | H | CH₃ | H | 6-Si(CH₃)₃ | SO₂ | CF₂ | OCH₃ | CCl | |
| O | H | H | CH₃ | H | 6-Si(CH₃)₃ | SO₂ | CH₂CH₂CCl | OCH₃ | CCl | |
| O | H | H | CH₃ | H | 6-Si(CH₃)₃ | SO₂ | SCH₂CH₂F | OCH₃ | CH | |
| O | H | H | CH₃ | H | 6-Si(CH₃)₃ | SO₂ | SCH₂CH₂F | CH₃ | N | |
| O | H | H | CH₃ | H | 6-Si(CH₃)₃ | SO₂ | SCH₃ | CH₃ | N | |
| O | H | H | CH₃ | H | 6-Si(CH₃)₃ | SO₂ | S—i-C₃H₇ | CH₃ | N | |

TABLE I-continued $$\underset{\underset{R}{|}}{JSO_2NHCNA}\overset{\overset{W}{\|}}{}$$

J = J-1, A = A-1

| W | R | R₁ | R₂ | R₃ | R₄ | Q | X | Y | Z | m.p. (°C.) |
|---|---|---|---|---|---|---|---|---|---|---|
| O | H | H | CH₃ | H | 6-Si(CH₃)₃ | SO₂ | CH₃ | CH(OCH₃)₂ | CH | |
| O | H | H | CH₃ | H | 6-Si(CH₃)₃ | SO₂ | Cl | OCH₃ | CH | 212–214 |
| O | H | H | CH₃ | H | 6-Si(CH₃)₃ | SO₂ | Br | OCH₃ | CH | |
| O | H | H | CH₃ | H | 6-Si(CH₃)₃ | SO₂ | F | OCH₃ | CH | |
| O | H | H | CH₃ | H | 6-Si(CH₃)₃ | SO₂ | I | OCH₃ | CH | |
| O | H | H | CH₃ | H | 6-Si(CH₃)₃ | SO₂ | OC₂H₅ | NH₂ | CH | |
| O | H | H | CH₃ | H | 6-Si(CH₃)₃ | SO₂ | OC₂H₅ | dioxolan-2-yl | CH | |
| O | H | H | CH₃ | H | 6-Si(CH₃)₃ | SO₂ | OC₂H₅ | N(CH₃)₂ | CH | |
| O | H | H | CH₃ | H | 6-Si(CH₃)₃ | SO₂ | OC₂H₅ | OCH₂CH=CH₂ | CH | |
| O | H | H | CH₃ | H | 6-Si(CH₃)₃ | SO₂ | CH₃ | CH₃ | CH | |
| O | H | H | CH₃ | H | 6-Si(CH₃)₃ | SO₂ | CH₃ | CH₃ | N | |
| O | H | H | CH₃ | H | 6-Si(CH₃)₃ | SO₂ | CH₃ | OCH₃ | N | |
| O | H | H | CH₃ | H | 6-Si(CH₃)₃ | SO₂ | OCH₃ | OCH₃ | N | |
| O | H | H | CH₃ | H | 6-Si(CH₃)₃ | SO₂ | OCH₃ | CH₂OCH₃ | N | |
| O | H | H | CH₃ | H | 6-Si(CH₃)₃ | SO₂ | OCH₃ | OCH₂C≡CH | N | |
| O | H | H | CH₃ | H | 6-Si(CH₃)₃ | SO₂ | OCH₃ | C≡CH | N | |
| O | H | H | CH₃ | H | 6-Si(CH₃)₃ | SO₂ | OCH₃ | N₃ | N | |
| O | H | H | CH₃ | H | 6-Si(CH₃)₃ | SO₂ | OCH₃ | CN | N | |
| O | H | H | CH₃ | H | 6-Si(CH₃)₃ | SO₂ | OCH₃ | N(OCH₃)CH₃ | N | |
| O | H | H | CH₃ | H | 6-Si(CH₃)₂C₂H₅ | SO₂ | OCH₃ | CH₃ | N | |
| O | H | H | CH₃ | H | 6-Si(CH₃)₂C₂H₅ | SO₂ | OCH₃ | OCH₃ | N | |
| O | H | H | CH₃ | H | 6-Si(CH₃)₂OC₂H₅ | SO₂ | OCH₃ | CH₃ | N | |
| O | H | H | CH₃ | H | 6-Si(CH₃)₂OC₂H₅ | SO₂ | OCH₃ | OCH₃ | CH | |
| O | H | H | CH₃ | H | 6-PO(CH₃)₂ | SO₂ | OCH₃ | OCH₃ | CH | |
| O | H | H | CH₃ | H | 6-PO(CH₃)₂ | SO₂ | OCH₃ | CH₃ | CH | |
| O | H | H | CH₃ | H | 6-PO(OCH₃)₂ | SO₂ | OCH₃ | CH₃ | CH | |
| O | H | H | CH₃ | H | 6-PO(OCH₃)₂ | SO₂ | OCH₃ | CH₃ | N | |
| O | H | H | CH₃ | H | 6-CN | SO₂ | CH₃ | CH₃ | N | |
| O | H | H | CH₃ | H | 6-CN | SO₂ | OCH₃ | CH₃ | N | |
| O | H | H | CH₃ | H | 6-CN | SO₂ | OCH₃ | OCH₃ | N | |
| O | H | H | CH₃ | H | 6-CN | SO₂ | OCH₃ | OCH₃ | CH | 246–248 |
| O | H | H | CH₃ | H | 6-CN | SO₂ | CH₃ | OCH₃ | CH | 240–247 |
| O | H | H | CH₃ | H | 6-CN | SO₂ | Cl | OCH₃ | CH | 254–256 |
| O | H | H | CH₃ | H | 6-NH₂ | SO₂ | CH₃ | CH₃ | CH | |
| O | H | H | CH₃ | H | 6-NH₂ | SO₂ | CH₃ | OCH₃ | CH | |
| O | H | H | CH₃ | H | 6-NH₂ | SO₂ | OCH₃ | OCH₃ | CH | |
| O | H | H | CH₃ | H | 6-NH₂ | SO₂ | OCH₃ | OCH₃ | N | |
| O | H | H | CH₃ | H | 6-N(CH₃)₂ | SO₂ | OCH₃ | CH₃ | N | 138–139 dec. |
| O | H | H | CH₃ | H | 6-N(CH₃)₂ | SO₂ | OCH₃ | NHCH₃ | N | |
| O | H | H | CH₃ | H | 6-N(CH₃)₂ | SO₂ | CH₃ | CH₃ | CH | 188–192 |
| O | H | H | CH₃ | H | 6-N(CH₃)₂ | SO₂ | CH₃ | OCH₃ | CH | 191–194 |
| O | H | H | CH₃ | H | 6-N(CH₃)₂ | SO₂ | OCH₃ | OCH₃ | CH | 184–186 |
| O | H | H | CH₃ | H | 6-N(CH₃)₂ | SO₂ | Cl | OCH₃ | CH | 197–198 |
| O | H | H | CH₃ | H | 6-CH₂—cyclopropyl | SO₂ | OCH₃ | CH₃ | N | |
| O | H | H | CH₃ | H | 6-CH₂—cyclopropyl | SO₂ | OCH₃ | OCH₃ | CH | |
| O | H | H | CH₃ | H | 6-CH₂—cyclopropyl | SO₂ | CH₃ | OCH₃ | CH | |
| O | H | H | CH₃ | H | 6-CH₂—cyclopropyl | SO₂ | Cl | OCH₃ | CH | |
| O | H | H | CH₃ | H | 6-CH₂—cyclopentyl | SO₂ | CH₃ | OCH₃ | CH | |
| O | H | H | CH₃ | H | 6-CH₂OCH₃ | SO₂ | CH₃ | CH₃ | N | |
| O | H | H | CH₃ | H | 6-CH₂OCH₃ | SO₂ | OCH₃ | CH₃ | N | 184–186 |
| O | H | H | CH₃ | H | 6-CH₂OCH₃ | SO₂ | OCH₂CH₃ | NHCH₃ | N | |
| O | H | H | CH₃ | H | 6-CH₂OCH₃ | SO₂ | OCH₂CH₃ | N₃ | N | |
| O | H | H | CH₃ | H | 6-CH₂OCH₃ | SO₂ | OCH₂CH₃ | OCH₂CH=CH₂ | N | |
| O | H | H | CH₃ | H | 6-CH₂OCH₃ | SO₂ | OCH₂CH₃ | CH₂SCH₃ | N | |
| O | H | H | CH₃ | H | 6-CH₂OCH₃ | SO₂ | CH₂CH₃ | CF₃ | N | |
| O | H | H | CH₃ | H | 6-CH₂OCH₃ | SO₂ | OCH₂F | CH₃ | CH | |
| O | H | H | CH₃ | H | 6-CH₂OCH₃ | SO₂ | OCH₂CHF₂ | CH₃ | CH | |
| O | H | H | CH₃ | H | 6-CH₂OCH₃ | SO₂ | CH₂Cl | CH₃ | CH | |
| O | H | H | CH₃ | H | 6-CH₂OCH₃ | SO₂ | CH₃ | CH₃ | CH | |
| O | H | H | CH₃ | H | 6-CH₂OCH₃ | SO₂ | CH₃ | OCH₃ | CH | 215–216 |
| O | H | H | CH₃ | H | 6-CH₂OCH₃ | SO₂ | OCH₃ | OCH₃ | CH | 206–208 |
| O | H | H | CH₃ | H | 6-CH₂OCH₃ | SO₂ | Cl | OCH₃ | CH | 204–206 |
| O | H | H | CH₃ | H | 6-CH₂OCH₃ | SO₂ | OCH₃ | H | CH | |
| O | H | H | CH₃ | H | 6-CH₂OCH₃ | SO₂ | OCH₃ | CH₃ | CC₂H₅ | |
| O | H | H | CH₃ | H | 6-CH₂OCH₃ | SO₂ | OCH₃ | CH₃ | CBr | |
| O | H | H | CH₃ | H | 6-CH₂OCH₃ | SO₂ | CH₃ | SCH₃ | CH | |
| O | H | H | CH₃ | H | 6-CH₂OCH₃ | SO₂ | CH₃ | OCH₂CH₂OCH₃ | CH | |
| O | H | H | CH₃ | H | 6-CH₂OCH₃ | SO₂ | CH₃ | CH₂SCH₂CH₃ | CH | |
| O | H | H | CH₃ | H | 6-CH₂OCH₃ | SO₂ | CH₃ | CH₂OCH₃ | CH | |
| O | H | H | CH₃ | H | 6-CH₂OCH₃ | SO₂ | CH₃ | C(O)CH₃ | CH | |
| O | H | H | CH₃ | H | 6-CH₂OCH₃ | SO₂ | CH₃ | C(OCH₃)₂ | CH | |
| O | H | H | CH₃ | H | 6-CH₂CH₂OC₂H₅ | SO₂ | Cl | CH₃O | CH | |

TABLE I-continued $$\text{JSO}_2\text{NHCNA} \text{ with } W \text{ double-bonded to C, and R on N}$$

J = J-1, A = A-1

| W | R | $R_1$ | $R_2$ | $R_3$ | $R_4$ | Q | X | Y | Z | m.p. (°C.) |
|---|---|---|---|---|---|---|---|---|---|---|
| O | H | H | CH$_3$ | H | 6-CH$_2$CH$_2$OC$_2$H$_5$ | SO$_2$ | OCH$_3$ | CH$_3$O | CH | |
| O | H | H | CH$_3$ | H | 6-CH$_2$CH$_2$OC$_2$H$_5$ | SO$_2$ | CH$_3$ | CH$_3$O | CH | |
| O | H | H | CH$_3$ | H | 6-CH$_2$CH$_2$OC$_2$H$_5$ | SO$_2$ | CH$_3$ | CH$_3$ | N | |
| O | H | H | CH$_3$ | H | 6-CH$_2$CH$_2$OC$_2$H$_5$ | SO$_2$ | OCH$_3$ | CH$_3$ | N | |
| O | H | H | CH$_3$ | H | 6-CH$_2$CH$_2$OC$_2$H$_5$ | SO$_2$ | OCH$_3$ | OCH$_3$ | N | |
| O | H | H | CH$_3$ | H | 6-CH$_2$OCH$_2$CF$_3$ | SO$_2$ | OCH$_3$ | CH$_3$ | N | |
| O | H | H | CH$_3$ | H | 6-CH$_2$OCH$_2$CF$_3$ | SO$_2$ | OCH$_3$ | CH$_3$ | CH | |
| O | H | H | CH$_3$ | H | 6-CH$_2$CH$_2$OCH=CH$_2$ | SO$_2$ | OCH$_3$ | CH$_3$ | CH | |
| O | H | H | CH$_3$ | H | 6-CH$_2$CH$_2$OCH=CH$_2$ | SO$_2$ | OCH$_3$ | OCH$_3$ | N | |
| O | H | H | CH$_3$ | H | 6-CH$_2$OH | SO$_2$ | OCH$_3$ | OCH$_3$ | CH | 150–157 |
| O | H | H | CH$_3$ | H | 6-CH$_2$OH | SO$_2$ | OCH$_3$ | Cl | CH | 149–156 |
| O | H | H | CH$_3$ | H | 6-CH$_2$SCH$_3$ | SO$_2$ | OCH$_3$ | OCH$_3$ | N | |
| O | H | H | CH$_3$ | H | 6-CH$_2$SCH$_3$ | SO$_2$ | CH$_3$ | OCH$_3$ | N | |
| O | H | H | CH$_3$ | H | 6-CH$_2$SCH$_3$ | SO$_2$ | CH$_3$ | CH$_3$ | N | |
| O | H | H | CH$_3$ | H | 6-CH$_2$SCH$_3$ | SO$_2$ | CH$_3$ | CH$_3$ | CH | |
| O | H | H | CH$_3$ | H | 6-CH$_2$SCH$_3$ | SO$_2$ | CH$_3$ | OCH$_3$ | CH | |
| O | H | H | CH$_3$ | H | 6-CH$_2$SCH$_3$ | SO$_2$ | OCH$_3$ | OCH$_3$ | CH | |
| O | H | H | CH$_3$ | H | 6-CH$_2$SCH$_2$CF$_3$ | SO$_2$ | OCH$_3$ | OCH$_3$ | CH | |
| O | H | H | CH$_3$ | H | 6-CH$_2$S(O)CH$_3$ | SO$_2$ | OCH$_3$ | OCH$_3$ | CH | |
| O | H | H | CH$_3$ | H | 6-CH$_2$S(O)CH$_3$ | SO$_2$ | OCH$_3$ | OCH$_3$ | N | |
| O | H | H | CH$_3$ | H | 6-CH$_2$SO$_2$CH$_3$ | SO$_2$ | OCH$_3$ | OCH$_3$ | N | |
| O | H | H | CH$_3$ | H | 6-CH$_2$SO$_2$CH$_3$ | SO$_2$ | CH$_3$ | OCH$_3$ | N | |
| O | H | H | CH$_3$ | H | 6-CH$_2$SO$_2$CH$_3$ | SO$_2$ | CH$_3$ | CH$_3$ | N | |
| O | H | H | CH$_3$ | H | 6-CH$_2$SO$_2$CH$_3$ | SO$_2$ | CH$_3$ | CH$_3$ | CH | |
| O | H | H | CH$_3$ | H | 6-CH$_2$SO$_2$CH$_3$ | SO$_2$ | OCH$_3$ | CH$_3$ | CH | |
| O | H | H | CH$_3$ | H | 6-CH$_2$SO$_2$CH$_3$ | SO$_2$ | OCH$_3$ | OCH$_3$ | CH | |
| O | H | H | CH$_3$ | H | 6-CH$_2$CH$_2$SOCF$_2$H | SO$_2$ | OCH$_3$ | OCH$_3$ | CH | |
| O. | H | H | CH$_3$ | H | 6-CH$_2$CH$_2$SOCF$_2$H | SO$_2$ | OCH$_3$ | OCH$_3$ | N | |
| O | H | H | CH$_3$ | H | 6-CH$_2$CH$_2$SO$_2$CF$_2$H | SO$_2$ | OCH$_3$ | CH$_3$ | N | |
| O | H | H | CH$_3$ | H | 6-CH$_2$CH$_2$NO$_2$ | SO$_2$ | OCH$_3$ | CH$_3$ | CH | |
| O | H | H | CH$_3$ | H | 6-CH$_2$CN | SO$_2$ | OCH$_3$ | CH$_3$ | CH | 182–184 |
| O | H | H | CH$_3$ | H | 6-CH$_2$CN | SO$_2$ | OCH$_3$ | OCH$_3$ | CH | 207–209 |
| O | H | H | CH$_3$ | H | 6-CH$_2$CN | SO$_2$ | OCH$_3$ | Cl | CH | 185–187 |
| O | H | H | CH$_3$ | H | 6-CH$_2$CN | SO$_2$ | OCH$_3$ | CH$_3$ | N | 215–223 |
| O | H | H | CH$_3$ | H | 6-CH$_2$N(CH$_3$)$_2$ | SO$_2$ | OCH$_3$ | CH$_3$ | CH | |
| O | H | H | CH$_3$ | H | 6-CH$_2$N(CH$_3$)$_2$ | SO$_2$ | OCH$_3$ | OCH$_3$ | CH | |
| O | H | H | CH$_3$ | H | 6-CH$_2$N(CH$_3$)$_2$ | SO$_2$ | OCH$_3$ | OCH$_3$ | N | |
| O | H | H | CH$_3$ | H | 6-CH$_2$NH$_2$ | SO$_2$ | OCH$_3$ | CH$_3$ | CH | |
| O | H | H | CH$_3$ | H | 6-CH$_2$CO$_2$CH$_3$ | SO$_2$ | OCH$_3$ | CH$_3$ | CH | |
| O | H | H | CH$_3$ | H | 6-CH$_2$CO$_2$CH$_3$ | SO$_2$ | OCH$_3$ | CH$_3$ | N | |
| O | H | H | CH$_3$ | H | 6-CH$_2$SCN | SO$_2$ | OCH$_3$ | OCH$_3$ | CH | |
| O | H | H | CH$_3$ | H | 6-CH$_2$SCN | SO$_2$ | OCH$_3$ | CH$_3$ | N | |
| O | H | H | CH$_3$ | H | 6-P(O)(OCH$_3$)$_2$ | SO$_2$ | OCH$_3$ | CH$_3$ | N | |
| O | H | H | CH$_3$ | H | 6-P(O)(OCH$_3$)$_2$ | SO$_2$ | OCH$_3$ | CH$_3$ | CH | |
| O | H | H | CH$_3$ | H | 6-P(O)(CH$_3$)$_2$ | SO$_2$ | OCH$_3$ | CH$_3$ | CH | |
| O | H | H | CH$_3$ | H | 6-P(O)(CH$_3$)$_2$ | SO$_2$ | OCH$_3$ | OCH$_3$ | N | |
| O | H | H | CH$_3$ | H | 6-SO$_2$NHCH$_3$ | SO$_2$ | OCH$_3$ | OCH$_3$ | CH | |
| O | H | H | CH$_3$ | H | 6-SO$_2$N(CH$_3$)$_2$ | SO$_2$ | OCH$_3$ | OCH$_3$ | CH | |
| O | H | H | CH$_3$ | H | 6-SO$_2$N(CH$_3$)C$_2$H$_5$ | SO$_2$ | OCH$_3$ | OCH$_3$ | CH | |
| O | H | CH$_3$ | CH$_3$ | H | 5-CH$_2$SCH$_3$ | O | OCH$_3$ | OCH$_3$ | CH | |
| O | H | CH$_3$ | CH$_3$ | H | 5-N(CH$_3$)$_2$ | O | OCH$_3$ | OCH$_3$ | CH | |
| O | H | CH$_3$ | CH$_3$ | H | 5-CH$_2$OCH$_3$ | O | OCH$_3$ | OCH$_3$ | CH | |
| O | H | CH$_3$ | CH$_3$ | H | 6-CH$_2$OCH$_3$ | O | OCH$_3$ | OCH$_3$ | CH | |
| O | H | CH$_3$ | CH$_3$ | H | 6-CH$_2$CH$_2$OCH$_3$ | O | OCH$_3$ | OCH$_3$ | CH | |
| O | H | CH$_3$ | CH$_3$ | H | 6-NH$_2$ | O | OCH$_3$ | OCH$_3$ | CH | |
| O | H | CH$_3$ | CH$_3$ | H | 6-CH$_2$SO$_2$CH$_3$ | O | OCH$_3$ | OCH$_3$ | CH | |
| O | H | CH$_3$ | CH$_3$ | H | 6-Si(CH$_3$)$_3$ | O | OCH$_3$ | OCH$_3$ | CH | |
| O | H | CH$_3$ | CH$_3$ | H | 6-N—pyrrolidinyl | O | OCH$_3$ | OCH$_3$ | CH | |
| O | H | CH$_3$ | CH$_3$ | H | 6-CN | O | OCH$_3$ | OCH$_3$ | CH | |
| O | H | CH$_3$ | CH$_3$ | H | 6-P(O)(CH$_3$)$_2$ | O | OCH$_3$ | OCH$_3$ | CH | |
| O | H | CH$_3$ | CH$_3$ | H | 5-CH$_2$OCH$_2$CH$_3$ | S | OCH$_3$ | OCH$_3$ | CH | |
| O | H | CH$_3$ | CH$_3$ | H | 5-NH$_2$ | S | OCH$_3$ | OCH$_3$ | CH | |
| O | H | CH$_3$ | CH$_3$ | H | 5-NO$_2$ | S | OCH$_3$ | OCH$_3$ | CH | |
| O | H | CH$_3$ | CH$_3$ | H | 6-NO$_2$ | S | OCH$_3$ | OCH$_3$ | CH | |
| O | H | CH$_3$ | CH$_3$ | H | 6-CH$_2$OCH$_3$ | S | OCH$_3$ | OCH$_3$ | CH | |
| O | H | CH$_3$ | CH$_3$ | H | 6-CH$_2$Si(CH$_3$)$_3$ | S | OCH$_3$ | OCH$_3$ | CH | |
| O | H | CH$_3$ | CH$_3$ | H | 6-(4'-ClC$_6$H$_4$) | S | OCH$_3$ | OCH$_3$ | CH | |
| O | H | CH$_3$ | CH$_3$ | H | 5-CH$_2$CH$_2$OCH$_3$ | SO | OCH$_3$ | OCH$_3$ | CH | |
| O | H | CH$_3$ | CH$_3$ | H | 6-CH$_2$—cyclopropyl | SO | OCH$_3$ | OCH$_3$ | CH | |
| O | H | CH$_3$ | CH$_3$ | H | 6-CH$_2$SOCH$_3$ | SO | OCH$_3$ | OCH$_3$ | CH | |
| O | H | CH$_3$ | CH$_3$ | H | 5-CN | SO$_2$ | OCH$_3$ | OCH$_3$ | CH | |
| O | H | CH$_3$ | CH$_3$ | H | 5-CH$_2$OCH$_3$ | SO$_2$ | OCH$_3$ | OCH$_3$ | CH | |
| O | H | CH$_3$ | CH$_3$ | H | 5-CH$_2$CH$_2$SO$_2$CH$_3$ | SO$_2$ | OCH$_3$ | OCH$_3$ | CH | |

TABLE I-continued

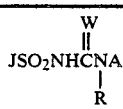

J = J-1, A = A-1

| W | R | R1 | R2 | R3 | R4 | Q | X | Y | Z | m.p. (°C.) |
|---|---|---|---|---|---|---|---|---|---|---|
| O | H | CH3 | CH3 | H | 6-Si(CH3)3 | SO2 | OCH3 | OCH3 | CH | |
| O | H | CH3 | CH3 | H | 6-Si(CH3)2OCH3 | SO2 | OCH3 | OCH3 | CH | |
| O | H | CH3 | CH3 | H | 6-CH2OC2H5 | SO2 | OCH3 | OCH3 | CH | |
| O | H | CH3 | CH3 | H | 6-CH2SO2C2H5 | SO2 | OCH3 | OCH3 | CH | |
| O | H | CH3 | H | CH3 | 6-CH2OCH3 | O | OCH3 | OCH3 | CH | |
| O | H | CH3 | H | CH3 | 6-CH2OCH3 | S | OCH3 | OCH3 | CH | |
| O | H | CH3 | H | CH3 | 6-CH2OCH3 | SO2 | OCH3 | OCH3 | CH | |
| O | H | CH3 | CH3 | CH3 | 6-CH2OCH3 | O | OCH3 | OCH3 | CH | |
| O | H | CH3 | CH3 | CH3 | 6-CH2OCH3 | SO | OCH3 | OCH3 | CH | |
| O | H | CH3 | CH3 | CH3 | 6-CH2OCH3 | SO2 | OCH3 | OCH3 | CH | |
| O | H | CH3 | C2H5 | CH3 | 6-CH2OCH3 | O | OCH3 | OCH3 | CH | |
| O | H | CH3 | C2H5 | CH3 | 6-CH2OCH3 | SO2 | OCH3 | OCH3 | CH | |
| O | H | H | C2H5 | CH3 | 6-CH2OCH3 | O | OCH3 | OCH3 | CH | |
| O | H | H | C2H5 | CH3 | 6-CH2OCH3 | SO2 | OCH3 | OCH3 | CH | |
| O | H | H | C2H5 | H | 6-CH2OCH3 | O | OCH3 | OCH3 | CH | |
| O | H | H | C2H5 | H | 6-CH2OCH3 | S | OCH3 | OCH3 | CH | |
| O | H | H | C2H5 | H | 6-CH2OCH3 | SO | OCH3 | OCH3 | CH | |
| O | H | H | C2H5 | H | 6-CH2OCH3 | SO2 | OCH3 | OCH3 | CH | |
| O | H | H | n-C3H7 | H | 6-CH2OCH3 | O | OCH3 | OCH3 | CH | |
| O | H | H | n-C3H7 | H | 6-CH2OCH3 | SO2 | OCH3 | OCH3 | CH | |
| O | H | H | n-C3H7 | CH3 | 6-CH2OCH3 | O | OCH3 | OCH3 | CH | |
| O | CH3 | H | CH3 | H | 6-CH2OCH3 | O | OCH3 | OCH3 | CH | |
| O | CH3 | H | CH3 | H | 6-CH2OCH3 | S | OCH3 | OCH3 | CH | |
| O | CH3 | H | CH3 | H | 6-CH2OCH3 | SO | OCH3 | OCH3 | CH | |
| O | CH3 | H | CH3 | H | 6-CH2OCH3 | SO2 | OCH3 | OCH3 | CH | |
| O | CH3 | CH3 | CH3 | H | 6-CH2OCH3 | O | OCH3 | OCH3 | CH | |
| O | CH3 | CH3 | CH3 | H | 6-CH2OCH3 | SO2 | OCH3 | OCH3 | CH | |
| S | H | H | H | H | 6-CH2OCH3 | O | OCH3 | OCH3 | CH | |
| S | H | H | H | H | 6-CH2OCH3 | SO2 | OCH3 | OCH3 | CH | |
| S | H | H | CH3 | H | 6-CH2OCH3 | O | OCH3 | OCH3 | CH | |
| S | H | H | CH3 | H | 6-CH2OCH3 | S | OCH3 | OCH3 | CH | |
| S | H | H | CH3 | H | 6-CH2OCH3 | SO2 | OCH3 | OCH3 | CH | |
| S | H | CH3 | CH3 | H | 6-CH2OCH3 | O | OCH3 | OCH3 | CH | |
| S | H | CH3 | CH3 | H | 6-CH2OCH3 | SO2 | OCH3 | OCH3 | CH | |
| S | H | CH3 | H | CH3 | 6-CH2OCH3 | O | OCH3 | OCH3 | CH | |
| S | CH3 | H | CH3 | H | 6-CH2OCH3 | SO3 | OCH3 | OCH3 | CH | |

TABLE II

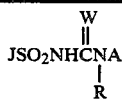

J = J-2, A = A-1

| W | R | R2 | R3 | R4 | Q | X | Y | Z | m.p. (°C.) |
|---|---|---|---|---|---|---|---|---|---|
| O | H | H | H | 6-CH2OCH3 | O | OCH3 | OCH3 | CH | |
| O | H | H | H | 6-CH2OCH3 | SO2 | OCH3 | CH3 | N | |
| O | H | H | CH3 | 6-CH2OCH3 | S | OCH3 | CH3 | CH | |
| O | H | CH3 | H | 5-CH2OCH3 | O | OCH3 | CH3 | CH | |
| O | H | CH3 | H | 5-CH2OCH2CH3 | S | OCH3 | OCF3 | CH | |
| O | H | CH3 | H | 5-CH2CH2OCH3 | SO2 | CH3 | OCH3 | N | |
| O | H | CH3 | H | 5-CH2CH2OCH3 | O | CH3 | C≡CH | N | |
| O | H | CH3 | H | 5-CH2CN2 | SO | OC2H5 | NHCH3 | N | |
| O | H | CH3 | H | 5-CH2CN2 | SO2 | Cl | OCH3 | CH | |
| O | H | CH3 | H | 5-CH2SCH3 | O | OCF2H | OCF2H | CH | |
| O | H | CH3 | H | 5-CH2SCH3CH3 | S | CH3 | SCH3 | CH | |
| O | H | CH3 | H | 5-CH2CH2SCH3 | SO2 | CH3 | OCH2CH=CH2 | CH | |
| O | H | CH3 | H | 5-NH2 | O | OCH2CF3 | OCH3 | CH | |
| O | H | CH3 | H | 5-N(CH3)2 | SO | CF3 | OCH3 | CH | |
| O | H | CH3 | H | 5-N(CH3)2 | SO2 | CH3 | OCH3 | N | |
| O | H | CH3 | H | 5-CN | S | OCH3 | OCH3 | N | |
| O | H | CH3 | H | 5-Si(CH3)3 | SO2 | OCH3 | OCH3 | CH | |
| O | H | CH3 | H | 6-cyclopropyl | O | OCH3 | OCH3 | CH | |
| O | H | CH3 | H | 6-(3'-ClC6H4) | SO | OCH3 | OCH3 | CH | |
| O | H | CH3 | H | 6-Si(CH3)3 | O | OCH3 | OCH3 | CH | |
| O | H | CH3 | H | 6-Si(CH3)3 | O | CH3 | OCH3 | CH | |
| O | H | CH3 | H | 6-Si(CH3)3 | O | CH3 | OCH3 | N | |
| O | H | CH3 | H | 6-Si(CH3)3 | O | CH3 | CN | CH | |
| O | H | CH3 | H | 6-Si(CH3)3 | S | CH3 | OCH3 | CH | |
| O | H | CH3 | H | 6-Si(CH3)3 | S | CH3 | OCH3 | N | |
| O | H | CH3 | H | 6-Si(CH3)3 | SO | OCH3 | C≡CH | N | |
| O | H | CH3 | H | 6-Si(CH3)3 | SO | CH3 | H | N | |

TABLE II-continued $$JSO_2NHCNA$$
with W (double bond to C), R on N
J = J-2, A = A-1

| W | R | R₂ | R₃ | R₄ | Q | X | Y | Z | m.p. (°C.) |
|---|---|----|----|----|---|---|---|---|------------|
| O | H | CH₃ | H | 6-Si(CH₃)₃ | SO₂ | CH₃ | OCH₃ | N | |
| O | H | CH₃ | H | 6-Si(CH₃)₃ | SO₂ | CH₃ | OCH₃ | CH | |
| O | H | CH₃ | H | 6-Si(CH₃)₃ | SO₂ | Cl | OCH₃ | CH | |
| O | H | CH₃ | H | 6-Si(CH₃)₃ | SO₂ | OC₂H₅ | NHCH₃ | N | |
| O | H | CH₃ | H | 6-Si(CH₃)₂—t-C₄H₉ | O | OCH₃ | OCH₃ | CH | |
| O | H | CH₃ | H | 6-Si(CH₃)₂OCH₂CH₃ | SO₂ | OCH₃ | OCH₃ | CH | |
| O | H | CH₃ | H | 6-P(O)(CH₃)₂ | SO | OCH₃ | OCH₃ | CH | |
| O | H | CH₃ | H | 6-CN | O | OCH₃ | OCH₃ | CH | |
| O | H | CH₃ | H | 6-CN | S | OCH₃ | OCH₃ | CH | |
| O | H | CH₃ | H | 6-CN | 2 | OCH₃ | OCH₃ | CH | |
| O | H | CH₃ | H | 6-NH₂ | O | OCH₃ | OCH₃ | CH | |
| O | H | CH₃ | H | 6-NHCH₃ | S | OCH₃ | OCH₃ | CH | |
| O | H | CH₃ | H | 6-N(CH₃)₂ | O | OCH₃ | CH₃ | N | |
| O | H | CH₃ | H | 6-N(CH₃)₂ | SO | OCH₃ | CH₃ | CH | |
| O | H | CH₃ | H | 6-N(CH₃)₂ | SO₂ | OCH₃ | CH₃ | CH | |
| O | H | CH₃ | H | 6-CH₂OCH₃ | O | OCH₃ | OCH₃ | CH | |
| O | H | CH₃ | H | 6-CH₂OCH₃ | O | CH₃ | OCH₃ | CH | |
| O | H | CH₃ | H | 6-CH₂OCH₃ | O | CH₃ | OCH₃ | N | |
| O | H | CH₃ | H | 6-CH₂OCH₃ | O | OC₂H₅ | NHCH₃ | N | |
| O | H | CH₃ | H | 6-CH₂OCH₃ | S | OCH₃ | CH₃ | CH | |
| O | H | CH₃ | H | 6-CH₂OCH₃ | S | OCH₃ | CH₃ | N | |
| O | H | CH₃ | H | 6-CH₂OCH₃ | SO | OCH₃ | CH₃ | CH | |
| O | H | CH₃ | H | 6-CH₂OCH₃ | SO | OCH₃ | OCH₃ | CH | |
| O | H | CH₃ | H | 6-CH₂OCH₃ | SO₂ | OCH₃ | OCH₃ | CH | |
| O | H | CH₃ | H | 6-CH₂OCH₃ | SO₂ | OCH₃ | CH₃ | CH | |
| O | H | CH₃ | H | 6-CH₂OCH₃ | SO₂ | OCH₃ | CH₃ | N | |
| O | H | CH₃ | H | 6-CH₂OCH₃ | SO₂ | OCH₃ | C≡CH | N | |
| O | H | CH₃ | H | 6-CH₂CH₂OCH₂CF₃ | SO₂ | CH₃ | OCH₃ | CH | |
| O | H | CH₃ | H | 6-CH₂SCH₃ | O | OCH₃ | OCH₃ | CH | |
| O | H | CH₃ | H | 6-CH₂SCH₃ | S | OCH₃ | OCH₃ | CH | |
| O | H | CH₃ | H | 6-CH₂SCH₃ | SO₂ | OCH₃ | OCH₃ | CH | |
| O | H | CH₃ | H | 6-CH₂CH₂SO₂CH₃ | SO₂ | OCH₃ | OCH₃ | CH | |
| O | H | CH₃ | H | 6-CH₂CN | O | OCH₃ | OCH₃ | CH | |
| O | H | CH₃ | H | 6-CH₂CH₂COCH₂CH₃ | S | OCH₃ | OCH₃ | CH | |
| O | H | CH₃ | H | 6-CH₂N(CH₃)₂ | SO₂ | OCH₃ | OCH₃ | CH | |
| O | H | CH₃ | CH₃ | 6-CH₂OCH₃ | O | OCH₃ | OCH₃ | CH | |
| O | H | CH₃ | CH₃ | 6-Si(CH₃)₃ | O | OCH₃ | OCH₃ | CH | |
| O | H | CH₃ | CH₃ | 6-CH₂CN | S | OCH₃ | OCH₃ | CH | |
| O | H | CH₃ | CH₃ | 6-CH₂CH₂OCH₃ | SO | OCH₃ | OCH₃ | CH | |
| O | H | CH₃ | CH₃ | 6-CH₂SO₂CH₃ | SO₂ | OCH₃ | OCH₃ | CH | |
| O | H | CH₃ | CH₃ | 6-CH₂N(CH₃)₂ | SO₂ | OCH₃ | OCH₃ | CH | |
| O | H | CH₃ | CH₃ | 6-CH₂OCH₂CH₃ | O | OCH₃ | OCH₃ | CH | |
| O | H | CH₃ | CH₃ | 6-CH₂OCH₃ | SO₂ | OCH₃ | OCH₃ | CH | |
| O | CH₃ | CH₃ | H | 6-CH₂OCH₃ | O | OCH₃ | OCH₃ | CH | |
| O | CH₃ | CH₃ | H | 6-CH₂OCH₃ | SO₂ | OCH₃ | OCH₃ | CH | |
| S | H | CH₃ | H | 6-CH₂OCH₃ | O | OCH₃ | OCH₃ | CH | |
| S | H | CH₃ | H | 6-CH₂OCH₃ | SO₂ | OCH₃ | OCH₃ | CH | |

TABLE III $$JSO_2NHCNA$$
with W (double bond to C), R on N
J = J-3, A = A-1

| W | R | R₅ | R₂ | R₃ | R₄ | Q | X | Y | Z | m.p. (°C.) |
|---|---|----|----|----|----|---|---|---|---|------------|
| O | H | H | H | H | 7-CH₂OCH₃ | O | OCH₃ | OCH₃ | CH | |
| O | H | H | H | H | 7-CH₂OCH₃ | SO₂ | OCH₃ | CH₃ | N | |
| O | H | H | CH₃ | H | 7-CH₂OCH₃ | S | OCH₃ | CH₃ | CH | |
| O | H | H | H | H | 6-CH₂OCH₃ | O | OCH₃ | CH₃ | CH | |
| O | H | H | H | H | 6-CH₂OCH₂CH₃ | S | OCH₃ | OCF₃ | CH | |
| O | H | H | H | H | 6-CH₂CH₂OCH₃ | SO₂ | CH₃ | OCH₃ | N | |
| O | H | H | H | H | 6-CH₂CH₂OCH₃ | O | CH₃ | C≡CH | N | |
| O | H | H | H | H | 6-CH₂CN₂ | SO | OC₂H₅ | NHCH₃ | N | |
| O | H | H | H | H | 6-CH₂CN₂ | SO₂ | Cl | OCH₃ | CH | |
| O | H | H | H | H | 6-CH₂SCH₃ | O | OCF₂H | OCF₂H | CH | |
| O | H | H | H | H | 6-CH₂SCH₃CH₃ | S | CH₃ | SCH₃ | CH | |
| O | H | H | H | H | 6-CH₂CH₂SCH₃ | SO₂ | CH₃ | OCH₂CH=CH₂ | CH | |
| O | H | H | H | H | 6-NH₂ | O | OCH₂CF₃ | OCH₃ | CH | |
| O | H | H | H | H | 6-N(CH₃)₂ | SO | CF₃ | OCH₃ | CH | |
| O | H | H | H | H | 6-N(CH₃)₂ | SO₂ | CH₃ | OCH₃ | N | |
| O | H | H | H | H | 6-CN | S | OCH₃ | OCH₃ | N | |
| O | H | H | H | H | 6-Si(CH₃)₃ | SO₂ | OCH₃ | OCH₃ | CH | |

TABLE III-continued $$\underset{R}{\underset{|}{JSO_2NHCNA}}\overset{\overset{W}{\|}}{{}}$$

J = J-3, A = A-1

| W | R | R5 | R2 | R3 | R4 | Q | X | Y | Z | m.p. (°C.) |
|---|---|---|---|---|---|---|---|---|---|---|
| O | H | H | H | H | 7-cyclopropyl | O | OCH3 | OCH3 | CH | |
| O | H | H | H | H | 7-(3'-ClC6H4) | SO | OCH3 | OCH3 | CH | |
| O | H | H | H | H | 7-Si(CH3)3 | O | OCH3 | OCH3 | CH | |
| O | H | H | H | H | 7-Si(CH3)3 | O | CH3 | OCH3 | CH | |
| O | H | H | H | H | 7-Si(CH3)3 | O | CH3 | OCH3 | N | |
| O | H | H | H | H | 7-Si(CH3)3 | O | CH3 | CN | CH | |
| O | H | H | H | H | 7-Si(CH3)3 | S | CH3 | OCH3 | CH | |
| O | H | H | H | H | 7-Si(CH3)3 | S | CH3 | OCH3 | N | |
| O | H | H | H | H | 7-Si(CH3)3 | SO | OCH3 | C≡CH | N | |
| O | H | H | H | H | 7-Si(CH3)3 | SO | CH3 | H | N | |
| O | H | H | H | H | 7-Si(CH3)3 | SO2 | CH3 | OCH3 | N | |
| O | H | H | H | H | 7-Si(CH3)3 | SO2 | CH3 | OCH3 | CH | |
| O | H | H | H | H | 7-Si(CH3)3 | SO2 | Cl | OCH3 | CH | |
| O | H | H | H | H | 7-Si(CH3)3 | SO2 | OC2H5 | NHCH3 | N | |
| O | H | H | H | H | 7-Si(CH3)2—t-C4H9 | O | OCH3 | OCH3 | CH | |
| O | H | H | H | H | 7-Si(CH3)2OCH2CH3 | SO2 | OCH3 | OCH3 | CH | |
| O | H | H | H | H | 7-P(O)(CH3)2 | SO | OCH3 | OCH3 | CH | |
| O | H | H | H | H | 7-CN | O | OCH3 | OCH3 | CH | |
| O | H | H | H | H | 7-CN | S | OCH3 | OCH3 | CH | |
| O | H | H | H | H | 7-NH2 | O | OCH3 | OCH3 | CH | |
| O | H | H | H | H | 7-NHCH3 | S | OCH3 | OCH3 | CH | |
| O | H | H | H | H | 7-N(CH3)2 | O | OCH3 | CH3 | N | |
| O | H | H | H | H | 7-N(CH3)2 | SO | OCH3 | CH3 | CH | |
| O | H | H | H | H | 7-N(CH3)2 | SO2 | OCH3 | CH3 | CH | |
| O | H | H | H | H | 7-CH2OCH3 | O | OCH3 | OCH3 | CH | |
| O | H | H | H | H | 7-CH2OCH3 | O | CH3 | OCH3 | CH | |
| O | H | H | H | H | 7-CH2OCH3 | O | CH3 | OCH3 | N | |
| O | H | H | H | H | 7-CH2OCH3 | O | OC2H5 | NHCH3 | N | |
| O | H | H | H | H | 7-CH2OCH3 | S | OCH3 | CH3 | CH | |
| O | H | H | H | H | 7-CH2OCH3 | S | OCH3 | CH3 | N | |
| O | H | H | H | H | 7-CH2OCH3 | SO | OCH3 | CH3 | CH | |
| O | H | H | H | H | 7-CH2OCH3 | SO | OCH3 | OCH3 | CH | |
| O | H | H | H | H | 7-CH2OCH3 | SO2 | OCH3 | OCH3 | CH | |
| O | H | H | H | H | 7-CH2OCH3 | SO2 | OCH3 | CH3 | CH | |
| O | H | H | H | H | 7-CH2OCH3 | SO2 | OCH3 | CH3 | N | |
| O | H | H | H | H | 7-CH2OCH3 | SO2 | OCH3 | C≡CH | N | |
| O | H | H | H | H | 7-CH2CH2OCH2CF3 | SO2 | CH3 | OCH3 | CH | |
| O | H | H | H | H | 7-CH2SCH3 | O | OCH3 | OCH3 | CH | |
| O | H | H | H | H | 7-CH2SCH3 | S | OCH3 | OCH3 | CH | |
| O | H | H | H | H | 7-CH2SCH3 | SO2 | OCH3 | OCH3 | CH | |
| O | H | H | H | H | 7-CH2CH2SO2CH3 | SO2 | OCH3 | OCH3 | CH | |
| O | H | H | H | H | 7-CH2CN | O | OCH3 | OCH3 | CH | |
| O | H | H | H | H | 7-CH2CH2COCH2CH3 | S | OCH3 | OCH3 | CH | |
| O | H | H | H | H | 7-CH2N(CH3)2 | SO2 | OCH3 | OCH3 | CH | |
| O | H | H | CH3 | H | 7-CH2OCH3 | O | OCH3 | OCH3 | CH | |
| O | H | H | CH3 | H | 7-Si(CH3)3 | O | OCH3 | OCH3 | CH | |
| O | H | CH3 | CH3 | H | 7-CH2CN | S | OCH3 | OCH3 | CH | |
| O | H | CH3 | CH3 | H | 7-CH2CH2OCH3 | SO | OCH3 | OCH3 | CH | |
| O | H | CH3 | CH3 | H | 7-CH2SO2CH3 | SO2 | OCH3 | OCH3 | CH | |
| O | H | CH3 | CH3 | H | 7-CH2N(CH3)2 | SO2 | OCH3 | OCH3 | CH | |
| O | H | CH3 | CH3 | CH3 | 7-CH2OCH2CH3 | O | OCH3 | OCH3 | CH | |
| O | H | CH3 | CH3 | CH3 | 7-CH2OCH3 | SO2 | OCH3 | OCH3 | CH | |
| O | CH3 | CH3 | H | H | 7-CH2OCH3 | O | OCH3 | OCH3 | CH | |
| O | CH3 | CH3 | H | H | 7-CH2OCH3 | SO2 | OCH3 | OCH3 | CH | |
| S | H | CH3 | H | H | 7-CH2OCH3 | O | OCH3 | OCH3 | CH | |
| S | H | CH3 | H | H | 7-CH2OCH3 | SO2 | OCH3 | OCH3 | CH | |

TABLE IV $$\underset{R}{\underset{|}{JSO_2NHCNA}}\overset{\overset{W}{\|}}{{}}$$

J = J-1

| W | R | R1 | R2 | R3 | R4 | Q | A | X1 | Y1 | m.p. (°C.) |
|---|---|---|---|---|---|---|---|---|---|---|
| O | H | H | H | H | 6-Si(CH3)3 | O | A-2 | OCF2H | O | |
| O | H | H | CH3 | H | 5-CH2CN | O | A-2 | CH3 | O | |
| O | H | H | CH3 | H | 5-N(CH3)2 | SO2 | A-2 | OCH3 | CH2 | |
| O | H | H | CH3 | H | 5-CH2CH2OCH3 | S | A-2 | CH3 | O | |
| O | H | H | CH3 | H | 6-C6H4—3-SCH3 | S | A-2 | OC2H5 | CH2 | |
| O | H | H | CH3 | H | 6-Si(CH3)3 | SO2 | A-2 | OCH3 | CH2 | |
| O | H | H | CH3 | H | 6-Si(CH3)3 | O | A-2 | CH3 | CH2 | |

TABLE IV-continued $$\text{JSO}_2\text{NHCNA} \overset{\overset{W}{\|}}{\underset{R}{|}}$$

J = J-1

| W | R | R₁ | R₂ | R₃ | R₄ | Q | A | X₁ | Y₃ | m.p. (°C.) |
|---|---|----|----|----|-----|---|---|----|----|-----------|
| O | H | H | CH₃ | H | 6-Si(CH₃)₃ | SO | A-2 | CH₃ | O | |
| O | H | H | CH₃ | H | 6-PO(CH₃)₃ | SO₂ | A-2 | OCH₃ | O | |
| O | H | H | CH₃ | H | 6-CN | SO₂ | A-2 | OCF₂H | O | |
| O | H | H | CH₃ | H | 6-CN | O | A-2 | OCF₂H | CH₂ | |
| O | H | H | CH₃ | H | 6-NH₂ | O | A-2 | OC₂H₅ | O | |
| O | H | H | CH₃ | H | 6-CH₂CH₂OCH₃ | SO | A-2 | OCH₃ | O | |
| O | H | H | CH₃ | H | 6-CH₂SCH₃ | S | A-2 | CH₃ | CH₂ | |
| O | H | CH₃ | CH₃ | H | 6-CH₂OCH₃ | SO₂ | A-2 | CH₃ | CH₂ | |
| O | H | H | C₂H₅ | H | 6-CH₂OCH₃ | SO₂ | A-2 | OCH₃ | CH₂ | |
| O | H | H | CH₃ | CH₃ | 6-CH₂OCH₃ | O | A-2 | OCH₃ | O | |
| O | H | CH₃ | CH₃ | CH₃ | 6-CH₂OCH₃ | SO₂ | A-2 | OCF₂H | CH₂ | |
| O | CH₃ | H | CH₃ | H | 6-CH₂OCH₃ | SO₂ | A-2 | OCH₃ | O | |
| S | H | H | CH₃ | H | 6-CH₂OCH₃ | SO₂ | A-2 | CH₃ | O | |
| O | H | H | H | H | 6-CH₂OCH₂CF₃ | SO₂ | A-3 | OCH₃ | | |
| O | H | H | CH₃ | H | 6-CH₂CH₂SCH₃ | S | A-3 | OCH₃ | | |
| O | H | H | CH₃ | H | 6-NH₂ | SO₂ | A-3 | CH₃ | | |
| O | H | H | CH₃ | H | 5-CH₂OC₂H₅ | O | A-3 | OCF₂H | | |
| O | H | H | CH₃ | H | 6-cyclopropyl | O | A-3 | OCH₃ | | |
| O | H | H | CH₃ | H | 6-(2'-FC₆H₄) | O | A-3 | CH₃ | | |
| O | H | H | CH₃ | H | 6-CN | S | A-3 | OC₂H₅ | | |
| O | H | H | CH₃ | H | 6-CN | SO₂ | A-3 | OCF₂H | | |
| O | H | H | CH₃ | H | 6-N(CH₃)₂ | O | A-3 | OCH₃ | | |
| O | H | H | CH₃ | H | 6-CH₂OCH₃ | O | A-3 | CH₃ | | |
| O | H | H | CH₃ | H | 6-CH₂OCH₃ | SO₂ | A-3 | CH₃ | | |
| O | H | H | CH₃ | H | 6-CH₂OCH₃ | S | A-3 | OCH₃ | | |
| O | H | H | CH₃ | H | 6-Si(CH₃)₃ | O | A-3 | OCH₃ | | |
| O | H | H | CH₃ | H | 6-Si(CH₃)₃ | SO | A-3 | OC₂H₅ | | |
| O | H | H | CH₃ | H | 6-Si(CH₃)₃ | SO₂ | A-3 | CH₃ | | |
| O | H | H | C₂H₅ | H | 6-Si(CH₃)₃ | O | A-3 | CH₃ | | |
| O | H | H | CH₃ | CH₃ | 6-Si(CH₃)₃ | O | A-3 | OCH₃ | | |
| O | H | CH₃ | CH₃ | CH₃ | 6-Si(CH₃)₃ | SO₂ | A-3 | CH₃ | | |
| O | H | CH₃ | H | CH₃ | 6-Si(CH₃)₃ | O | A-3 | CH₃ | | |
| S | H | H | CH₃ | H | 6-Si(CH₃)₃ | O | A-3 | CH₃ | | |

| W | R | R₁ | R₂ | R₃ | R₄ | Q | A | X₁ | Y₃ | m.p. (°C.) |
|---|---|----|----|----|-----|---|---|----|----|-----------|
| O | H | H | H | H | 6-Si(CH₃)₃ | SO₂ | A-4 | CH₃ | CH₃ | |
| O | H | H | CH₃ | H | 5-CH₂OCH₃ | O | A-4 | OCH₃ | CH₃ | |
| O | H | H | CH₃ | H | 5-CH₂CH₂CN | S | A-4 | OCH₃ | H | |
| O | H | H | CH₃ | H | 6-Si(CH₃)₃ | SO | A-4 | OCF₂H | H | |
| O | H | H | CH₃ | H | 6-Si(CH₃)₃ | SO₂ | A-4 | OCH₃ | H | |
| O | H | H | CH₃ | H | 6-CH₂OCH₃ | O | A-4 | OC₂H₅ | CH₃ | |
| O | H | H | CH₃ | H | 6-CH₂OCH₃ | S | A-4 | OCH₃ | CH₃ | |
| O | H | H | CH₃ | H | 6-CH₂OCH₃ | SO₂ | A-4 | CH₃ | CH₃ | |
| O | H | H | CH₃ | H | 6-CH₂CN | O | A-4 | OCH₃ | CH₃ | |
| O | H | H | CH₃ | H | 6-CH₂CN | SO₂ | A-4 | OCF₂H | CH₃ | |
| O | H | H | CH₃ | H | 6-CH₂SCH₃ | S | A-4 | CH₃ | H | |
| O | H | H | CH₃ | H | 6-CH₂CH₂NO₂ | O | A-4 | CH₃ | H | |
| O | H | H | CH₃ | H | 6-CH₂SO₂CH₃ | SO₂ | A-4 | OCH₃ | CH₃ | |
| O | H | H | CH₃ | H | 6-CH₂NO₂ | O | A-4 | CH₃ | CH₃ | |
| O | H | H | CH₃ | C₂H₅ | 6-CH₂CH₂OCH₃ | O | A-4 | OCH₃ | H | |
| O | H | CH₃ | CH₃ | H | 6-CH₂CH₂OCH₃ | SO₂ | A-4 | CH₃ | H | |
| O | H | H | CH₃ | CH₃ | 6-CH₂CH₂OCH₃ | SO₂ | A-4 | OCF₂H | H | |
| O | H | CH₃ | CH₃ | CH₃ | 6-CH₂CH₂OCH₃ | SO₂ | A-4 | CH₃ | H | |
| O | CH₃ | H | CH₃ | H | 6-CH₂CH₂OCH₃ | SO₂ | A-4 | CH₃ | H | |
| S | H | H | CH₃ | H | 6-CH₂CH₂OCH₃ | SO₂ | A-4 | CH₃ | H | |

| W | R | R₁ | R₂ | R₃ | R₄ | Q | A | X₂ | Y₂ | m.p. (°C.) |
|---|---|----|----|----|-----|---|---|----|----|-----------|
| O | H | H | H | H | 6-CH₂CN | O | A-5 | CH₃ | CH₃ | |
| O | H | H | CH₃ | H | 5-CH₂OCH₃ | SO₂ | A-5 | CH₃ | OCH₃ | |
| O | H | H | CH₃ | H | 5-CH₂CN | SO₂ | A-5 | CH₃ | OC₂H₅ | |
| O | H | H | CH₃ | H | 5-NH₂ | O | A-5 | CH₃ | SCH₃ | |
| O | H | H | CH₃ | H | 6-CH₂OCH₃ | O | A-5 | C₂H₅ | CH₃ | |
| O | H | H | CH₃ | H | 6-CH₂OCH₃ | S | A-5 | CH₂CF₃ | OCH₃ | |
| O | H | H | CH₃ | H | 6-CH₂OCH₃ | SO₂ | A-5 | CH₂CF₃ | OCH₃ | |
| O | H | H | CH₃ | H | 6-CH₂SCH₂CH₃ | S | A-5 | CH₃ | OC₂H₅ | |
| O | H | H | CH₃ | H | 6-CH₂SCH₂CH₃ | O | A-5 | C₂H₅ | C₂H₅ | |
| O | H | H | CH₃ | H | 6-CH₂SO₂CH₃ | SO₂ | A-5 | C₂H₅ | CH₃ | |
| O | H | H | CH₃ | H | 6-Si(CH₃)₃ | O | A-5 | CH₂CF₃ | CH₃ | |
| O | H | H | CH₃ | H | 6-Si(CH₃)₃ | SO | A-5 | CH₃ | SC₂H₅ | |
| O | H | H | CH₃ | H | 6-Si(CH₃)₃ | SO₂ | A-5 | CH₃ | OCH₃ | |
| O | H | H | CH₃ | H | 6-CH₂OCH₂CH₃ | SO | A-5 | C₂H₅ | OCH₃ | |
| O | H | H | C₂H₅ | H | 6-CH₂OC₂H₅ | SO₂ | A-5 | CH₃ | OCH₃ | |
| O | H | CH₃ | CH₃ | H | 6-CH₂OC₂H₅ | SO₂ | A-5 | CH₃ | OC₂H₅ | |
| O | H | H | CH₃ | CH₃ | 6-CH₂OC₂H₅ | O | A-5 | CH₃ | SCH₃ | |
| O | H | CH₃ | CH₃ | CH₃ | 6-CH₂OC₂H₅ | SO₂ | A-5 | CH₃ | SCH₃ | |
| O | CH₃ | H | CH₃ | H | 6-CH₂OC₂H₅ | O | A-5 | CH₃ | CH₃ | |

TABLE IV-continued $$\text{JSO}_2\text{NHCNA}$$
with W double-bonded above C, R attached below

J = J-1

| S | H | H | CH₃ | H | 6-CH₂OC₂H₅ | O | A-5 | CH₃ | CH₃ | |
|---|---|---|-----|---|------------|---|-----|-----|-----|---|

| W | R | R₁ | R₂ | R₃ | R₄ | Q | A | X₃ | | m.p. (°C.) |
|---|---|----|----|----|-----|---|---|----|----|-----|
| O | H | H | H | H | 6-CH₂OCH₃ | S | A-6 | CH₃ | | |
| O | H | H | CH₃ | H | 5-CH₂N(CH₃) | O | A-6 | OCH₃ | | |
| O | H | H | CH₃ | H | 5-CH₂OCH₃ | SO₂ | A-6 | CH₃ | | |
| O | H | H | CH₃ | H | 6-Si(CH₃)₃ | O | A-6 | CH₃ | | |
| O | H | H | CH₃ | H | 6-Si(CH₃)₃ | S | A-6 | CH₃ | | |
| O | H | H | CH₃ | H | 6-Si(CH₃)₃ | SO | A-6 | OCH₃ | | |
| O | H | H | CH₃ | H | 6-Si(CH₃)₃ | SO₂ | A-6 | CH₃ | | |
| O | H | H | CH₃ | H | 6-CH₂OCH₃ | S | A-6 | OCH₃ | | |
| O | H | H | CH₃ | H | 6-CH₂OCH₃ | SO₂ | A-6 | CH₃ | | |
| O | H | H | CH₃ | H | 6-CH₂OCH₃ | SO₂ | A-6 | OCH₃ | | |
| O | H | H | CH₃ | H | 6-CH₂SO₂CH₃ | SO₂ | A-6 | CH₃ | | |
| O | H | H | CH₃ | H | 6-CH₂CN | O | A-6 | CH₃ | | |
| O | H | H | C₂H₅ | H | 6-CH₂OC₂H₅ | SO₂ | A-6 | CH₃ | | |
| O | H | CH₃ | CH₃ | H | 6-CH₂OC₂H₅ | O | A-6 | OCH₃ | | |
| O | H | H | CH₃ | CH₃ | 6-CH₂OC₂H₅ | SO₂ | A-6 | OCH₃ | | |
| O | H | CH₃ | CH₃ | CH₃ | 6-CH₂OC₂H₅ | O | A-6 | OCH₃ | | |
| O | CH₃ | H | CH₃ | H | 6-CH₂OC₂H₅ | SO₂ | A-6 | OCH₃ | | |
| S | H | H | CH₃ | H | 6-CH₂OC₂H₅ | SO₂ | A-6 | OCH₃ | | |

| W | R | R₁ | R₂ | R₃ | R₄ | Q | A | X₄ | Y₄ | Z₁ | m.p. (°C.) |
|---|---|----|----|----|-----|---|---|----|----|----|-----|
| O | H | H | CH₃ | H | 6-CH₂OCH₃ | O | A-7 | OCH₃ | OCH₃ | CH | |
| O | H | H | CH₃ | H | 6-CH₂OCH₃ | SO₂ | A-7 | OCH₃ | CH₃ | CH | |
| O | H | H | CH₃ | H | 6-CH₂OCH₃ | SO₂ | A-7 | OCH₃ | CH₃ | N | |
| O | H | CH₃ | CH₃ | H | 6-Si(CH₃)₃ | O | A-7 | OCH₃ | CH₃ | N | |
| O | H | H | CH₃ | H | 6-CH₂SCH₃ | S | A-7 | Cl | OCH₃ | CH | |
| O | H | H | CH₃ | H | 6-N(CH₃)₂ | S | A-7 | CH₂OCH₃ | OCH₃ | CH | |

TABLE V $$\text{JSO}_2\text{NHCNA}$$
with W double-bonded, R attached

J = J-2

| W | R | R₂ | R₃ | R₄ | Q | A | X₁ | Y₁ | m.p. (°C.) |
|---|---|----|----|-----|---|---|----|----|-----|
| O | H | H | H | 6-Si(CH₃)₃ | O | A-2 | OCF₂H | O | |
| O | H | CH₃ | H | 5-CH₂CN | O | A-2 | CH₃ | O | |
| O | H | CH₃ | H | 5-N(CH₃)₂ | SO₂ | A-2 | OCH₃ | CH₂ | |
| O | H | CH₃ | H | 5-CH₂CH₂OCH₃ | S | A-2 | CH₃ | O | |
| O | H | CH₃ | H | 6-C₆H₄—3-SCH₃ | S | A-2 | OC₂H₅ | CH₂ | |
| O | H | CH₃ | H | 6-Si(CH₃)₃ | SO₂ | A-2 | OCH₃ | CH₂ | |
| O | H | CH₃ | H | 6-Si(CH₃)₃ | O | A-2 | CH₃ | CH₂ | |
| O | H | CH₃ | H | 6-Si(CH₃)₃ | SO | A-2 | CH₃ | O | |
| O | H | CH₃ | H | 6-PO(CH₃)₃ | SO₂ | A-2 | OCH₃ | O | |
| O | H | CH₃ | H | 6-CN | SO₂ | A-2 | OCF₂H | O | |
| O | H | CH₃ | H | 6-CN | O | A-2 | OCF₂H | CH₂ | |
| O | H | CH₃ | H | 6-NH₂ | O | A-2 | OC₂H₅ | O | |
| O | H | CH₃ | H | 6-CH₂CH₂OCH₃ | SO | A-2 | OCH₃ | O | |
| O | H | CH₃ | H | 6-CH₂SCH₃ | S | A-2 | CH₃ | CH₂ | |
| O | H | CH₃ | H | 6-CH₂OCH₃ | SO₂ | A-2 | CH₃ | CH₂ | |
| O | H | C₂H₅ | H | 6-CH₂OCH₃ | SO₂ | A-2 | OCH₃ | CH₂ | |
| O | H | CH₃ | CH₃ | 6-CH₂OCH₃ | O | A-2 | OCH₃ | O | |
| O | H | CH₃ | CH₃ | 6-CH₂OCH₃ | SO₂ | A-2 | OCF₂H | CH₂ | |
| O | CH₃ | CH₃ | H | 6-CH₂OCH₃ | SO₂ | A-2 | OCH₃ | O | |
| S | H | CH₃ | H | 6-CH₂OCH₃ | SO₂ | A-2 | CH₃ | O | |
| O | H | H | H | 6-CH₂OCH₂CF₃ | SO₂ | A-3 | OCH₃ | | |
| O | H | CH₃ | H | 6-CH₂CH₂SCH₃ | S | A-3 | OCH₃ | | |
| O | H | CH₃ | H | 6-NH₂ | SO₂ | A-3 | CH₃ | | |
| O | H | CH₃ | H | 5-CH₂OC₂H₅ | O | A-3 | OCF₂H | | |
| O | H | CH₃ | H | 6-cyclopropyl | O | A-3 | OCH₃ | | |
| O | H | CH₃ | H | 6-(2'-FC₆H₄) | O | A-3 | CH₃ | | |
| O | H | CH₃ | H | 6-CN | S | A-3 | OC₂H₅ | | |
| O | H | CH₃ | H | 6-CN | SO₂ | A-3 | OCF₂H | | |
| O | H | CH₃ | H | 6-N(CH₃)₂ | O | A-3 | OCH₃ | | |
| O | H | CH₃ | H | 6-CH₂OCH₃ | O | A-3 | CH₃ | | |
| O | H | CH₃ | H | 6-CH₂OCH₃ | SO₂ | A-3 | CH₃ | | |
| O | H | CH₃ | H | 6-CH₂OCH₃ | S | A-3 | OCH₃ | | |
| O | H | CH₃ | H | 6-Si(CH₃)₃ | O | A-3 | OCH₃ | | |
| O | H | CH₃ | H | 6-Si(CH₃)₃ | SO | A-3 | OC₂H₅ | | |
| O | H | CH₃ | H | 6-Si(CH₃)₃ | SO₂ | A-3 | CH₃ | | |

TABLE V-continued $$\underset{R}{\text{JSO}_2\text{NHCNA}}^{\overset{W}{\|}}$$

J = J-2

| W | R | R₂ | R₃ | R₄ | Q | A | X₁ | | | m.p. (°C.) |
|---|---|---|---|---|---|---|---|---|---|---|
| O | H | C₂H₅ | H | 6-Si(CH₃)₃ | O | A-3 | CH₃ | | | |
| O | H | CH₃ | CH₃ | 6-Si(CH₃)₃ | O | A-3 | OCH₃ | | | |
| O | H | CH₃ | CH₃ | 6-Si(CH₃)₃ | SO₂ | A-3 | CH₃ | | | |
| O | H | H | CH₃ | 6-Si(CH₃)₃ | O | A-3 | CH₃ | | | |
| S | H | CH₃ | H | 6-Si(CH₃)₃ | O | A-3 | CH₃ | | | |

| W | R | R₂ | R₃ | R₄ | Q | A | X₁ | Y₃ | | m.p. (°C.) |
|---|---|---|---|---|---|---|---|---|---|---|
| O | H | H | H | 6-Si(CH₃)₃ | SO₂ | A-4 | CH₃ | CH₃ | | |
| O | H | CH₃ | H | 5-CH₂OCH₃ | O | A-4 | OCH₃ | CH₃ | | |
| O | H | CH₃ | H | 5-CH₂CH₂CN | S | A-4 | OCH₃ | H | | |
| O | H | CH₃ | H | 6-Si(CH₃)₃ | SO | A-4 | OCF₂H | H | | |
| O | H | CH₃ | H | 6-Si(CH₃)₃ | SO₂ | A-4 | OCH₃ | H | | |
| O | H | CH₃ | H | 6-CH₂OCH₃ | O | A-4 | OC₂H₅ | CH₃ | | |
| O | H | CH₃ | H | 6-CH₂OCH₃ | S | A-4 | OCH₃ | CH₃ | | |
| O | H | CH₃ | H | 6-CH₂OCH₃ | SO₂ | A-4 | CH₃ | CH₃ | | |
| O | H | CH₃ | H | 6-CH₂CN | O | A-4 | OCH₃ | CH₃ | | |
| O | H | CH₃ | H | 6-CH₂CN | SO₂ | A-4 | OCF₂H | CH₃ | | |
| O | H | CH₃ | H | 6-CH₂SCH₃ | S | A-4 | CH₃ | H | | |
| O | H | CH₃ | H | 6-CH₂CH₂NO₂ | O | A-4 | CH₃ | H | | |
| O | H | CH₃ | H | 6-CH₂SO₂CH₃ | SO₂ | A-4 | OCH₃ | CH₃ | | |
| O | H | CH₃ | H | 6-CH₂NO₂ | O | A-4 | CH₃ | CH₃ | | |
| O | H | CH₃ | C₂H₅ | 6-CH₂CH₂OCH₃ | O | A-4 | OCH₃ | H | | |
| O | H | CH₃ | H | 6-CH₂CH₂OCH₃ | SO₂ | A-4 | CH₃ | H | | |
| O | H | CH₃ | CH₃ | 6-CH₂CH₂OCH₃ | SO₂ | A-4 | OCF₂H | H | | |
| O | H | CH₃ | CH₃ | 6-CH₂CH₂OCH₃ | SO₂ | A-4 | CH₃ | H | | |
| O | CH₃ | CH₃ | H | 6-CH₂CH₂OCH₃ | SO₂ | A-4 | CH₃ | H | | |
| S | H | CH₃ | H | 6-CH₂CH₂OCH₃ | SO₂ | A-4 | CH₃ | H | | |

| W | R | R₂ | R₃ | R₄ | Q | A | X₂ | Y₂ | | m.p. (°C.) |
|---|---|---|---|---|---|---|---|---|---|---|
| O | H | H | H | 6-CH₂CN | O | A-5 | CH₃ | CH₃ | | |
| O | H | CH₃ | H | 5-CH₂OCH₃ | SO₂ | A-5 | CH₃ | OCH₃ | | |
| O | H | CH₃ | H | 5-CH₂CN | SO₂ | A-5 | CH₃ | OC₂H₅ | | |
| O | H | CH₃ | H | 5-NH₂ | O | A-5 | CH₃ | SCH₃ | | |
| O | H | CH₃ | H | 6-CH₂OCH₃ | O | A-5 | C₂H₅ | CH₃ | | |
| O | H | CH₃ | H | 6-CH₂OCH₃ | S | A-5 | CH₂CF₃ | OCH₃ | | |
| O | H | CH₃ | H | 6-CH₂OCH₃ | SO₂ | A-5 | CH₂CF₃ | OCH₃ | | |
| O | H | CH₃ | H | 6-CH₂SCH₂CH₃ | S | A-5 | CH₃ | OC₂H₅ | | |
| O | H | CH₃ | H | 6-CH₂SCH₂CH₃ | O | A-5 | C₂H₅ | C₂H₅ | | |
| O | H | CH₃ | H | 6-CH₂SO₂CH₃ | SO₂ | A-5 | C₂H₅ | CH₃ | | |
| O | H | CH₃ | H | 6-Si(CH₃)₃ | O | A-5 | CH₂CF₃ | CH₃ | | |
| O | H | CH₃ | H | 6-Si(CH₃)₃ | SO | A-5 | CH₃ | SC₂H₅ | | |
| O | H | CH₃ | H | 6-Si(CH₃)₃ | SO₂ | A-5 | CH₃ | OCH₃ | | |
| O | H | CH₃ | H | 6-CH₂OCH₂CH₃ | SO | A-5 | C₂H₅ | OCH₃ | | |
| O | H | C₂H₅ | H | 6-CH₂OC₂H₅ | SO₂ | A-5 | CH₃ | OCH₃ | | |
| O | H | CH₃ | H | 6-CH₂OC₂H₅ | SO₂ | A-5 | CH₃ | OC₂H₅ | | |
| O | H | CH₃ | CH₃ | 6-CH₂OC₂H₅ | O | A-5 | CH₃ | SCH₃ | | |
| O | H | CH₃ | CH₃ | 6-CH₂OC₂H₅ | SO₂ | A-5 | CH₃ | SCH₃ | | |
| O | CH₃ | CH₃ | H | 6-CH₂OC₂H₅ | O | A-5 | CH₃ | CH₃ | | |
| S | H | CH₃ | H | 6-CH₂OC₂H₅ | O | A-5 | CH₃ | CH₃ | | |

| W | R | R₂ | R₃ | R₄ | Q | A | X₃ | | | m.p. (°C.) |
|---|---|---|---|---|---|---|---|---|---|---|
| O | H | H | H | 6-CH₂OCH₃ | S | A-6 | CH₃ | | | |
| O | H | CH₃ | H | 5-CH₂N(CH₃) | O | A-6 | OCH₃ | | | |
| O | H | CH₃ | H | 5-CH₂OCH₃ | SO₂ | A-6 | CH₃ | | | |
| O | H | CH₃ | H | 6-Si(CH₃)₃ | O | A-6 | CH₃ | | | |
| O | H | CH₃ | H | 6-Si(CH₃)₃ | S | A-6 | CH₃ | | | |
| O | H | CH₃ | H | 6-Si(CH₃)₃ | SO | A-6 | OCH₃ | | | |
| O | H | CH₃ | H | 6-Si(CH₃)₃ | SO₂ | A-6 | CH₃ | | | |
| O | H | CH₃ | H | 6-CH₂OCH₃ | S | A-6 | OCH₃ | | | |
| O | H | CH₃ | H | 6-CH₂OCH₃ | SO₂ | A-6 | CH₃ | | | |
| O | H | CH₃ | H | 6-CH₂OCH₃ | SO₂ | A-6 | OCH₃ | | | |
| O | H | CH₃ | H | 6-CH₂SO₂CH₃ | SO₂ | A-6 | CH₃ | | | |
| O | H | CH₃ | H | 6-CH₂CN | O | A-6 | CH₃ | | | |
| O | H | C₂H₅ | H | 6-CH₂OC₂H₅ | SO₂ | A-6 | CH₃ | | | |
| O | H | CH₃ | H | 6-CH₂OC₂H₅ | O | A-6 | OCH₃ | | | |
| O | H | CH₃ | CH₃ | 6-CH₂OC₂H₅ | SO₂ | A-6 | OCH₃ | | | |
| O | H | CH₃ | CH₃ | 6-CH₂OC₂H₅ | O | A-6 | OCH₃ | | | |
| O | CH₃ | CH₃ | H | 6-CH₂OC₂H₅ | SO₂ | A-6 | OCH₃ | | | |
| S | H | CH₃ | H | 6-CH₂OC₂H₅ | SO₂ | A-6 | OCH₃ | | | |

| W | R | R₂ | R₃ | R₄ | Q | A | X₄ | Y₄ | Z₁ | m.p. (°C.) |
|---|---|---|---|---|---|---|---|---|---|---|
| O | H | CH₃ | H | 6-CH₂OCH₃ | O | A-7 | OCH₃ | OCH₃ | CH | |
| O | H | CH₃ | H | 6-CH₂OCH₃ | SO₂ | A-7 | OCH₃ | CH₃ | CH | |
| O | H | CH₃ | H | 6-CH₂OCH₃ | SO₂ | A-7 | OCH₃ | CH₃ | N | |
| O | CH₃ | CH₃ | H | 6-Si(CH₃)₃ | O | A-7 | OCH₃ | CH₃ | N | |

TABLE V-continued $$\text{JSO}_2\text{NHCNA} \begin{array}{c} W \\ \| \\ | \\ R \end{array}$$

J = J-2

| W | R | R₆ | R₅ | R₄ | Q | A | X₁ | Y₁ | m.p. (°C.) |
|---|---|----|----|-----|---|---|----|----|-----------|
| O | H | CH₃ | H | 6-CH₂SCH₃ | S | A-7 | Cl | OCH₃ | CH |
| O | H | CH₃ | H | 6-N(CH₃)₂ | S | A-7 | CH₂OCH₃ | OCH₃ | CH |

TABLE VI $$\text{JSO}_2\text{NHCNA} \begin{array}{c} W \\ \| \\ | \\ R \end{array}$$

J = J-3

| W | R | R₆ | R₅ | R₇ | R₄ | Q | A | X₁ | Y₁ | m.p. (°C.) |
|---|---|----|----|----|-----|---|---|----|----|-----------|
| O | H | H | H | H | 7-Si(CH₃)₃ | O | A-2 | OCF₂H | O | |
| O | H | H | CH₃ | H | 6-CH₂CN | O | A-2 | CH₃ | O | |
| O | H | H | CH₃ | H | 6-N(CH₃)₂ | SO₂ | A-2 | OCH₃ | CH₂ | |
| O | H | H | CH₃ | H | 6-CH₂CH₂OCH₃ | S | A-2 | CH₃ | O | |
| O | H | H | CH₃ | H | 7-(3'-SCH₃—C₆H₄) | S | A-2 | OC₂H₅ | CH₂ | |
| O | H | H | CH₃ | H | 7-Si(CH₃)₃ | SO₂ | A-2 | OCH₃ | CH₂ | |
| O | H | H | CH₃ | H | 7-Si(CH₃)₃ | O | A-2 | CH₃ | CH₂ | |
| O | H | H | CH₃ | H | 7-Si(CH₃)₃ | SO | A-2 | CH₃ | O | |
| O | H | H | CH₃ | H | 7-PO(CH₃)₃ | SO₂ | A-2 | OCH₃ | O | |
| O | H | H | CH₃ | H | 7-CN | SO₂ | A-2 | OCF₂H | O | |
| O | H | H | CH₃ | H | 7-CN | O | A-2 | OCF₂H | CH₂ | |
| O | H | H | CH₃ | H | 7-NH₂ | O | A-2 | OC₂H₅ | O | |
| O | H | H | CH₃ | H | 7-CH₂CH₂OCH₃ | SO | A-2 | OCH₃ | O | |
| O | H | H | CH₃ | H | 7-CH₂SCH₃ | S | A-2 | CH₃ | CH₂ | |
| O | H | CH₃ | CH₃ | H | 7-CH₂OCH₃ | SO₂ | A-2 | CH₃ | CH₂ | |
| O | H | H | C₂H₅ | H | 7-CH₂OCH₃ | SO₂ | A-2 | OCH₃ | CH₂ | |
| O | H | H | CH₃ | CH₃ | 7-CH₂OCH₃ | O | A-2 | OCH₃ | O | |
| O | H | CH₃ | CH₃ | CH₃ | 7-CH₂OCH₃ | SO₂ | A-2 | OCF₂H | CH₂ | |
| O | CH₃ | H | CH₃ | H | 7-CH₂OCH₃ | SO₂ | A-2 | OCH₃ | O | |
| S | H | H | CH₃ | H | 7-CH₂OCH₃ | SO₂ | A-2 | CH₃ | O | |
| O | H | H | H | H | 7-CH₂OCH₂CF₃ | SO₂ | A-3 | OCH₃ | | |
| O | H | H | CH₃ | H | 7-CH₂CH₂SCH₃ | S | A-3 | OCH₃ | | |
| O | H | H | CH₃ | H | 7-NH₂ | SO₂ | A-3 | CH₃ | | |
| O | H | H | CH₃ | H | 6-CH₂OC₂H₅ | O | A-3 | OCF₂H | | |
| O | H | H | CH₃ | H | 7-cyclopropyl | O | A-3 | OCH₃ | | |
| O | H | H | CH₃ | H | 7-(2'-FC₆H₄) | O | A-3 | CH₃ | | |
| O | H | H | CH₃ | H | 7-CN | S | A-3 | OC₂H₅ | | |
| O | H | H | CH₃ | H | 7-CN | SO₂ | A-3 | OCF₂H | | |
| O | H | H | CH₃ | H | 7-N(CH₃)₂ | O | A-3 | OCH₃ | | |
| O | H | H | CH₃ | H | 7-CH₂OCH₃ | O | A-3 | CH₃ | | |
| O | H | H | CH₃ | H | 7-CH₂OCH₃ | SO₂ | A-3 | CH₃ | | |
| O | H | H | CH₃ | H | 7-CH₂OCH₃ | S | A-3 | OCH₃ | | |
| O | H | H | CH₃ | H | 7-Si(CH₃)₃ | O | A-3 | OCH₃ | | |
| O | H | H | CH₃ | H | 7-Si(CH₃)₃ | SO | A-3 | OC₂H₅ | | |
| O | H | H | CH₃ | H | 7-Si(CH₃)₃ | SO₂ | A-3 | CH₃ | | |
| O | H | H | C₂H₅ | H | 7-Si(CH₃)₃ | O | A-3 | CH₃ | | |
| O | H | H | CH₃ | CH₃ | 7-Si(CH₃)₃ | O | A-3 | OCH₃ | | |
| O | H | CH₃ | CH₃ | CH₃ | 7-Si(CH₃)₃ | SO₂ | A-3 | CH₃ | | |
| O | CH₃ | H | CH₃ | H | 7-Si(CH₃)₃ | O | A-3 | CH₃ | | |
| S | H | H | CH₃ | H | 7-Si(CH₃)₃ | O | A-3 | CH₃ | | |

| W | R | R₆ | R₅ | R₇ | R₄ | Q | A | X₁ | Y₃ | m.p. (°C.) |
|---|---|----|----|----|-----|---|---|----|----|-----------|
| O | H | H | H | H | 7-Si(CH₃)₃ | SO₂ | A-4 | CH₃ | CH₃ | |
| O | H | H | CH₃ | H | 6-CH₂OCH₃ | O | A-4 | OCH₃ | CH₃ | |
| O | H | H | CH₃ | H | 6-CH₂CH₂CN | S | A-4 | OCH₃ | H | |
| O | H | H | CH₃ | H | 7-Si(CH₃)₃ | SO | A-4 | OCF₂H | H | |
| O | H | H | CH₃ | H | 7-Si(CH₃)₃ | SO₂ | A-4 | OCH₃ | H | |
| O | H | H | CH₃ | H | 7-CH₂OCH₃ | O | A-4 | OC₂H₅ | CH₃ | |
| O | H | H | CH₃ | H | 7-CH₂OCH₃ | S | A-4 | OCH₃ | CH₃ | |
| O | H | H | CH₃ | H | 7-CH₂OCH₃ | SO₂ | A-4 | CH₃ | CH₃ | |
| O | H | H | CH₃ | H | 7-CH₂CN | O | A-4 | OCH₃ | CH₃ | |
| O | H | H | CH₃ | H | 7-CH₂CN | SO₂ | A-4 | OCF₂H | CH₃ | |
| O | H | H | CH₃ | H | 7-CH₂SCH₃ | S | A-4 | CH₃ | H | |
| O | H | H | CH₃ | H | 7-CH₂CH₂NO₂ | O | A-4 | CH₃ | H | |
| O | H | H | CH₃ | H | 7-CH₂SO₂CH₃ | SO₂ | A-4 | OCH₃ | CH₃ | |
| O | H | H | CH₃ | H | 7-CH₂NO₂ | O | A-4 | CH₃ | CH₃ | |
| O | H | H | CH₃ | C₂H₅ | 7-CH₂CH₂OCH₃ | O | A-4 | OCH₃ | H | |
| O | H | CH₃ | CH₃ | H | 7-CH₂CH₂OCH₃ | SO₂ | A-4 | CH₃ | H | |
| O | H | H | CH₃ | CH₃ | 7-CH₂CH₂OCH₃ | SO₂ | A-4 | OCF₂H | H | |
| O | H | CH₃ | CH₃ | CH₃ | 7-CH₂CH₂OCH₃ | SO₂ | A-4 | CH₃ | H | |
| O | CH₃ | H | CH₃ | H | 7-CH₂CH₂OCH₃ | SO₂ | A-4 | CH₃ | H | |

TABLE VI-continued $$JSO_2NHCNA$$ with W (double bond above C), R (below N)

J = J-3

| S | H | H | CH$_3$ | H | 7-CH$_2$CH$_2$OCH$_3$ | SO$_2$ | A-4 | CH$_3$ | H | |

| W | R | R$_6$ | R$_5$ | R$_7$ | R$_4$ | Q | A | X$_2$ | Y$_2$ | m.p. (°C.) |
|---|---|---|---|---|---|---|---|---|---|---|
| O | H | H | H | H | 7-CH$_2$CN | O | A-5 | CH$_3$ | CH$_3$ | |
| O | H | H | CH$_3$ | H | 6-CH$_2$OCH$_3$ | SO$_2$ | A-5 | CH$_3$ | OCH$_3$ | |
| O | H | H | CH$_3$ | H | 6-CH$_2$CN | SO$_2$ | A-5 | CH$_3$ | OC$_2$H$_5$ | |
| O | H | H | CH$_3$ | H | 6-NH$_2$ | O | A-5 | CH$_3$ | SCH$_3$ | |
| O | H | H | CH$_3$ | H | 7-CH$_2$OCH$_3$ | O | A-5 | C$_2$H$_5$ | CH$_3$ | |
| O | H | H | CH$_3$ | H | 7-CH$_2$OCH$_3$ | S | A-5 | CH$_2$CF$_3$ | OCH$_3$ | |
| O | H | H | CH$_3$ | H | 7-CH$_2$OCH$_3$ | SO$_2$ | A-5 | CH$_2$CF$_3$ | OCH$_3$ | |
| O | H | H | CH$_3$ | H | 7-CH$_2$SCH$_2$CH$_3$ | S | A-5 | CH$_3$ | OC$_2$H$_5$ | |
| O | H | H | CH$_3$ | H | 7-CH$_2$SCH$_2$CH$_3$ | O | A-5 | C$_2$H$_5$ | C$_2$H$_5$ | |
| O | H | H | CH$_3$ | H | 7-CH$_2$SO$_2$CH$_3$ | SO$_2$ | A-5 | C$_2$H$_5$ | CH$_3$ | |
| O | H | H | CH$_3$ | H | 7-Si(CH$_3$)$_3$ | O | A-5 | CH$_2$CF$_3$ | CH$_3$ | |
| O | H | H | CH$_3$ | H | 7-Si(CH$_3$)$_3$ | SO | A-5 | CH$_3$ | SC$_2$H$_5$ | |
| O | H | H | CH$_3$ | H | 7-Si(CH$_3$)$_3$ | SO$_2$ | A-5 | CH$_3$ | OCH$_3$ | |
| O | H | H | CH$_3$ | H | 7-CH$_2$OCH$_2$CH$_3$ | SO | A-5 | C$_2$H$_5$ | OCH$_3$ | |
| O | H | H | C$_2$H$_5$ | H | 7-CH$_2$OC$_2$H$_5$ | SO$_2$ | A-5 | CH$_3$ | OCH$_3$ | |
| O | H | CH$_3$ | CH$_3$ | H | 7-CH$_2$OC$_2$H$_5$ | SO$_2$ | A-5 | CH$_3$ | OC$_2$H$_5$ | |
| O | H | H | CH$_3$ | CH$_3$ | 7-CH$_2$OC$_2$H$_5$ | O | A-5 | CH$_3$ | SCH$_3$ | |
| O | H | CH$_3$ | CH$_3$ | CH$_3$ | 7-CH$_2$OC$_2$H$_5$ | SO$_2$ | A-5 | CH$_3$ | SCH$_3$ | |
| O | CH$_3$ | H | CH$_3$ | H | 7-CH$_2$OC$_2$H$_5$ | O | A-5 | CH$_3$ | CH$_3$ | |
| S | H | H | CH$_3$ | H | 7-CH$_2$OC$_2$H$_5$ | O | A-5 | CH$_3$ | CH$_3$ | |

| W | R | R$_6$ | R$_5$ | R$_7$ | R$_4$ | Q | A | X$_3$ | m.p. (°C.) |
|---|---|---|---|---|---|---|---|---|---|
| O | H | H | H | H | 7-CH$_2$OCH$_3$ | S | A-6 | CH$_3$ | |
| O | H | H | CH$_3$ | H | 6-CH$_2$N(CH$_3$) | O | A-6 | OCH$_3$ | |
| O | H | H | CH$_3$ | H | 6-CH$_2$OCH$_3$ | SO$_2$ | A-6 | CH$_3$ | |
| O | H | H | CH$_3$ | H | 7-Si(CH$_3$)$_3$ | O | A-6 | CH$_3$ | |
| O | H | H | CH$_3$ | H | 7-Si(CH$_3$)$_3$ | S | A-6 | CH$_3$ | |
| O | H | H | CH$_3$ | H | 7-Si(CH$_3$)$_3$ | SO | A-6 | OCH$_3$ | |
| O | H | H | CH$_3$ | H | 7-Si(CH$_3$)$_3$ | SO$_2$ | A-6 | CH$_3$ | |
| O | H | H | CH$_3$ | H | 7-CH$_2$OCH$_3$ | S | A-6 | OCH$_3$ | |
| O | H | H | CH$_3$ | H | 7-CH$_2$OCH$_3$ | SO$_2$ | A-6 | CH$_3$ | |
| O | H | H | CH$_3$ | H | 7-CH$_2$OCH$_3$ | SO$_2$ | A-6 | OCH$_3$ | |
| O | H | H | CH$_3$ | H | 7-CH$_2$SO$_2$CH$_3$ | SO$_2$ | A-6 | CH$_3$ | |
| O | H | H | CH$_3$ | H | 7-CH$_2$CN | O | A-6 | CH$_3$ | |
| O | H | H | C$_2$H$_5$ | H | 7-CH$_2$OC$_2$H$_5$ | SO$_2$ | A-6 | CH$_3$ | |
| O | H | CH$_3$ | CH$_3$ | H | 7-CH$_2$OC$_2$H$_5$ | O | A-6 | OCH$_3$ | |
| O | H | H | CH$_3$ | CH$_3$ | 7-CH$_2$OC$_2$H$_5$ | SO$_2$ | A-6 | OCH$_3$ | |
| O | H | CH$_3$ | CH$_3$ | CH$_3$ | 7-CH$_2$OC$_2$H$_5$ | O | A-6 | OCH$_3$ | |
| O | CH$_3$ | H | CH$_3$ | H | 7-CH$_2$OC$_2$H$_5$ | SO$_2$ | A-6 | OCH$_3$ | |
| S | H | H | CH$_3$ | H | 7-CH$_2$OC$_2$H$_5$ | SO$_2$ | A-6 | OCH$_3$ | |

| W | R | R$_1$ | R$_2$ | R$_3$ | R$_4$ | A | X$_4$ | Y$_4$ | Z$_1$ | m.p. (°C.) |
|---|---|---|---|---|---|---|---|---|---|---|
| O | H | H | CH$_3$ | H | 7-CH$_2$OCH$_3$ | A-7 | OCH$_3$ | OCH$_3$ | CH | |
| O | H | H | CH$_3$ | H | 7-CH$_2$OCH$_3$ | A-7 | OCH$_3$ | CH$_3$ | CH | |
| O | H | H | CH$_3$ | H | 7-CH$_2$OCH$_3$ | A-7 | OCH$_3$ | CH$_3$ | N | |
| O | H | CH$_3$ | CH$_3$ | H | 7-Si(CH$_3$)$_3$ | A-7 | OCH$_3$ | CH$_3$ | N | |
| O | H | H | CH$_3$ | H | 7-CH$_2$SCH$_3$ | A-7 | Cl | OCH$_3$ | CH | |
| O | H | H | CH$_3$ | H | 7-N(CH$_3$)$_2$ | A-7 | CH$_2$OCH$_3$ | OCH$_3$ | CH | |

TABLE VII $$JSO_2NHCNA$$ with W (double bond above C), R (below N)

A = A-1

| J | n | W | R | R$_1$ | R$_2$ | R$_4$ | X | Y | Z | m.p. (°C.) |
|---|---|---|---|---|---|---|---|---|---|---|
| J-4 | 0 | O | H | H | H | 6-CH$_2$OCH$_3$ | OCH$_3$ | OCH$_3$ | CH | |
| J-4 | 0 | O | H | H | CH$_3$ | 5-CH$_2$OCH$_3$ | OCH$_3$ | OCH$_3$ | CH | |
| J-4 | 0 | O | H | H | CH$_3$ | 5-Si(CH$_3$)$_3$ | OCH$_3$ | OCH$_3$ | CH | |
| J-4 | 0 | O | H | H | CH$_3$ | 5-NH$_2$ | OCH$_3$ | OCH$_3$ | CH | |
| J-4 | 0 | O | H | H | CH$_3$ | 6-CH$_2$CN | OCH$_3$ | OCH$_3$ | CH | |
| J-4 | 0 | O | H | H | CH$_3$ | 6-CH$_2$OCH$_3$ | OCH$_3$ | OCH$_3$ | CH | |
| J-4 | 0 | O | H | H | CH$_3$ | 6-CH$_2$OCH$_3$ | CH$_3$ | OCH$_3$ | CH | |
| J-4 | 0 | O | H | H | CH$_3$ | 6-CH$_2$OCH$_3$ | CH$_3$ | OCH$_3$ | N | |
| J-4 | 0 | O | H | H | CH$_3$ | 6-CH$_2$OCH$_3$ | CH$_3$ | C≡CH | N | |
| J-4 | 0 | O | H | H | CH$_3$ | 6-Si(CH$_3$)$_3$ | CH$_3$ | OCH$_3$ | N | |
| J-4 | 0 | O | H | H | CH$_3$ | 6-Si(CH$_3$)$_3$ | Cl | OCH$_3$ | CH | |

TABLE VII-continued $$JSO_2NHCNA \overset{W}{\underset{R}{\|}}$$

A = A-1

| | | | | | | | | | | |
|---|---|---|---|---|---|---|---|---|---|---|
| J-4 | 0 | O | H | H | CH$_3$ | 6-CH$_2$CH$_2$SCH$_3$ | OCH$_3$ | OCH$_3$ | CH | |
| J-4 | 0 | O | H | H | CH$_3$ | 6-CH$_2$CH$_2$SCH$_3$ | OCH$_3$ | CH$_3$ | N | |
| J-4 | 0 | O | H | H | CH$_3$ | 6-cyclopropyl | OCH$_3$ | CH$_3$ | N | |
| J-4 | 0 | O | H | H | CH$_2$CH$_3$ | 6-CH$_2$OCH$_3$ | OCH$_3$ | OCH$_3$ | CH | |
| J-4 | 0 | O | H | H | CH$_2$CH$_2$CH$_3$ | 6-CH$_2$OCH$_3$ | OCH$_3$ | OCH$_3$ | CH | |
| J-4 | 0 | O | H | CH$_3$ | CH$_3$ | 6-CH$_2$OCH$_3$ | OCH$_3$ | OCH$_3$ | CH | |
| J-4 | 0 | O | CH$_3$ | H | CH$_3$ | 6-CH$_2$OCH$_3$ | OCH$_3$ | OCH$_3$ | CH | |
| J-4 | 0 | S | H | H | CH$_3$ | 6-CH$_2$OCH$_3$ | OCH$_3$ | OCH$_3$ | CH | |
| J-4 | 1 | O | H | H | H | 7-CH$_2$OCH$_3$ | OCH$_3$ | OCH$_3$ | CH | |
| J-4 | 1 | O | H | H | CH$_3$ | 6-CH$_2$SCH$_3$ | OCH$_3$ | CH | | |
| J-4 | 1 | O | H | H | CH$_3$ | 6-CH$_2$OCH$_3$ | OCH$_3$ | OCH$_3$ | CH | |
| J-4 | 1 | O | H | H | CH$_3$ | 6-CH$_2$CH$_2$OCH$_3$ | OCH$_3$ | OCH$_3$ | CH | |
| J-4 | 1 | O | H | H | CH$_3$ | 7-N(CH$_3$)$_2$ | OCH$_3$ | OCH$_3$ | CH | |
| J-4 | 1 | O | H | H | CH$_3$ | 7-Si(CH$_3$)$_3$ | OCH$_3$ | OCH$_3$ | CH | |
| J-4 | 1 | O | H | H | CH$_3$ | 7-Si(CH$_3$)$_3$ | Cl | OCH$_3$ | CH | |
| J-4 | 1 | O | H | H | CH$_3$ | 7-Si(CH$_3$)$_3$ | CH$_3$ | OCH$_3$ | N | |
| J-4 | 1 | O | H | H | CH$_3$ | 7-Si(CH$_3$)$_3$ | OC$_2$H$_7$ | NHCH$_3$ | N | |
| J-4 | 1 | O | H | H | CH$_3$ | 7-CH$_2$OCH$_3$ | OC$_2$H$_7$ | SCH$_3$ | CH | |
| J-4 | 1 | O | H | H | CH$_3$ | 7-CH$_2$OCH$_3$ | OCH$_3$ | OCH$_3$ | CH | |
| J-4 | 1 | O | H | H | CH$_3$ | 7-CH$_2$OCH$_3$ | OCH$_3$ | CN | CH | |
| J-4 | 1 | O | H | H | CH$_3$ | 7-CH$_2$OCH$_3$ | OCH$_3$ | CH$_3$ | N | |
| J-4 | 1 | O | H | H | CH$_3$ | 7-CN | OCH$_3$ | CH$_3$ | N | |
| J-4 | 1 | O | H | H | CH$_3$ | 7-CN | OCH$_3$ | OCH$_3$ | CH | |
| J-4 | 1 | O | H | H | CH$_2$CH$_3$ | 7-CH$_2$OCH$_3$ | OCH$_3$ | OCH$_3$ | CH | |
| J-4 | 1 | 0 | H | H | CH$_2$CH$_2$CH$_3$ | 7-CH$_2$OCH$_3$ | OCH$_3$ | OCH$_3$ | CH | |
| J-4 | 1 | O | H | CH$_3$ | CH$_3$ | 7-CH$_2$OCH$_3$ | OCH$_3$ | OCH$_3$ | CH | |
| J-4 | 1 | O | CH$_3$ | H | CH$_3$ | 7-CH$_2$OCH$_3$ | OCH$_3$ | OCH$_3$ | CH | |
| J-4 | 1 | S | H | H | CH$_3$ | 7-CH$_2$OCH$_3$ | OCH$_3$ | OCH$_3$ | CH | |
| J-5 | 0 | O | H | H | — | 5-CH$_2$OC$_2$H$_5$ | OCH$_3$ | OCH$_3$ | CH | |
| J-5 | 0 | O | H | H | — | 5-(4'-Cl—C$_6$H$_4$) | OCH$_3$ | OCH$_3$ | CH | |
| J-5 | 0 | O | H | H | — | 5-N(CH$_3$)$_2$ | OCH$_3$ | OCH$_3$ | CH | |
| J-5 | 0 | O | H | H | — | 6-CH$_2$CH$_2$SCH$_3$ | OCH$_3$ | OCH$_3$ | CH | |
| J-5 | 0 | O | H | H | — | 6-CH$_2$CN | OCH$_3$ | OCH$_3$ | CH | |
| J-5 | 0 | O | H | H | — | 6-Si(CH$_3$)$_3$ | OCH$_3$ | OCH$_3$ | CH | |
| J-5 | 0 | O | H | H | — | 6-Si(CH$_3$)$_3$ | CH$_3$ | OCH$_3$ | CH | |
| J-5 | 0 | O | H | H | — | 6-Si(CH$_3$)$_3$ | CH$_3$ | OCH$_3$ | N | |
| J-5 | 0 | O | H | H | — | 6-Si(CH$_3$)$_3$ | CH$_3$ | C≡CH | N | |
| J-5 | 0 | O | H | H | — | 6-CH$_2$OCH$_3$ | CH$_3$ | OCH$_3$ | N | |
| J-5 | 0 | O | H | H | — | 6-CH$_2$OCH$_3$ | Cl | OCH$_3$ | CH | |
| J-5 | 0 | O | H | H | — | 6-(2'-OCH$_3$C$_6$H$_4$) | OCH$_3$ | OCH$_3$ | CH | |
| J-5 | 0 | O | H | CH$_3$ | — | 6-C$_6$H$_5$ | OCH$_3$ | OCH$_3$ | CH | |
| J-5 | 0 | O | H | CH$_3$ | — | 6-CH$_2$OCH$_3$ | OCH$_3$ | OCH$_3$ | CH | |
| J-5 | 0 | O | H | CH$_3$ | — | 6-Si(CH$_3$)$_3$ | OCH$_3$ | OCH$_3$ | CH | |
| J-5 | 0 | O | H | CH$_3$ | — | 6-CH$_2$SCH$_3$ | OCH$_3$ | OCH$_3$ | CH | |
| J-5 | 0 | O | CH$_3$ | H | — | 6-CH$_2$OCH$_3$ | OCH$_3$ | OCH$_3$ | CH | |
| J-5 | 0 | O | CH$_3$ | H | — | 6-CH$_2$OCH$_3$ | OCH$_3$ | CH$_3$ | N | |
| J-5 | 0 | S | H | H | — | 6-CH$_2$OCH$_3$ | OCH$_3$ | OCH$_3$ | CH | |
| J-5 | 1 | O | H | H | — | 6-CH$_2$Si(CH$_3$)$_3$ | OCH$_3$ | OCH$_3$ | CH | |
| J-5 | 1 | O | H | H | — | 6-N(CH$_3$)$_2$ | OCH$_3$ | OCH$_3$ | CH | 216–218 dec. |
| J-5 | 1 | O | H | H | — | 6-N(CH$_3$)$_2$ | CH$_3$ | OCH$_3$ | CH | 223–226 dec. |
| J-5 | 1 | O | H | H | — | 6-N(CH$_3$)$_2$ | CH$_3$ | OCH$_3$ | N | 196–200 dec. |
| J-5 | 1 | O | H | H | — | 6-N(CH$_3$)$_2$ | OCH$_3$ | OCH$_3$ | N | 199–205 dec. |
| J-5 | 1 | O | H | H | — | 6-CH$_2$OCH$_3$ | OCH$_3$ | OCH$_3$ | CH | |
| J-5 | 1 | O | H | H | — | 7-CH$_2$OCH$_3$ | CF$_3$ | OCH$_3$ | CH | |
| J-5 | 1 | O | H | H | — | 7-CH$_2$OCH$_3$ | OCH$_3$ | OCH$_3$ | CH | |
| J-5 | 1 | O | H | H | — | 7-CH$_2$OCH$_3$ | CH$_3$ | OCH$_3$ | N | |
| J-5 | 1 | O | H | H | — | 7-CH$_2$OCH$_3$ | CH$_3$ | NHCH$_3$ | N | |
| J-5 | 1 | O | H | H | — | 7-Si(CH$_3$)$_3$ | CH$_3$ | OCH$_3$ | N | |
| J-5 | 1 | O | H | H | — | 7-Si(CH$_3$)$_3$ | CH$_3$ | OCH$_3$ | CH | |
| J-5 | 1 | O | H | H | — | 7-Si(CH$_3$)$_3$ | OCH$_3$ | OCH$_3$ | CH | |
| J-5 | 1 | O | H | H | — | 7-N(CH$_3$)$_2$ | OCH$_3$ | OCH$_3$ | CH | |
| J-5 | 1 | O | H | H | — | 7-CH$_2$CH$_2$OCH$_3$ | OCH$_3$ | OCH$_3$ | CH | |
| J-5 | 1 | O | H | H | — | 7-CH$_2$CH$_2$OCH$_3$ | CH$_3$ | OCH$_3$ | N | |
| J-5 | 1 | O | H | CH$_3$ | — | 7-CH$_2$OCH$_3$ | CH$_3$ | OCH$_3$ | N | |
| J-5 | 1 | O | H | CH$_3$ | — | 7-CH$_2$OCH$_3$ | OCH$_3$ | OCH$_3$ | CH | |
| J-5 | 1 | O | H | CH$_3$ | — | 7-N(CH$_3$)$_2$ | OCH$_3$ | OCH$_3$ | CH | |
| J-5 | 1 | O | CH$_3$ | CH$_3$ | — | 7-CH$_2$OCH$_3$ | OCH$_3$ | OCH$_3$ | CH | |
| J-5 | 1 | S | H | H | — | 7-CH$_2$OCH$_3$ | OCH$_3$ | OCH$_3$ | CH | |
| J-6 | — | O | H | H | H | 7-CH$_2$OCH$_3$ | CH$_3$ | OCH$_3$ | N | |
| J-6 | — | O | H | H | H | 7-CH$_2$OC$_2$H$_5$ | CH$_3$ | OCH$_3$ | N | |
| J-6 | — | O | H | H | CH$_3$ | 6-CH$_2$OCH$_3$ | CH$_3$ | OCH$_3$ | N | |
| J-6 | — | O | H | H | CH$_3$ | 6-CH$_2$CH$_2$OCH$_3$ | CH$_3$ | OCH$_3$ | N | |
| J-6 | — | O | H | H | CH$_3$ | 7-CH$_2$SCH$_3$ | CH$_3$ | OCH$_3$ | N | |
| J-6 | — | O | H | H | CH$_3$ | 7-CH$_2$OCH$_2$CH$_3$ | CH$_3$ | OCH$_3$ | N | |

TABLE VII-continued $$\underset{R}{\text{JSO}_2\text{NHCNA}}\overset{\underset{\|}{W}}{}$$

A = A-1

| J | | W | R | R₁₂ | R₁₃ | R₄ | X | Y | Z | |
|---|---|---|---|---|---|---|---|---|---|---|
| J-6 | — | O | H | H | CH₃ | 7-N(CH₃)₂ | CH₃ | OCH₃ | N | |
| J-6 | — | O | H | H | CH₃ | 7-Si(CH₃)₃ | CH₃ | OCH₃ | N | |
| J-6 | — | O | H | H | CH₃ | 7-Si(CH₃)₃ | CH₃ | OCH₃ | CH | |
| J-6 | — | O | H | H | CH₃ | 7-Si(CH₃)₃ | OCH₃ | OCH₃ | CH | |
| J-6 | — | O | H | H | CH₃ | 7-CH₂OCH₃ | OCH₃ | OCH₃ | CH | |
| J-6 | — | O | H | H | CH₃ | 7-CH₂OCH₃ | Cl | OCH₃ | CH | |
| J-6 | — | O | H | H | CH₃ | 7-CH₂OCH₃ | OCH₃ | CH₃ | N | |
| J-6 | — | O | H | H | CH₃ | 7-CH₂OCH₃ | CH₃ | N(CH₃)₂ | N | |
| J-6 | — | O | H | H | CH₃ | 7-(4'-OCH₃C₆H₄) | OCH₃ | OCH₃ | CH | |
| J-6 | — | O | H | CH₃ | CH₃ | 7-CH₂OCH₃ | OCH₃ | OCH₃ | CH | |
| J-6 | — | O | H | CH₃ | CH₃ | 7-CH₂OCH₃ | CH₃ | OCH₃ | N | |
| J-6 | — | O | H | CH₃ | CH₃ | 7-Si(CH₃)₃ | CH₃ | OCH₃ | CH | |
| J-6 | — | O | CH₃ | CH₃ | CH₃ | 7-Si(CH₃)₃ | OCH₃ | OCH₃ | CH | |
| J-6 | — | S | H | CH₃ | CH₃ | 7-CH₂OCH₃ | OCH₃ | OCH₃ | CH | |
| J-7 | — | O | H | — | H | 7-CH₂OCH₃ | OCH₃ | OCH₃ | CH | |
| J-7 | — | O | H | — | H | 6-Si(CH₃)₃ | OCH₃ | OCH₃ | CH | |
| J-7 | — | O | H | — | H | 6-N(CH₃)₂ | OCH₃ | OCH₃ | CH | |
| J-7 | — | O | H | — | H | 6-N(CH₃)₂ | CH₃ | OCH₃ | CH | |
| J-7 | — | O | H | — | CH₃ | 6-N(CH₃)₂ | CH₃ | OCH₃ | CH | |
| J-7 | — | O | H | — | CH₃ | 6-N(CH₃)₂ | CH₃ | OCH₃ | N | |
| J-7 | — | O | H | — | CH₃ | 7-N(CH₃)₂ | CH₃ | OCH₃ | N | |
| J-7 | — | O | H | — | CH₃ | 7-N(CH₃)₂ | CH₃ | OCH₃ | CH | |
| J-7 | — | O | H | — | CH₃ | 7-CH₂OCH₃ | CH₃ | OCH₃ | CH | |
| J-7 | — | O | H | — | C₂H₅ | 7-CH₂OCH₃ | CH₃ | OCH₃ | CH | |
| J-7 | — | O | CH₃ | — | H | 7-CH₂OCH₃ | CH₃ | OCH₃ | CH | |
| J-7 | — | S | H | — | H | 7-CH₂OCH₃ | CH₃ | OCH₃ | N | |
| J-8 | — | O | H | — | H | 7-CH₂OCH₃ | OCH₃ | CH₃ | N | |
| J-8 | — | O | H | — | H | 7-Si(CH₃)₃ | OCH₃ | CH₃ | N | |
| J-8 | — | O | H | — | H | 7-Si(CH₃)₃ | OCH₃ | CH₃ | CH | |
| J-8 | — | O | H | — | H | 7-NH₂ | OCH₃ | CH₃ | CH | |
| J-8 | — | O | H | — | H | 7-N(CH₃)₂ | OCH₃ | CH₃ | CH | |
| J-8 | — | O | H | — | H | 7-N(CH₃)₂ | OCH₃ | OCH₃ | CH | |
| J-8 | — | O | H | — | H | 7-N(CH₃)₂ | OCH₃ | OCH₃ | N | |
| J-8 | — | O | H | — | CH₃ | 7-N(CH₃)₂ | CH₃ | OCH₃ | N | |
| J-8 | — | O | H | — | H | 6-N(CH₃)₂ | CH₃ | OCH₃ | N | |
| J-8 | — | O | CH₃ | — | H | 6-N(CH₃)₂ | CH₃ | OCH₃ | N | |
| J-8 | — | S | H | — | H | 6-N(CH₃)₂ | CH₃ | OCH₃ | N | |
| J-8 | — | O | H | — | H | 6-CH₂OCH₃ | CH₃ | OCH₃ | N | |
| J-9 | — | O | H | — | H | 7-CH₂OCH₃ | CH₃ | OCH₃ | N | |
| J-9 | — | O | H | — | H | 7-CH₂OCH₃ | CH₃ | OCH₃ | CH | |
| J-9 | — | O | H | — | H | 7-NH₂ | CH₃ | OCF₂H | CH | |
| J-9 | — | O | H | — | H | 7-N(CH₃)₂ | Cl | OCH₃ | CH | |
| J-9 | — | O | H | — | H | 7-Si(CH₃)₃ | Cl | OCH₃ | CH | |
| J-9 | — | O | H | — | H | 6-Si(CH₃)₃ | Cl | OCH₃ | CH | |
| J-9 | — | O | H | — | H | 6-Si(CH₃)₃ | OCH₃ | NHCH₃ | N | |
| J-9 | — | O | H | — | CH₃ | 6-N(CH₃)₂ | OCH₃ | NHCH₃ | N | |
| J-9 | — | O | H | — | CH₃ | 6-N(CH₃)₂ | OCH₃ | CH₃ | N | |
| J-9 | — | O | CH₃ | — | H | 6-N(CH₃)₂ | OCH₃ | CH₃ | CH | |
| J-9 | — | S | H | — | H | 6-CH₂OCH₃ | OCH₃ | OCH₃ | CH | |
| J-9 | — | O | H | — | H | 6-CH₂OCH₃ | OCH₃ | OCH₃ | CH | |

| J | n | W | R | R₁₂ | R₁₃ | R₄ | X | Y | Z | m.p. (°C.) |
|---|---|---|---|---|---|---|---|---|---|---|
| J-10 | 0 | O | H | H | H | 6-CH₂OC₃ | OCF₂H | OCF₂H | CH | |
| J-10 | 0 | O | H | H | H | 6-Si(CH₃)₃ | Cl | OCH₃ | CH | |
| J-10 | 0 | O | H | H | H | 6-CH₂NH₂ | SCH₃ | CH₃ | CH | |
| J-10 | 0 | O | H | H | H | 6-CN | CH₃ | OCH₃ | N | |
| J-10 | 0 | O | H | H | H | 5-N(CH₃)₂ | CH₃ | CH₃ | CH | 198–202 |
| J-10 | 0 | O | H | H | H | 5-N(CH₃)₂ | CH₃ | OCH₃ | CH | 204–207 |
| J-10 | 0 | O | H | H | H | 5-N(CH₃)₂ | OCH₃ | OCH₃ | CH | 176–180 |
| J-10 | 0 | O | H | H | H | 5-N(CH₃)₂ | Cl | OCH₃ | CH | 205–208 |
| J-10 | 0 | O | H | H | H | 5-N(CH₃)₂ | OCH₃ | OCH₃ | N | 200–202 |
| J-10 | 0 | O | H | H | CH₃ | 5-N(CH₃)₂ | OCH₃ | OCH₃ | N | |
| J-10 | 0 | O | H | CH₃ | CH₃ | 5-N(CH₃)₂ | CH₃ | OCH₃ | N | |
| J-10 | 0 | O | H | Br | H | 5-Si(CH₃)₃ | CH₃ | CH₃ | N | |
| J-10 | 0 | O | CH₃ | H | H | 5-Si(CH₃)₃ | CH₃ | OCH₃ | N | |
| J-10 | 0 | S | H | H | H | 5-Si(CH₃)₃ | CH₃ | OCH₃ | N | |
| J-10 | 1 | O | H | H | H | 6-Si(CH₃)₃ | Cl | OCH₃ | CH | |
| J-10 | 1 | O | H | H—H | H | 6-NHCH₃ | OCH₃ | CH₃ | CH | |
| J-10 | 1 | O | H | H | H | 6-NHCH₃ | OCH₃ | CH₃ | N | |
| J-10 | 1 | O | H | H | H | 6-CN | OCH₃ | OCH₃ | N | |
| J-10 | 1 | O | H | H | H | 6-CN | OCH₃ | OCH₃ | CH | |
| J-10 | 1 | O | H | H | H | 7-CN | Cl | OCH₃ | CH | |
| J-10 | 1 | O | H | H | H | 7-CN | C≡CH | OCH₃ | CH | |
| J-10 | 1 | O | H | H | H | 7-N(CH₃)₂ | Br | OCH₃ | CH | |
| J-10 | 1 | O | H | H | H | 7-N(CH₃)₂ | NH₂ | OCH₃ | CH | |

TABLE VII-continued

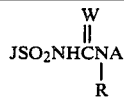

A = A-1

| J | n | W | R | | | R4 | X | Y | Z | |
|---|---|---|---|---|---|---|---|---|---|---|
| J-10 | 1 | O | H | H | H | 7-N(CH3)2 | N(CH3)2 | OCH3 | N | |
| J-10 | 1 | O | CH3 | H | H | 7-Si(CH3)3 | CH3 | OCH3 | N | |
| J-10 | 1 | S | H | H | H | 7-N(CH3)2 | CH3 | OCH3 | N | |
| J-11 | 0 | O | H | — | — | 2-N(C2H5)2 | CH3 | OCH3 | H | |
| J-11 | 0 | O | H | — | — | 2-Si(CH3)3 | CH3 | OCH3 | N | |
| J-11 | 0 | O | H | — | — | 2-Si(CH3)3 | CH3 | OCH3 | CH | |
| J-11 | 0 | O | H | — | — | 2-CH2OC2H5 | CH3 | OCH3 | CH | |
| J-11 | 0 | O | H | — | — | 3-CN | CH3 | OCH3 | CH | |
| J-11 | 0 | O | H | — | — | 3-N(CH3)2 | CH3 | OCH3 | CH | |
| J-11 | 0 | O | H | — | — | 3-N(CH3)2 | OCH3 | OCH3 | CH | |
| J-11 | 0 | O | H | — | — | 3-N(CH3)2 | OCH3 | CH3 | CH | |
| J-11 | 0 | O | H | — | — | 3-N(CH3)2 | OCH3 | OCH3 | N | |
| J-11 | 0 | O | CH3 | — | — | 3-N(CH3)2 | OCH3 | CH3 | N | |
| J-11 | 0 | S | H | — | — | 3-N(CH3)2 | OCH3 | CH3 | N | |

| J | n | W | R | R4 | X | Y | Z | m.p. (°C.) |
|---|---|---|---|---|---|---|---|---|
| J-11 | 1 | O | H | 2-CH2OCH3 | CH2CH2CH3 | OCH3 | CH | |
| J-11 | 1 | O | H | 2-CH2OCH3 | CH3 | OC2H5 | CH | |
| J-11 | 1 | O | H | 2-CH2OCH3 | Cl | CH3 | CH | |
| J-11 | 1 | O | H | 2-CH2OCH3 | Cl | OCH3 | CH | |
| J-11 | 1 | O | H | 2-Si(CH3)3 | OCH3 | CH3 | CH | |
| J-11 | 1 | O | H | 2-Si(CH3)3 | OCH3 | CH3 | N | |
| J-11 | 1 | O | H | 3-CN | NHCH3 | OC2H5 | N | |
| J-11 | 1 | O | H | 3-CN | OCH3 | CH2OCH3 | N | |
| J-11 | 1 | O | H | 3-N(CH3)2 | OCH3 | OCH3 | CH | |
| J-11 | 1 | O | H | 3-N(CH3)2 | OCH3 | OCH3 | N | |
| J-11 | 1 | O | CH3 | 3-N(CH3)2 | OCH3 | OCH3 | CH | |
| J-11 | 1 | S | H | 3-N(CH3)2 | OCH3 | OCH3 | CH | |
| J-12 | — | O | H | 2-CH2OCH3 | OCH3 | OCH3 | CH | 166–170 dec. |
| J-12 | — | O | H | 2-CH2OCH3 | CH3 | OCH3 | CH | 155–157 dec. |
| J-12 | — | O | H | 2-CH2OCH3 | CH3 | CH3 | CH | 205–207 dec. |
| J-12 | — | O | H | 2-CH2OCH3 | CH3 | CH3 | N | 197–201 dec. |
| J-12 | — | O | H | 2-CH2OCH3 | OCH3 | CH3 | N | 205–207 dec. |
| J-12 | — | O | H | 2-CH2OCH3 | OCH3 | OCH3 | N | 208–209 dec. |
| J-12 | — | O | H | 2-CH2SCH3 | OCH3 | OCH3 | N | |
| J-12 | — | O | H | 2-N(CH3)2 | OCH3 | OCH3 | CH | |
| J-12 | — | O | H | 3-CH2OCH3 | OCH3 | OCH3 | CH | |
| J-12 | — | O | H | 3-N(CH3)2 | OCH3 | OCH3 | CH | |
| J-12 | — | S | H | 3-N(CH3)2 | OCH3 | OCH3 | CH | |
| J-12 | — | O | CH3 | 3-N(CH3)2 | OCH3 | OCH3 | CH | |
| J-13 | — | O | H | 7-Si(CH3)3 | CH3 | OCH3 | N | |
| J-13 | — | O | H | 7-CH2OCH3 | CH3 | OCH3 | N | |
| J-13 | — | O | H | 7-CH2SCH3 | CH3 | OCH3 | N | |
| J-13 | — | O | H | 7-CN | CH3 | OCH3 | N | |
| J-13 | — | O | H | 7-N(CH3)2 | CH3 | OCH3 | N | |
| J-13 | — | O | H | 7-N(CH3)2 | CH3 | OCH3 | CH | |
| J-13 | — | O | H | 6-N(CH3)2 | OCH3 | OCH3 | CH | |
| J-13 | — | O | H | 6-CN | OCH3 | OCH3 | CH | |
| J-13 | — | O | H | 6-CN | Cl | OCH3 | CH | |
| J-13 | — | O | H | 6-NH2 | Cl | OCH3 | CH | |
| J-13 | — | O | CH3 | 7-CH2OCH3 | Cl | OCH3 | CH | |
| J-13 | — | S | H | 7-CH2OCH3 | CH3 | OCH3 | N | |

TABLE VIII

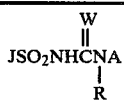

| J | n | W | R | R1 | R2 | R4 | A | X1 | Y1 | m.p. (°C.) |
|---|---|---|---|---|---|---|---|---|---|---|
| J-4 | 0 | O | H | H | CH3 | 6-CH2OCH3 | A-2 | OCH3 | O | |
| J-4 | 0 | O | H | H | CH3 | 6-CH2OCH3 | A-2 | CH3 | CH2 | |
| J-4 | 0 | O | H | H | CH3 | 6-Si(CH3)3 | A-2 | OCF2H | O | |
| J-4 | 0 | O | H | H | CH3 | 6-Si(CH3)3 | A-2 | CH3 | CH2 | |
| J-4 | 1 | O | H | H | CH3 | 7-Si(CH3)3 | A-2 | OC2H5 | CH2 | |
| J-4 | 1 | O | H | H | CH3 | 7-N(CH3)2 | A-2 | OCH3 | CH2 | |
| J-4 | 1 | O | H | CH3 | CH3 | 7-N(CH3)2 | A-2 | OCH3 | O | — |
| J-4 | 1 | S | H | H | CH3 | 7-CH2OCH3 | A-2 | CH3 | O | |
| J-5 | 0 | O | H | H | — | 6-CH2OCH3 | A-2 | CH3 | O | |
| J-5 | 0 | O | H | H | — | 6-CH2OCH3 | A-2 | OCH3 | O | |
| J-5 | 0 | O | H | CH3 | — | 6-N(CH3)2 | A-2 | OCH3 | O | |
| J-5 | 0 | O | H | CH3 | — | 6-N(CH3)2 | A-2 | OCH3 | CH2 | |
| J-5 | 1 | O | CH3 | CH3 | — | 7-Si(CH3)3 | A-2 | OCF2H | O | |

TABLE VIII-continued $$\text{JSO}_2\text{NHCNA} \overset{\overset{W}{\|}}{\underset{R}{|}}$$

| J | n | W | R | R₁₃ | R₁₄ | R₄ | A | X₁ | Y₁ | m.p. (°C.) |
|---|---|---|---|---|---|---|---|---|---|---|
| J-5 | 1 | O | H | CH₃ | — | 7-Si(CH₃)₃ | A-2 | CH₃ | CH₂ | |
| J-5 | 1 | O | H | H | — | 7-CH₂OCH₃ | A-2 | OC₂H₅ | CH₂ | |
| J-5 | 1 | O | H | H | — | 7-CH₂OCH₃ | A-2 | CH₃ | CH₂ | |
| J-6 | — | O | H | H | CH₃ | 7-CH₂OCH₃ | A-2 | CH₃ | CH₂ | |
| J-6 | — | O | H | H | H | 7-CH₂OCH₃ | A-2 | CH₃ | CH₂ | |
| J-6 | — | O | H | CH₃ | CH₃ | 7-CH₂OCH₃ | A-2 | OCH₃ | O | |
| J-6 | — | O | O | CH₃ | CH₃ | 7-Si(CH₃)₃ | A-2 | OCH₃ | CH₂ | |
| J-7 | — | O | H | — | H | 6-CH₂OCH₃ | A-2 | OCH₃ | O | |
| J-7 | — | O | H | — | H | 6-CH₂OCH₃ | A-2 | CH₃ | CH₂ | |
| J-7 | — | O | H | — | H | 7-N(CH₃)₂ | A-2 | OCF₂H | O | |
| J-7 | — | O | H | — | H | 7-N(CH₃)₂ | A-2 | CH₃ | CH₂ | |
| J-8 | — | O | H | — | H | 7-N(CH₃)₂ | A-2 | OC₂H₅ | CH₂ | |
| J-8 | — | O | CH₃ | — | CH₃ | 7-N(CH₃)₂ | A-2 | OCH₃ | CH₂ | |
| J-8 | — | O | H | — | CH₃ | 6-NH₂ | A-2 | OCH₃ | CH₂ | |
| J-8 | — | O | H | — | CH₃ | 6-N(CH₃)₂ | A-2 | OCH₃ | O | |
| J-9 | — | O | H | — | H | 7-Si(CH₃)₃ | A-2 | CH₃ | O | |
| J-9 | — | O | H | — | H | 7-Si(CH₃)₃ | A-2 | OCH₃ | O | |
| J-9 | — | O | H | — | H | 6-NH₂ | A-2 | OCH₃ | O | |
| J-9 | — | O | H | — | H | 6-N(CH₃)₂ | A-2 | OCH₃ | O | |
| J-11 | 0 | O | H | — | — | 2-CN | A-2 | CH₃ | O | |
| J-11 | 0 | O | H | — | — | 2-CH₂OCH₃ | A-2 | CH₃ | CH₂ | |
| J-11 | 0 | O | H | — | — | 2-CH₂OCH₃ | A-2 | OCF₂H | CH₂ | |
| J-11 | 0 | O | H | — | — | 3-CH₂OCH₃ | A-2 | OCF₂H | CH₂ | |
| J-11 | 1 | O | H | — | — | 3-CH₂OCH₃ | A-2 | OCH₃ | O | |
| J-11 | 1 | O | H | — | — | 3-N(CH₃)₂ | A-2 | CH₃ | O | |
| J-11 | 1 | O | H | — | — | 3-N(CH₃)₂ | A-2 | CH₃ | CH₂ | |
| J-11 | 1 | S | H | — | — | 2-CH₂OCH₃ | A-2 | CH₃ | CH₂ | |
| J-12 | — | O | H | — | — | 2-CH₂OCH₃ | A-2 | OCF₂H | CH₂ | |
| J-12 | — | O | H | — | — | 2-CH₂OCH₃ | A-2 | OCF₂H | O | |
| J-12 | — | O | H | — | — | 2-N(CH₃)₂ | A-2 | OCH₃ | O | |
| J-12 | — | O | CH₃ | — | — | 3-N(CH₃)₂ | A-2 | OCH₃ | O | |
| J-13 | — | O | H | — | — | 2-CH₂OCH₃ | A-2 | OCH₃ | O | |
| J-13 | — | O | H | — | — | 2-CH₂OCH₃ | A-2 | OCH₃ | CH₂ | |
| J-13 | — | O | H | — | — | 2-N(CH₃)₂ | A-2 | OCH₃ | CH₂ | |
| J-13 | — | O | H | — | — | 2-N(CH₃)₂ | A-2 | CH₃ | CH₂ | |

| J | n | W | R | R₁₃ | R₁₄ | R₄ | A | X₁ | Y₁ | m.p. (°C.) |
|---|---|---|---|---|---|---|---|---|---|---|
| J-10 | 0 | O | H | H | H | 5-N(CH₃)₂ | A-2 | OCH₃ | O | |
| J-10 | 0 | O | H | H | Br | 5-N(CH₃)₂ | A-2 | OCH₃ | CH₂ | |
| J-10 | 0 | O | H | H | CH₃ | 6-Si(CH₃)₃ | A-2 | OCH₃ | CH₂ | |
| J-10 | 0 | O | H | H | H | 6-Si(CH₃)₃ | A-2 | OCH₃ | CH₂ | |
| J-10 | 1 | O | H | H | H | 6-NH₂ | A-2 | OCH₃ | CH₂ | |
| J-10 | 1 | O | H | CH₃ | H | 6-NH₂ | A-2 | CH₃ | O | |
| J-10 | 1 | O | H | CH₃ | H | 7-N(CH₃)₂ | A-2 | OCH₃ | O | |
| J-10 | 1 | O | H | CH₃ | CH₃ | 7-N(CH₃)₂ | A-2 | OCF₂H | O | |

| J | n | W | R | R₁ | R₂ | R₄ | A | X₁ | m.p. (°C.) |
|---|---|---|---|---|---|---|---|---|---|
| J-4 | 0 | O | H | H | CH₃ | 6-Si(CH₃)₂ | A-3 | OCH₃ | |
| J-4 | 0 | O | H | H | CH₃ | 6-CH₂CH₂OCH₃ | A-3 | OCH₃ | |
| J-4 | 1 | O | H | H | CH₃ | 7-CH₂SCH₃ | A-3 | CH₃ | |
| J-4 | 1 | O | H | CH₃ | CH₃ | 7-CH₂SCH₃ | A-3 | OCF₂H | |
| J-5 | 0 | O | H | CH₃ | — | 6-CH₂SCH₃ | A-3 | OCF₂H | |
| J-5 | 0 | O | H | CH₃ | — | 6-CH₂SCH₃ | A-3 | CH₃ | |
| J-5 | 1 | O | H | CH₃ | — | 7-N(CH₃)₂ | A-3 | CH₃ | |
| J-5 | 1 | S | H | H | — | 7-Si(CH₃)₃ | A-3 | CH₃ | |
| J-6 | — | O | H | H | CH₃ | 7-Si(CH₃)₃ | A-3 | CH₃ | |
| J-6 | — | O | H | CH₃ | CH₃ | 7-Si(CH₃)₃ | A-3 | CH₃ | |
| J-6 | — | O | H | CH₃ | CH₃ | 7-CH₂OCH₃ | A-3 | CH₃ | |
| J-6 | — | O | H | H | CH₃ | 7-CH₂OCH₃ | A-3 | OCH₃ | |
| J-7 | — | O | H | — | H | 6-CH₂OCH₃ | A-3 | CH₃ | |
| J-7 | — | O | H | — | H | 6-CH₂OCH₃ | A-3 | OCH₃ | |
| J-7 | — | O | H | — | H | 7-N(CH₃)₂ | A-3 | OCH₃ | |
| J-7 | — | O | H | — | H | 7-N(CH₃)₂ | A-3 | CH₃ | |
| J-8 | — | O | H | — | H | 7-N(CH₃)₂ | A-3 | OCF₂H | |
| J-8 | — | O | CH₃ | — | CH₃ | 7-N(CH₃)₂ | A-3 | OCF₂H | |
| J-8 | — | O | H | — | CH₃ | 6-NH₂ | A-3 | OCF₂H | |
| J-8 | — | O | H | — | CH₃ | 6-N(CH₃)₂ | A-3 | OCF₂H | |
| J-9 | — | O | H | — | H | 7-Si(CH₃)₃ | A-3 | OCF₂H | |
| J-9 | — | O | H | — | H | 7-Si(CH₃)₃ | A-3 | OCH₃ | |
| J-9 | — | O | H | — | H | 6-NH₂ | A-3 | OCH₃ | |
| J-9 | — | O | H | — | H | 6-N(CH₃)₂ | A-3 | OCH₃ | |
| J-11 | 0 | O | H | — | — | 2-CN | A-3 | OCH₃ | |
| J-11 | 0 | O | H | — | — | 2-CH₂OCH₃ | A-3 | OCH₃ | |
| J-11 | 0 | O | H | — | — | 2-CH₂OCH₃ | A-3 | CH₃ | |
| J-11 | 0 | O | H | — | — | 3-CH₂OCH₃ | A-3 | CH₃ | |
| J-11 | 1 | O | H | — | — | 3-CH₂OCH₃ | A-3 | OCH₃ | |
| J-11 | 1 | O | H | — | — | 3-N(CH₃)₂ | A-3 | OCH₃ | |

TABLE VIII-continued $$\underset{R}{\overset{\overset{W}{\underset{\|}{}}}{JSO_2NHCNA}}$$

| J | n | W | R | | | R4 | A | X1 | | m.p. (°C.) |
|---|---|---|---|---|---|---|---|---|---|---|
| J-11 | 1 | O | H | — | — | 3-N(CH3)2 | A-3 | OCF2H | | |
| J-11 | 1 | S | H | — | — | 2-CH2OCH3 | A-3 | CH3 | | |
| J-12 | — | O | H | — | — | 2-CH2OCH3 | A-3 | CH3 | | |
| J-12 | — | O | H | — | — | 2-CH2OCH3 | A-3 | OCH3 | | |
| J-12 | — | O | H | — | — | 2-N(CH3)2 | A-3 | OCH3 | | |
| J-12 | — | O | CH3 | — | — | 3-N(CH3)2 | A-3 | OCH3 | | |
| J-13 | — | O | H | — | — | 2-CH2OCH3 | A-3 | OCH3 | | |
| J-13 | — | O | H | — | — | 2-CH2OCH3 | A-3 | CH3 | | |
| J-13 | — | O | H | — | — | 2-N(CH3)2 | A-3 | CH3 | | |
| J-13 | — | O | H | — | — | 2-N(CH3)2 | A-3 | OCH3 | | |

| J | n | W | R | R13 | R14 | R4 | A | X1 | | m.p. (°C.) |
|---|---|---|---|---|---|---|---|---|---|---|
| J-10 | 0 | O | H | H | H | 5-N(CH3)2 | A-3 | OCH3 | | |
| J-10 | 0 | O | H | H | Br | 5-N(CH3)2 | A-3 | OCH3 | | |
| J-10 | 0 | O | H | H | CH3 | 6-Si(CH3)3 | A-3 | OCH3 | | |
| J-10 | 0 | O | H | H | H | 6-Si(CH3)3 | A-3 | OCH3 | | |
| J-10 | 1 | O | H | H | H | 6-NH2 | A-3 | OCH3 | | |
| J-10 | 1 | O | H | CH3 | H | 6-NH2 | A-3 | CH3 | | |
| J-10 | 1 | O | H | CH3 | H | 7-N(CH3)2 | A-3 | OCF2H | | |
| J-10 | 1 | O | H | CH3 | CH3 | 7-N(CH3)2 | A-3 | CH3 | | |

| J | n | W | R | R1 | R2 | R4 | A | X1 | Y3 | m.p. (°C.) |
|---|---|---|---|---|---|---|---|---|---|---|
| J-4 | 0 | O | H | H | CH3 | 6-CH2SO2CH3 | A-4 | OCH3 | H | |
| J-4 | 0 | O | H | H | CH3 | 6-CH2OCH2CH3 | A-4 | OCH3 | H | |
| J-4 | 0 | O | H | H | CH3 | 6-CH2OCH2CH3 | A-4 | OCH3 | CH3 | |
| J-4 | 0 | O | H | CH3 | CH3 | 6-CH2OCH2CH3 | A-4 | OCH3 | CH3 | |
| J-4 | 1 | O | H | CH3 | CH3 | 6-CH2OCH2CH3 | A-4 | OCH3 | CH3 | |
| J-4 | 1 | O | H | H | CH3 | 7-CH2OCH3 | A-4 | CH3 | H | |
| J-4 | 1 | O | H | H | CH3 | 7-CH2OCH3 | A-4 | OCH3 | H | |
| J-4 | 1 | O | CH3 | H | CH3 | 7-CH2CH2SCH3 | A-4 | OCF2H | H | |
| J-5 | 0 | O | H | H | — | 6-CH2OCH3 | A-4 | CH3 | CH3 | |
| J-5 | 0 | O | H | CH3 | — | 5-CH2OCH3 | A-4 | CH3 | H | |
| J-5 | 1 | O | H | H | — | 6-CH2OCH3 | A-4 | CH3 | H | |
| J-5 | 1 | S | H | H | — | 7-CH2OCH3 | A-4 | CH3 | CH3 | |
| J-6 | — | O | CH3 | H | CH3 | 7-CH2OCH3 | A-4 | CH3 | CH3 | |
| J-6 | — | O | H | CH3 | CH3 | 7-CH2OCH3 | A-4 | OCH3 | H | |
| J-6 | — | O | H | CH3 | CH3 | 7-CH2OCH3 | A-4 | OCH3 | CH3 | |
| J-6 | — | O | H | CH3 | CH3 | 7-CH2OCH3 | A-4 | CH3 | H | |
| J-7 | — | O | H | — | H | 6-CH2OCH3 | A-4 | OCH3 | H | |
| J-7 | — | O | H | — | H | 6-CH2OCH3 | A-4 | CH3 | H | |
| J-7 | — | O | H | — | H | 7-N(CH3)2 | A-4 | CH3 | H | |
| J-7 | — | O | H | — | H | 7-N(CH3)2 | A-4 | OCH3 | H | |
| J-8 | — | O | H | — | H | 7-N(CH3)2 | A-4 | OCH3 | CH3 | |
| J-8 | — | O | CH3 | — | CH3 | 7-N(CH3)2 | A-4 | OCH3 | CH3 | |
| J-8 | — | O | H | — | CH3 | 6-NH2 | A-4 | OCH3 | CH3 | |
| J-8 | — | O | H | — | CH3 | 6-N(CH3)2 | A-4 | OCH3 | H | |
| J-9 | — | O | H | — | H | 7-Si(CH3)3 | A-4 | OCH3 | H | |
| J-9 | — | O | H | — | H | 7-Si(CH3)3 | A-4 | OCF2H | H | |
| J-9 | — | O | H | — | H | 6-NH2 | A-4 | OCF2H | H | |
| J-9 | — | O | H | — | H | 6-N(CH3)2 | A-4 | OCF2H | CH3 | |
| J-11 | 0 | O | H | — | — | 2-CN | A-4 | OCH3 | CH3 | |
| J-11 | 0 | O | H | — | — | 2-CH2OCH3 | A-4 | OCH3 | CH3 | |
| J-11 | 0 | O | H | — | — | 2-CH2OCH3 | A-4 | CH3 | CH3 | |
| J-11 | 0 | O | H | — | — | 3-CH2OCH3 | A-4 | CH3 | CH3 | |
| J-11 | 1 | O | H | — | — | 3-CH2OCH3 | A-4 | OCH3 | CH3 | |
| J-11 | 1 | O | H | — | — | 3-N(CH3)2 | A-4 | OCH3 | CH3 | |
| J-11 | 1 | O | H | — | — | 3-N(CH3)2 | A-4 | OCH3 | H | |
| J-11 | 1 | S | H | — | — | 2-CH2OCH3 | A-4 | OCH3 | H | |
| J-12 | — | O | H | — | — | 2-CH2OCH3 | A-4 | CH3 | H | |
| J-12 | — | O | H | — | — | 2-CH2OCH3 | A-4 | OCHF2 | H | |
| J-12 | — | O | H | — | — | 2-N(CH3)2 | A-4 | OCH3 | H | |
| J-12 | — | O | CH3 | — | — | 3-N(CH3)2 | A-4 | OCH3 | H | |
| J-13 | — | O | H | — | — | 2-CH2OCH3 | A-4 | OCH3 | H | |
| J-13 | — | O | H | — | — | 2-CH2OCH3 | A-4 | OCH3 | CH3 | |
| J-13 | — | O | H | — | — | 2-N(CH3)2 | A-4 | OCH3 | CH3 | |
| J-13 | — | O | H | — | — | 2-N(CH3)2 | A-4 | CH3 | CH3 | |

| J | n | W | R | R13 | R14 | R4 | A | X1 | Y1 | m.p. (°C.) |
|---|---|---|---|---|---|---|---|---|---|---|
| J-10 | 0 | O | H | H | H | 5-N(CH3)2 | A-4 | CH3 | CH3 | |
| J-10 | 0 | O | H | H | Br | 5-N(CH3)2 | A-4 | CH3 | H | |
| J-10 | 0 | O | H | H | CH3 | 6-Si(CH3)3 | A-4 | CH3 | H | |
| J-10 | 0 | O | H | H | H | 6-Si(CH3)3 | A-4 | OCF2H | H | |
| J-10 | 1 | O | H | H | H | 6-NH2 | A-4 | OCH3 | H | |
| J-10 | 1 | O | H | CH3 | H | 6-NH2 | A-4 | OCH3 | H | |
| J-10 | 1 | O | H | CH3 | H | 7-N(CH3)2 | A-4 | OCH3 | H | |
| J-10 | 1 | O | H | CH3 | CH3 | 7-N(CH3)2 | A-4 | OCH3 | H | |

TABLE VIII-continued $$JSO_2NHC(=W)NA\text{-}R$$

| J | n | W | R | R₁ | R₂ | R₄ | A | X₂ | Y₂ | m.p. (°C.) |
|---|---|---|---|---|---|---|---|---|---|---|
| J-4 | 0 | O | H | H | H | 6-CH₂CH₂OCH₃ | A-5 | CH₃ | OCH₃ | |
| J-4 | 0 | O | H | CH₃ | H | 6-CH₂CH₂OCH₃ | A-5 | CH₃ | OCH₃ | |
| J-4 | 1 | O | H | H | CH₃ | 7-Si(CH₃)₃ | A-5 | CH₃ | CH₃ | |
| J-4 | 1 | O | H | H | CH₃ | 7-Si(CH₃)₃ | A-5 | CH₂CF₃ | SCH₃ | |
| J-5 | 0 | O | H | CH₃ | — | 6-Si(CH₃)₃ | A-5 | CH₂CH₃ | OC₂H₅ | |
| J-5 | 0 | O | H | H | — | 6-Si(CH₃)₃ | A-5 | CH₂CH₃ | SCH₃ | |
| J-5 | 1 | O | H | CH₃ | — | 7-CH₂OCH₃ | A-5 | CH₂CH₃ | OCH₃ | |
| J-5 | 1 | O | H | H | — | 7-Si(CH₃)₃ | A-5 | CH₃ | OCH₃ | |
| J-6 | — | O | H | H | CH₃ | 7-Si(CH₃)₃ | A-5 | CH₃ | OCH₃ | |
| J-6 | — | O | H | CH₃ | CH₃ | 7-Si(CH₃)₃ | A-5 | CH₃ | CH₃ | |
| J-6 | — | O | H | CH₃ | CH₃ | 7-Si(CH₃)₃ | A-5 | CH₃ | SC₂H₅ | |
| J-6 | — | O | H | CH₃ | H | 6-CH₂SCH₃ | A-5 | CH₃ | C₂H₅ | |
| J-7 | — | O | H | — | H | 6-CH₂OCH₃ | A-5 | CH₃ | OCH₃ | |
| J-7 | — | O | H | — | H | 6-CH₂OCH₃ | A-5 | CH₃ | CH₃ | |
| J-7 | — | O | H | — | H | 7-N(CH₃)₂ | A-5 | CH₃ | CH₃ | |
| J-7 | — | O | H | — | H | 7-N(CH₃)₂ | A-5 | CH₃ | OCH₃ | |
| J-8 | — | O | H | — | H | 7-N(CH₃)₂ | A-5 | CH₃ | SCH₃ | |
| J-8 | — | O | CH₃ | — | CH₃ | 7-N(CH₃)₂ | A-5 | C₂H₅ | SCH₃ | |
| J-8 | — | O | H | — | CH₃ | 6-NH₂ | A-5 | C₂H₅ | CH₃ | |
| J-8 | — | O | H | — | CH₃ | 6-N(CH₃)₂ | A-5 | CH₃ | CH₃ | |
| J-9 | — | O | H | — | H | 7-Si(CH₃)₃ | A-5 | CH₃ | CH₃ | |
| J-9 | — | O | H | — | H | 7-Si(CH₃)₃ | A-5 | CH₂CF₃ | CH₃ | |
| J-9 | — | O | H | — | H | 6-NH₂ | A-5 | CH₂CF₃ | CH₃ | |
| J-9 | — | O | H | — | H | 6-N(CH₃)₂ | A-5 | CH₃ | CH₃ | |
| J-11 | 0 | O | H | — | — | 2-CN | A-5 | CH₃ | OCH₃ | |
| J-11 | 0 | O | H | — | — | 2-CH₂OCH₃ | A-5 | CH₃ | OCH₃ | |
| J-11 | 0 | O | H | — | — | 2-CH₂OCH₃ | A-5 | CH₃ | OC₂H₅ | |
| J-11 | 0 | O | H | — | — | 3-CH₂OCH₃ | A-5 | CH₃ | OC₂H₅ | |
| J-11 | 1 | O | H | — | — | 3-CH₂OCH₃ | A-5 | CH₃ | C₂H₅ | |
| J-11 | 1 | O | H | — | — | 3-N(CH₃)₂ | A-5 | CH₂F | CH₃ | |
| J-11 | 1 | O | H | — | — | 3-N(CH₃)₂ | A-5 | CH₃ | CH₃ | |
| J-11 | 1 | S | H | — | — | 2-CH₂OCH₃ | A-5 | CH₃ | CH₃ | |
| J-12 | — | O | H | — | — | 2-CH₂OCH₃ | A-5 | OCH₃ | OCH₃ | |
| J-12 | — | O | H | — | — | 2-CH₂OCH₃ | A-5 | OCH₃ | SCH₃ | |
| J-12 | — | O | H | — | — | 2-N(CH₃)₂ | A-5 | CH₃ | OCH₃ | |
| J-12 | — | O | CH₃ | — | — | 3-N(CH₃)₂ | A-5 | CH₃ | OCH₃ | |
| J-13 | — | O | H | — | — | 2-CH₂OCH₃ | A-5 | CH₃ | CH₃ | |
| J-13 | — | O | H | — | — | 2-CH₂OCH₃ | A-5 | CH₂CF₃ | CH₃ | |
| J-13 | — | O | H | — | — | 2-N(CH₃)₂ | A-5 | CH₃ | CH₃ | |
| J-13 | — | O | H | — | — | 2-N(CH₃)₂ | A-5 | CH₃ | CH₃ | |

| J | n | W | R | R₁₃ | R₁₄ | R₄ | A | X₂ | Y₂ | m.p. (°C.) |
|---|---|---|---|---|---|---|---|---|---|---|
| J-10 | 0 | O | H | H | H | 5-N(CH₃)₂ | A-5 | C₂H₅ | CH₃ | |
| J-10 | 0 | O | H | H | Br | 5-N(CH₃)₂ | A-5 | C₂H₅ | OCH₃ | |
| J-10 | 0 | O | H | H | CH₃ | 6-Si(CH₃)₃ | A-5 | C₂H₅ | OCH₃ | |
| J-10 | 0 | O | H | H | H | 6-Si(CH₃)₃ | A-5 | OCH₃ | SCH₃ | |
| J-10 | 1 | O | H | H | H | 6-NH₂ | A-5 | OCH₃ | CH₃ | |
| J-10 | 1 | O | H | CH₃ | H | 6-NH₂ | A-5 | OCH₃ | CH₃ | |
| J-10 | 1 | O | H | CH₃ | H | 7-N(CH₃)₂ | A-5 | OCH₃ | CH₃ | |
| J-10 | 1 | O | H | CH₃ | CH₃ | 7-N(CH₃)₂ | A-5 | OCH₃ | CH₃ | |

| J | n | W | R | R₁ | R₂ | R₄ | A | X₃ | m.p. (°C.) |
|---|---|---|---|---|---|---|---|---|---|
| J-4 | 0 | S | H | H | H | 6-CH₂OCH₃ | A-6 | CH₃ | |
| J-4 | 0 | O | H | H | CH₃ | 6-CH₂OCH₃ | A-6 | CH₃ | |
| J-4 | 1 | O | H | H | CH₃ | 7-CH₂OCH₃ | A-6 | OCH₃ | |
| J-4 | 1 | O | H | CH₃ | CH₃ | 7-CH₂OCH₃ | A-6 | OCH₃ | |
| J-5 | 0 | O | H | CH₃ | — | 6-CH₂CH₂OCH₃ | A-6 | CH₃ | |
| J-5 | 0 | O | H | CH₃ | — | 6-Si(CH₃)₃ | A-6 | CH₃ | |
| J-5 | 1 | O | H | CH₃ | — | 7-Si(CH₃)₃ | A-6 | CH₃ | |
| J-5 | 1 | O | H | CH₃ | — | 7-Si(CH₃)₃ | A-6 | CH₃ | |
| J-6 | — | O | H | CH₃ | CH₃ | 7-Si(CH₃)₃ | A-6 | CH₃ | |
| J-6 | — | O | H | CH₃ | CH₃ | 7-CH₂OCH₃ | A-6 | CH₃ | |
| J-6 | — | O | H | H | CH₃ | 7-CH₂OCH₃ | A-6 | OCH₃ | |
| J-6 | — | O | H | H | CH₃ | 7-CH₂SCH₃ | A-6 | OCH₃ | |
| J-7 | — | O | H | — | H | 6-CH₂OCH₃ | A-6 | CH₃ | |
| J-7 | — | O | H | — | H | 6-CH₂OCH₃ | A-6 | OCH₃ | |
| J-7 | — | O | H | — | H | 7-N(CH₃)₂ | A-6 | CH₃ | |
| J-7 | — | O | H | — | H | 7-N(CH₃)₂ | A-6 | OCH₃ | |
| J-8 | — | O | H | — | H | 7-N(CH₃)₂ | A-6 | OCH₃ | |
| J-8 | — | O | CH₃ | — | CH₃ | 7-N(CH₃)₂ | A-6 | OCH₃ | |
| J-8 | — | O | H | — | CH₃ | 6-NH₂ | A-6 | OCH₃ | |
| J-8 | — | O | H | — | CH₃ | 6-N(CH₃)₂ | A-6 | CH₃ | |
| J-9 | — | O | H | — | H | 7-Si(CH₃)₃ | A-6 | CH₃ | |
| J-9 | — | O | H | — | H | 7-Si(CH₃)₃ | A-6 | OCH₃ | |
| J-9 | — | O | H | — | H | 6-NH₂ | A-6 | OCH₃ | |
| J-9 | — | O | H | — | H | 6-N(CH₃)₂ | A-6 | OCH₃ | |

TABLE VIII-continued $$JSO_2NHCNA \atop \underset{R}{|} \overset{W}{\overset{\|}{|}}$$

| J | n | W | R | | | R₄ | A | X₃ | | | m.p. (°C.) |
|---|---|---|---|---|---|---|---|---|---|---|---|
| J-11 | 0 | O | H | — | — | 2-CN | A-6 | OCH₃ | | | |
| J-11 | 0 | O | H | — | — | 2-CH₂OCH₃ | A-6 | OCH₃ | | | |
| J-11 | 0 | O | H | — | — | 2-CH₂OCH₃ | A-6 | CH₃ | | | |
| J-11 | 0 | O | H | — | — | 3-CH₂OCH₃ | A-6 | CH₃ | | | |
| J-11 | 1 | O | H | — | — | 3-CH₂OCH₃ | A-6 | CH₃ | | | |
| J-11 | 1 | O | H | — | — | 3-N(CH₃)₂ | A-6 | CH₃ | | | |
| J-11 | 1 | O | H | — | — | 3-N(CH₃)₂ | A-6 | OCH₃ | | | |
| J-11 | 1 | S | H | — | — | 2-CH₂OCH₃ | A-6 | OCH₃ | | | |
| J-12 | — | O | H | — | — | 2-CH₂OCH₃ | A-6 | OCH₃ | | | |
| J-12 | — | O | H | — | — | 2-CH₂OCH₃ | A-6 | CH₃ | | | |
| J-12 | — | O | H | — | — | 2-N(CH₃)₂ | A-6 | CH₃ | | | |
| J-12 | — | O | CH₃ | — | — | 3-N(CH₃)₂ | A-6 | CH₃ | | | |
| J-13 | — | O | H | — | — | 2-CH₂OCH₃ | A-6 | CH₃ | | | |
| J-13 | — | O | H | — | — | 2-CH₂OCH₃ | A-6 | OCH₃ | | | |
| J-13 | — | O | H | — | — | 2-N(CH₃)₂ | A-6 | OCH₃ | | | |
| J-13 | — | O | H | — | — | 2-N(CH₃)₂ | A-6 | CH₃ | | | |

| J | n | W | R | R₁₃ | R₁₄ | R₄ | A | X₃ | | | m.p. (°C.) |
|---|---|---|---|---|---|---|---|---|---|---|---|
| J-10 | 0 | O | H | H | H | 5-N(CH₃)₂ | A-6 | CH₃ | | | |
| J-10 | 0 | O | H | H | Br | 5-N(CH₃)₂ | A-6 | CH₃ | | | |
| J-10 | 0 | O | H | H | CH₃ | 6-Si(CH₃)₃ | A-6 | CH₃ | | | |
| J-10 | 0 | O | H | H | H | 6-Si(CH₃)₃ | A-6 | CH₃ | | | |
| J-10 | 1 | O | H | H | H | 6-NH₂ | A-6 | CH₃ | | | |
| J-10 | 1 | O | H | CH₃ | H | 6-NH₂ | A-6 | CH₃ | | | |
| J-10 | 1 | O | H | CH₃ | H | 7-N(CH₃)₂ | A-6 | CH₃ | | | |
| J-10 | 1 | O | H | CH₃ | CH₃ | 7-N(CH₃)₂ | A-6 | CH₃ | | | |

| J | n | W | R | R₁ | R₂ | R₄ | A | X₄ | Y₄ | Z₁ | m.p. (°C.) |
|---|---|---|---|---|---|---|---|---|---|---|---|
| J-4 | 0 | O | H | H | H | 6-CH₂OCH₃ | A-7 | CH₃ | OCH₃ | CH | |
| J-4 | 0 | O | H | H | CH₃ | 6-CH₂OCH₃ | A-7 | OCH₃ | OCH₃ | CH | |
| J-4 | 0 | S | H | H | CH₃ | 6-CH₂OCH₃ | A-7 | OCH₃ | OCH₃ | CH | |
| J-4 | 1 | O | H | H | CH₃ | 7-CH₂OCH₃ | A-7 | OCH₃ | OCH₃ | CH | |
| J-4 | 1 | O | H | H | CH₃ | 7-CH₂CH₂SCH₃ | A-7 | OCH₃ | OCH₃ | N | |
| J-4 | 1 | O | H | CH₃ | CH₃ | 7-Si(CH₃)₃ | A-7 | CH₃ | OCH₃ | N | |
| J-5 | 0 | O | H | H | — | 6-CH₂SCH₃ | A-7 | Cl | OCH₃ | N | |
| J-5 | 0 | O | H | H | — | 6-Si(CH₃)₃ | A-7 | CH₂OCH₃ | OCH₃ | CH | |
| J-5 | 0 | O | CH₃ | H | — | 6-Si(CH₃)₃ | A-7 | OCH₃ | OCH₃ | CH | |
| J-5 | 1 | O | H | H | — | 7-Si(CH₃)₃ | A-7 | OCH₃ | OCH₃ | CH | |
| J-5 | 1 | O | H | H | — | 7-CH₂OCH₃ | A-7 | OC₂H₅ | OCH₃ | N | |
| J-5 | 1 | O | H | CH₃ | — | 7-CH₂OCH₃ | A-7 | CH₃ | OCH₃ | N | |
| J-6 | — | O | H | CH₃ | CH₃ | 7-CH₂OCH₃ | A-7 | OCH₃ | CH₃ | CH | |
| J-6 | — | O | H | H | CH₃ | 7-Si(CH₃)₃ | A-7 | OCH₃ | OCH₂CH₃ | CH | |
| J-6 | — | O | H | H | CH₃ | 7-Si(CH₃)₃ | A-7 | OCH₃ | Cl | CH | |
| J-6 | — | O | H | H | H | 7-Si(CH₃)₃ | A-7 | OCH₃ | OCH₃ | CH | |
| J-7 | — | O | H | — | H | 6-CH₂OCH₃ | A-7 | CH₃ | OCH₃ | CH | |
| J-7 | — | O | H | — | H | 6-CH₂OCH₃ | A-7 | OCH₃ | OCH₃ | CH | |
| J-7 | — | O | H | — | H | 7-N(CH₃)₂ | A-7 | OCH₃ | OCH₃ | CH | |
| J-7 | — | O | H | — | H | 7-N(CH₃)₂ | A-7 | OCH₃ | CH₃ | CH | |
| J-8 | — | O | H | — | H | 7-N(CH₃)₂ | A-7 | CH₃ | CH₃ | CH | |
| J-8 | — | O | CH₃ | — | CH₃ | 7-N(CH₃)₂ | A-7 | CH₃ | CH₃ | N | |
| J-8 | — | O | H | — | CH₃ | 6-NH₂ | A-7 | CH₃ | CH₃ | N | |
| J-8 | — | O | H | — | CH₃ | 6-N(CH₃)₂ | A-7 | Cl | OCH₃ | CH | |
| J-9 | — | O | H | — | H | 7-Si(CH₃)₃ | A-7 | OCH₃ | OCH₃ | N | |
| J-9 | — | O | H | — | H | 7-Si(CH₃)₃ | A-7 | OCH₃ | CH₃ | N | |
| J-9 | — | O | H | — | H | 6-NH₂ | A-7 | CH₂OCH₃ | OCH₃ | CH | |
| J-9 | — | O | H | — | H | 6-N(CH₃)₂ | A-7 | CH₂OCH₃ | OCH₃ | CH | |
| J-11 | 0 | O | H | — | — | 2-CN | A-7 | OCH₃ | OCH₃ | CH | |
| J-11 | 0 | O | H | — | — | 2-CH₂OCH₃ | A-7 | OCH₃ | OCH₃ | N | |
| J-11 | 0 | O | H | — | — | 2-CH₂OCH₃ | A-7 | CH₃ | OCH₃ | N | |
| J-11 | 0 | O | H | — | — | 3-CH₂OCH₃ | A-7 | CH₃ | OCH₃ | CH | |
| J-11 | 1 | O | H | — | — | 3-CH₂OCH₃ | A-7 | OC₂H₅ | OCH₃ | CH | |
| J-11 | 1 | O | H | — | — | 3-N(CH₃)₂ | A-7 | CH₃ | OCH₃ | CH | |
| J-11 | 1 | O | H | — | — | 3-N(CH₃)₂ | A-7 | CH₃ | OC₂H₅ | CH | |
| J-11 | 1 | S | H | — | — | 2-CH₂OCH₃ | A-7 | OCH₃ | CH₃ | CH | |
| J-12 | — | O | H | — | — | 2-CH₂OCH₃ | A-7 | OCH₃ | CH₃ | N | |
| J-12 | — | O | H | — | — | 2-CH₂OCH₃ | A-7 | OCH₃ | OCH₃ | CH | |
| J-12 | — | O | H | — | — | 2-N(CH₃)₂ | A-7 | CH₃ | OCH₃ | CH | |
| J-12 | — | O | CH₃ | — | — | 3-N(CH₃)₂ | A-7 | CH₃ | OCH₃ | N | |
| J-13 | — | O | H | — | — | 2-CH₂OCH₃ | A-7 | CH₃ | OCH₃ | N | |
| J-13 | — | O | H | — | — | 2-CH₂OCH₃ | A-7 | OCH₃ | OCH₃ | N | |
| J-13 | — | O | H | — | — | 2-N(CH₃)₂ | A-7 | OCH₃ | OCH₃ | CH | |
| J-13 | — | O | H | — | — | 2-N(CH₃)₂ | A-7 | Cl | OCH₃ | CH | |

| J | n | W | R | R₁₃ | R₁₄ | R₄ | A | X₄ | Y₄ | Z₁ | m.p. (°C.) |
|---|---|---|---|---|---|---|---|---|---|---|---|
| J-10 | 0 | O | H | H | H | 5-N(CH₃)₂ | A-7 | OCH₃ | CH₃ | CH | |
| J-10 | 0 | O | H | H | Br | 5-N(CH₃)₂ | A-7 | OCH₃ | Cl | N | |
| J-10 | 0 | O | H | H | CH₃ | 6-Si(CH₃)₃ | A-7 | OCH₃ | OCH₃ | N | |

TABLE VIII-continued $$JSO_2NHCNA \overset{W}{\underset{R}{\parallel}}$$

| J | n | X | Y | R₁ | R₂ | Sub | A | R | | |
|---|---|---|---|---|---|---|---|---|---|---|
| J-10 | 0 | O | H | H | H | 6-Si(CH₃)₃ | A-7 | CH₃ | OCH₃ | CH |
| J-10 | 1 | O | H | H | H | 6-NH₂ | A-7 | CH₃ | OCH₃ | CH |
| J-10 | 1 | O | H | CH₃ | H | 6-NH₂ | A-7 | CH₃ | OCH₃ | N |
| J-10 | 1 | O | H | CH₃ | H | 7-N(CH₃)₂ | A-7 | CH₃ | OCH₃ | N |
| J-10 | 1 | O | H | CH₃ | CH₃ | 7-N(CH₃)₂ | A-7 | CH₃ | OCH₃ | N |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE IX

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 10

Wettable Powder

| | |
|---|---|
| N—[(4,6-dimethoxypyrimidin-2-yl)aminocarbonyl]-2,3-dihydro-6-(methoxymethyl)-2-methylbenzo[b]-thiophene-7-sulfonamide, 1,1-dioxide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 11

Wettable Powder

| | |
|---|---|
| N—[(4,6-dimethoxypyrimidin-2-yl)aminocarbonyl]-2,3-dihydro-2-methyl-6-(trimethylsilyl)benzo[b]-thiophene-7-sulfonamide, 1,1-dioxide | 50% |
| sodium alkylnaphthalenesulfonate | 2% |
| low viscosity methyl cellulose | 2% |

| | |
|---|---|
| diatomaceous earth | 46% |

The ingredients are blended, coarsely hammer-milled and then air-milled to produce particles essentially all below 10 microns in diameter. The product is reblended before packaging.

EXAMPLE 12

Granule

| | |
|---|---|
| Wettable Powder of Example 11 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 13

Extruded Pellet

| | |
|---|---|
| N—[(4,6-dimethoxypyrimidin-2-yl)aminocarbonyl]-2,3-dihydro-6-(methoxymethyl)-2-methylbenzo[b]-thiophene-7-sulfonamide, 1,1-dioxide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 14

Oil Suspension

| | |
|---|---|
| N—[(4,6-dimethoxypyrimidin-2-yl)aminocarbonyl]-2,3-dihydro-2-methyl-6-(trimethylsilyl)benzo[b]-thiophene-7-sulfonamide, 1,1-dioxide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 15

Wettable Powder

| | |
|---|---|
| N—[(4,6-dimethoxypyrimidin-2-yl)aminocarbonyl]-2,3-dihydro-6-(methoxymethyl)-2-methylbenzo[b]-thiophene-7-sulfonamide, 1,1-dioxide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 16

Low Strength Granule

| | |
|---|---|
| N—[(4,6-dimethoxypyrimidin-2-yl)aminocarbonyl]-2,3-dihydro-2-methyl-6-(trimethylsilyl)benzo[b]-thiophene-7-sulfonamide, 1,1-dioxide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 17

Aqueous Suspension

| | |
|---|---|
| N—[(4,6-dimethoxypyrimidin-2-yl)aminocarbonyl]-2,3-dihydro-2-methyl-6-(trimethylsilyl)benzo[b]-thiophene-7-sulfonamide, 1,1-dioxide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 18

Solution

| | |
|---|---|
| N—[(4,6-dimethoxypyrimidin-2-yl)aminocarbonyl]-2,3-dihydro-6-(methoxymethyl)-2-methylbenzo[b]thiophene-7-sulfonamide, 1,1-dioxide, ammonium salt | 5% |
| water | 95% |

The salt is added directly to the water with stirring to produce the solution, which may then be packaged for use.

EXAMPLE 19

Low Strength Granule

| | |
|---|---|
| N—[(4,6-dimethoxypyrimidin-2-yl)aminocarbonyl]-2,3-dihydro-2-methyl-6-(trimethylsilyl)benzo[b]-thiophene-7-sulfonamide, 1,1-dioxide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 20

Granule

| | |
|---|---|
| N—[(4,6-dimethoxypyrimidin-2-yl)aminocarbonyl]-2,3-dihydro-6-(methoxymethyl)-2-methylbenzo[b]-thiopene-7-sulfonamide, 1,1-dioxide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 21

High Strength Concentrate

| | |
|---|---|
| N—[(4,6-dimethoxypyrimidin-2-yl)aminocarbonyl]-2,3-dihydro-6-(methoxymethyl)-2-methylbenzo[b]-thiophene-7-sulfonamide, 1,1-dioxide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 22

Wettable Powder

| | |
|---|---|
| N—[(4,6-dimethoxypyrimidin-2-yl)aminocarbonyl]-2,3-dihydro-2-methyl-6-(trimethylsilyl)benzo[b]-thiophene-7-sulfonamide, 1,1-dioxide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 23

Wettable Powder

| | |
|---|---|
| N—[(4,6-dimethoxypyrimidin-2-yl)aminocarbonyl]-2,3-dihydro-2-methyl-6-(trimethylsilyl)benzo[b]-thiophene-7-sulfonamide, 1,1-dioxide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 24

Oil Suspension

| | |
|---|---|
| N—[(4,6-dimethoxypyrimidin-2-yl)aminocarbonyl]-2,3-dihydro-6-(methoxymethyl)-2-methylbenzo[b]-thiophene-7-sulfonamide, 1,1-dioxide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 25

Dust

| | |
|---|---|
| N—[(4,6-dimethoxypyrimidin-2-yl)aminocarbonyl]-2,3-dihydro-2-methyl-6-(trimethylsilyl)benzo[b]-thiophene-7-sulfonamide, 1,1-dioxide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 26

Emulsifiable Concentrate

| | |
|---|---|
| N—[(4,6-dimethoxypyrimidin-2-yl)aminocarbonyl]-2,3-dihydro-6-(methoxymethyl)-2-methylbenzo[b]-thiophene-7-sulfonamide, 1,1-dioxide | 10% |
| chlorobenzene | 84% |
| sorbitan monostearate and polyoxyethylene condensates thereof | 6% |

The ingredients are combined and stirred to produce a solution which can be emulsified in water for application.

Utility

Test results indicate that the compounds of the present invention are highly active preemergent or postemergent herbicides or plant growth regulants. Many of them have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as wheat, barley and soybeans. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, for plant growth modification or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

| Compound | $R_4$ | X | Y | Z |
|---|---|---|---|---|
| 1 | $CH_2OCH_3$ | $OCH_3$ | $CH_3$ | CH |
| 2 | $CH_2OCH_3$ | $OCH_3$ | $OCH_3$ | CH |
| 3 | $CH_2OCH_3$ | Cl | $OCH_3$ | CH |
| 4 | $CH_2OCH_3$ | $OCH_3$ | $CH_3$ | N |
| 5 | $Si(CH_3)_3$ | $OCH_3$ | $OCH_3$ | CH |
| 6 | $Si(CH_3)_3$ | Cl | $OCH_3$ | CH |
| 7 | $N(CH_3)_2$ | $CH_3$ | $CH_3$ | CH |
| 8 | $N(CH_3)_2$ | $CH_3$ | $OCH_3$ | CH |
| 9 | $N(CH_3)_2$ | $OCH_3$ | $OCH_3$ | CH |
| 10 | $N(CH_3)_2$ | Cl | $OCH_3$ | CH |
| 11 | $N(CH_3)_2$ | $CH_3$ | $OCH_3$ | N |
| 12 | $CH_2OH$ | $OCH_3$ | $OCH_3$ | CH |
| 13 | $CH_2OH$ | Cl | $OCH_3$ | CH |
| 14 | $CH_2CN$ | $CH_3$ | $OCH_3$ | CH |
| 15 | $CH_2CN$ | Cl | $OCH_3$ | CH |
| 16 | $CH_2CN$ | $OCH_3$ | $OCH_3$ | CH |

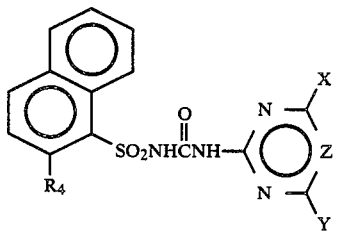

| 17 | $CH_2OCH_3$ | $CH_3$ | $CH_3$ | CH |
| 18 | $CH_2OCH_3$ | $CH_3$ | $OCH_3$ | CH |
| 19 | $CH_2OCH_3$ | $OCH_3$ | $OCH_3$ | CH |
| 20 | $CH_2OCH_3$ | $CH_3$ | $OCH_3$ | N |
| 21 | $CH_2OCH_3$ | $OCH_3$ | $OCH_3$ | N |

| Compound | $R_4$ | X | Y | Z |
|---|---|---|---|---|
| 22 | $N(CH_3)_2$ | $CH_3$ | $OCH_3$ | CH |
| 23 | $N(CH_3)_2$ | $OCH_3$ | $OCH_3$ | CH |
| 24 | $N(CH_3)_2$ | $CH_3$ | $OCH_3$ | N |
| 25 | $N(CH_3)_2$ | $OCH_3$ | $OCH_3$ | N |
| 26 | $N(CH_3)_2$ | $OCH_3$ | $OCH_3$ | CH |
| 27 | $N(CH_3)_2$ | $OCH_3$ | $CH_3$ | CH |
| 28 | $N(CH_3)_2$ | $CH_3$ | $CH_3$ | CH |
| 29 | $N(CH_3)_2$ | $OCH_3$ | $OCH_3$ | N |
| 30 | $N(CH_3)_2$ | Cl | $OCH_3$ | CH |

TEST A

Seeds of crabgrass (Digitaria spp.), barnyard-grass (Echinochloa crusgalli), wild oats (Avena fatua), cheatgrass (Bromus secalinus), velvetleaf (Abutilon theophrasti), morningglory (Ipomoea spp.), cocklebur (Xanthium pensylvanicum), sorghum, corn, soybean, sugarbeet, cotton, rice, wheat and purple nutsedge (Cyperus rotundus) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;
X=axillary stimulation;
S=albinism; and
6Y=abscised buds or flowers.

TABLE A

| | Cmpd. 1 | Cmpd. 2 | Cmpd. 3 | Cmpd. 4 | Cmpd. 5 | Cmpd. 6 | Compound 7 | | Compound 8 | | Compound 9 | | Compound 10 | | Compound 11 | | Compound 12 | |
|---|---|---|---|---|---|---|---|---|---|---|---|---|---|---|---|---|---|---|
| Rate kg/ha | 0.05 | 0.05 | 0.05 | 0.05 | 0.05 | 0.05 | 0.05 | 0.01 | 0.05 | 0.01 | 0.05 | 0.01 | 0.05 | 0.01 | 0.05 | 0.01 | 0.05 | 0.01 |
| | | | | | | | POSTEMERGENCE | | | | | | | | | | | |
| Morningglory | 10C | 10C | 10C | 9C | 10C | 10C | 5C,9G | 2H | 3C,9G | 9C | 4C,9G | 2C,7G | 3C,7H | 5G | 10C | 10C |
| Cocklebur | 10C | 10C | 10C | 4C,9H | 9C | 5C,9G | 4C,9G | 3H | 5C,9H | 9C | 9C | 3C,9H | 3C,9G | 1C | 10C | 4C,9G |
| Velvetleaf | 9C | 9C | 9C | 4C,8H | 10C | 5C,9G | 3C,7G | 0 | 3C,6G | 4C,8G | 5C,9G | 2H | 0 | 10C | 10C |
| Nutsedge | 9C | 6C,9G | 5C,9G | 5G | 4C,9G | 2G | 0 | 0 | 0 | 5G | 4G | 0 | 3G | 0 | 9C | 2C,8G |
| Crabgrass | 4C,9G | 6C,9G | 9G | 4G | 9G | 5G | 3G | 2G | 5G | 4C,9G | 0 | 0 | 4G | 0 | 9C | 4C,9G |
| Giant Foxtail | | | | | | | 2C,5G | 2G | 3G | 7H | 3C,6G | 2G | 5H | 0 | 9C | 5C,9G |
| Barnyardgrass | 5C,9G | 6C,9H | 6C,9H | 5C,9G | 9C | 9H | 3C,8H | 3H | 3G | 7H | 3C,7H | 3H | 5G | 0 | 9C | 9C |
| Cheatgrass | 5C,9G | 6C,9G | 4C,9G | 5C,9G | 3G | 3G | 7G | 5G | 7H | 4G | 4G | 2G | 5G | 8G | 4C,9G | 4C,9G |
| Wild Oats | 3C,9G | 5C,9G | 3C,9G | 5C,9G | 4C,9H | 3G | 3C,8G | 2C,7G | 3C,9G | 9G | 4C,8G | 3H | 4C,9G | 8G | 9C | 2C,9G |
| Wheat | 2C,9G | 4C,9G | 5G | 9G | 9G | 0 | 9G | 8G | 3C,9H | 9C | 7G | 2G | 4C,9G | 0 | 10C | 9C |
| Corn | 4C,9G | 9C | 9G | 5C,9H | 3C,7H | 3C,7H | 3C,8H | 2H | 3C,9H | 5G | 8G | 2G | 9G | 0 | 10C | 10C |
| Barley | | | | | | | 4C,9G | 5G | 5G | 9G | 4C,9G | 3H | 5G | 0 | 9C | 9C |
| Soybean | 3C,9G | 5C,9G | 2H,5G | 1H,3G | 1H | 1H | 4C,9G | 1H | 4C,9G | 9C | 9C | 2G | 4C,9G | 5G | 9C | 5C,9G |
| Rice | 5C,9G | 5C | 9C | 9C | 5C,9G | 5C,9G | 3C,8G | 5G | 3C,8G | 9C | 5C,9G | 4G | 3C,5G | 2C | 9C | 9C |
| Sorghum | 10E | 9C | 9C | 9C | 9G | 9G | 4C,8G | 2C,7G | 4C,8G | 5C,9G | 3C,9G | 2C,7G | 3C,8G | 2C,2H | 10C | 9C |
| Sugar beet | 9C | 9C | 9C | 9C | 6G | 6G | 5C,9H | 3C,8G | 2C,5G | 4C,8G | 5C,9G | 3C,8G | 3C,8G | 0 | 10C | 10C |
| Cotton | 9C | 9C | 9C | 4C,9H | 5C,9G | 5C,9G | 5H | 2G | 2C,5G | 4C,9G | 5C,9G | 5G | 5G | 0 | 10C | 4C,9H |
| Bushbean | | | | | | | | | | | | | | | | |
| Cassia | | | | | | | | | | | | | | | | |

| | Cmpd. 1 | Cmpd. 2 | Cmpd. 3 | Cmpd. 4 | Cmpd. 5 | Cmpd. 6 | Compound 7 | | Compound 8 | | Compound 9 | | Compound 10 | | Compound 11 | | Compound 12 | |
|---|---|---|---|---|---|---|---|---|---|---|---|---|---|---|---|---|---|---|
| | | | | | | | PREEMERGENCE | | | | | | | | | | | |
| Morningglory | 9G | 9G | 9G | 9G | 6G | 6G | 0 | 2G | 2G | 1H | 0 | 0 | 9G | 0 | 6G | 0 |
| Cocklebur | 8H | 9H | 7H | 7H | | | 0 | — | 3C,5G | 1H | 2H | 0 | — | 0 | 4G | 2H |
| Velvetleaf | 5C,9G | 9C | 5C,9G | 5G | 8G | 8G | 0 | 0 | 5H | 0 | 0 | 0 | 4G | 0 | 4G | 0 |
| Nutsedge | 10E | 10E | 10E | 6G | 0 | 0 | 0 | 0 | 4G | 0 | 0 | 0 | 0 | 0 | 8G | 5G |
| Crabgrass | 4C,8G | 2C,8G | 5G | 0 | 2G | 2G | 0 | 0 | 0 | 0 | 0 | 0 | 0 | 0 | 7G | 4G |
| Giant Foxtail | | | | | | | 0 | 0 | 3G | 0 | 0 | 0 | 0 | 0 | 6G | 0 |
| Barnyardgrass | 5C,9H | 9H | 9H | 5G | 5G | 5G | 3G | 0 | 5H | 0 | 2H | 0 | 0 | 0 | 6H | 0 |
| Cheatgrass | 9H | 3C,8H | 8G | 8G | 9H | 9H | 5H | 0 | 8H | 0 | 0 | 0 | 0 | 2G | 6G | 2G |
| Wild Oats | 5C,9G | 4C,9G | 5C,9G | 5C,9G | 3G | 3G | 7G | 0 | 7G | 0 | 0 | 0 | 0 | 0 | 5G | 0 |
| Wheat | 5C,9H | 10E | 8G | 9G | 4G | 4G | 2C,3G | 0 | 1C | 0 | 2G | 2G | 0 | 0 | 7G | 0 |
| Corn | 5C,9H | 4C,9G | 2C,2H | 2U,9G | 2C,7G | 2C,7G | 8G | 0 | 7G | 0 | 2G | 0 | 3G | 0 | 2C,7G | 2G |
| Barley | | | | | | | 3C,7G | 0 | 3C,8G | 0 | 0 | 0 | 0 | 0 | 2C,3G | 0 |
| Soybean | 3C,5G | 3G | 3G | 0 | 1C,1H | 1C,1H | 2G | 0 | 2G | 2C,2H | 0 | 0 | 0 | 0 | 2C,9G | 0 |
| Rice | 10E | 10E | 10E | 10E | 9H | 9H | 4H | 2H | 4H | 9H | 0 | 0 | 8H | 0 | 3C,9H | 0 |
| Sorghum | 5C,9H | 5C,9H | 5C,9H | 9H | 9H | 9H | 2G | 3G | 9H | 9H | 7H | 0 | 5G | 0 | 3G | 3G |
| Sugar beet | 4C,9G | 4C,9G | 4C,9G | 5C,9G | 7G | 7G | 2G | 3C,3G | 3H | 8G | 2C,5G | 0 | 7H | 0 | 3G |
| Cotton | 4C,9G | 8G | 9C | 7G | 0 | 0 | 2G | 3G | 5H | 9G | 5H | 0 | 3G | 2G | 2G |
| Bushbean | | | | | | | 0 | 0 | 5C,9G | 3G | 2G | 0 | 5G | | |
| Cassia | | | | | | | | | | | | | | | | |

| | Compound 13 | | Compound 14 | | Compound 15 | | Compound 16 | | Cmpd. 17 | | Cmpd. 18 | | Cmpd. 19 | | Cmpd. 20 | Cmpd. 21 | Compound 22 | | Compound 23 | |
|---|---|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.05 | 0.05 | 0.01 | 0.05 | 0.01 |
| | | | | | | | POSTEMERGENCE | | | | | | | | | | | | | |
| Morningglory | 9C | 8G | 10C | 4C,8G | 2C,5G | 10C | 9C | 0 | 1C,2H | 2G | 8G | 4C,9G | 0 | 4C,9G | 10C | 3C,7G | 3C,7G |
| Cocklebur | 7H | 1H | 10C | 9C | 7H | 10C | 10C | 2C,9G | 3C,9H | 3C,5G | 7H | 9C | 2H | 10C | 4C,8G | 2C,3G | 5C,9H | 2C,9H |
| Velvetleaf | 9C | 7G | 10C | 4C,8H | 6G | 10C | 9C | 0 | — | 5H | 6H | 9C | 0 | 10C | 9C | 9C | 9C | 9C |
| Nutsedge | 9G | 5G | 9G | 2C,5G | 2G | 9G | 4C,9G | 1C,9G | 2C,8G | 4G | 9G | 2C,8G | 5G | 2C,9G | 2C,9G | 8G | 4C,9G | 3C,9G |
| Crabgrass | 9C | 5G | 9C | 3C,8G | 2G | 9C | 3C,8G | 0 | 4G | 2G | 5H | 7H | 4G | 2C,8G | 2G | 2C,9G | 9C | 9C |
| Giant Foxtail | 3C,9G | 2G | 6C,9G | 3C,8G | 8G | 9C | 5C,9G | 0 | — | — | 9G | 2G | — | 5C,9G | 2G | 5C,9G | 5C,9G |

TABLE A-continued

| | | | | | | | | | | | | | | | |
|---|---|---|---|---|---|---|---|---|---|---|---|---|---|---|---|
| Barnyardgrass | 9C | 9H | 5C,9G | 2C,9H | 8H | 9C | 9C | 0 | 2C,8H | 3C,9H | 2C,7H | 3G | 4C,9G | 2C,8H | 4C,9H | 3C,9H |
| Cheatgrass | 6G | 0 | 7G | 2G | 0 | 9G | 2C,8G | 3C,8G | 0 | 1C | 1C,3G | 0 | 2C,8G | 6G | 5C,9G | 3C,9G |
| Wild Oats | 0 | 0 | 3C,7G | 3C,8G | 2C,6G | 6C,9G | 5C,9G | 5C,9G | 2G | 1C | 2G | 0 | 3C,5G | 2C,6G | 4C,9G | 3C,7G |
| Wheat | 9C | 4C,9G | 4C,9G | 2C,9G | 7G | 5C,9G | 10C | 5C,9G | 0 | 1C,7H | 2C,4G | 0 | 3C,8G | 4C,8G | 9C | 9G |
| Corn | 2C,8G | 2C,5G | 10C | 5C,9H | 2C,9H | 9C | 3C,8G | 2C,9G | 1C,3G | | | | 5C,9G | 2C,7G | 4C,9G | 4C,9G |
| Barley | 2C,4H | | 6C,9G | 2C,9G | 2C,7G | 10C | 9C | 3C,8G | 2C,8G | 5C,9G | 5C,9G | 5C,9G | 4C,9G | 3C,9G | 4C,9H | 4C,9G |
| Soybean | 5C,9G | 5C,9G | 4C,8H | 0 | 0 | 4C,8H | 3H,7G | 4C,9G | 2C,7G | 3G | 4C,7G | 2C,8G | 3C,9G | 5C,9G | 6C,9G | 5C,9G |
| Rice | 9C | 3C,9G | 9C | 5C,9G | 7G | 9C | 9C | 2C,7G | 5G | 2C,9H | 9G | 2C,9H | 4C,9G | 3C,9G | 4C,9H | 4C,9G |
| Sorghum | 9C | 3C,5G | 9C | 3C,9G | 2C,9H | 9C | 9C | 2C,9H | 2C,9G | 2C,8G | 5C,9G | 5C,9G | 4C,9G | 7G | 6C,9G | 4C,9G |
| Sugar beet | 9C | 2C,7G | 10C | 9C | 3G | 10C | 10C | 3G | 3G | 4C,9G | 5C,9G | 4C,9G | 10C | 2C,4G | 10C | 9C |
| Cotton | 3C,8G | | 3C,9H | 3C,7G | | 3C,9H | 6G | 4C,9G | 4C,9G,6Y | 6C,9G,6Y | 6C,9G,6Y | 5C,9G,6Y | 4C,8G,6Y | | | 4C,9H |
| Bushbean | | | | | | | | | 4G | 4C,8G | 4C,8G | 1C,4G | 4G | | | |
| Cassia | | | | | | | | | 2C,5H | | | | | | | |

PREEMERGENCE

| | | | | | | | | | | | | | | | |
|---|---|---|---|---|---|---|---|---|---|---|---|---|---|---|---|
| Morningglory | 6G | 0 | 3H | 2C,3H | 0 | 9G | 9H | 8G | 9C | 9C | 9G | 9C | 5G | 2G | — | |
| Cocklebur | 0 | 0 | 4G | 2H | 0 | 9H | 9H | 9G | | 9H | | | 1C,4G | 2H | 5H | |
| Velvetleaf | 0 | 2H | 2C,4G | 4G | 0 | 9C | | | 10E | | 10E | — | 2C,4G | 0 | 2G | |
| Nutsedge | 2G | 0 | 5G | 0 | 0 | 10E | 3G | 3G | 5G | 10E | 9G | 8G | 2C | 0 | 0 | |
| Crabgrass | 2G | 0 | 4C,8G | 9H | 0 | 6G | 3G | 5G | | 3G,1C | 0 | 0 | 0 | 5G | 5G | |
| Giant Foxtail | 0 | 0 | 6G | 3G | 0 | 5G | 3C,8H | | | | | | 0 | 4G | 4G | |
| Barnyardgrass | 0 | 0 | 3G | 5G | 0 | 3C,5G | 3C,8H | 4C,8H | | 2C,7H | 2C,7H | 2H | 8G | 3G | 3G | |
| Cheatgrass | 0 | 0 | 7H | 3G | 0 | 3C,9H | 7G | | | | | | 2C,4G | 7G | 7G | |
| Wild Oats | 0 | 0 | 5G | 5G | 0 | 5C,9H | 3C,8G | 2C,8G | | 1C | 1C,5G | | 1C,5G | 0 | 0 | |
| Wheat | 0 | 0 | 4G | 2G | 0 | 10E | 3C,9H | 6G | | 1C | 3G | 1C,6G | 2C,7G | 2G | 2G | |
| Corn | 5G | 0 | 3C,6G | 7G | 0 | 5C,9H | 4C,9H | 2C,7H | | 2C,8G | 2C,6G | 1C,7G | 0 | 0 | 0 | |
| Barley | 2G | 0 | 2C,6G | 3C,3G | 3C,3G | 5C,9G | 4C,8H | 2C,8G | | 2C,3H | 2C,7H | 3C,4H | 2C,4G | 2C,4G | 0 | |
| Soybean | 3G | 0 | 0 | 5G | 0 | 6G | 4C,8H | 4C,8H | | 2C,8G | 2C,7G | 4C,8H | 2C,8G | 2C,7G | 0 | |
| Rice | 3G | 3G | 3C,8H | 0 | 0 | 10E | 4C,6G | 3C,9G | | 2C,9G | 2C,8H | 2C,8H | 2C,9H | 0 | 3G | |
| Sorghum | 7G | 3G | 4C,9H | 8G | 5G | 5C,9H | 2C,7G | 2C,9G | | 2C,9G | 4C,9G | 2C,9G | 2H | 0 | 0 | |
| Sugar beet | 2C,8G | 6G | 7G | 3C,9H | 0 | 9G | 8G | | | | | | 7G | 0 | 0 | |
| Cotton | 7H | 0 | 1C | 9G | | 9G | | 9C | 8G | 2C,8G | 7G | 8G | | | | |
| Bushbean | 0 | | | | | | | | | | | | | | | |
| Cassia | | | | | | | | | | | | | | | | |

| | Cmpd. 24 | Cmpd. 25 | Compound 26 | | Compound 27 | | Compound 28 | | Compound 29 | | Compound 30 | |
|---|---|---|---|---|---|---|---|---|---|---|---|---|
| Rate kg/ha | 0.05 | 0.05 | 0.05 | 0.01 | 0.05 | 0.01 | 0.05 | 0.01 | 0.05 | 0.01 | 0.05 | 0.01 |

POSTEMERGENCE

| | | | | | | | | | | | | |
|---|---|---|---|---|---|---|---|---|---|---|---|---|
| Morningglory | 10C | 10C | 5C,9G | 3C,5G | 3C,7G | 2C,4G | 2C,3G | 2C,4G | 2C,8G | 1C | 2G | 2G |
| Cocklebur | 10C | 10C | 5C,9G | 3C,9G | 3C,8H | 2H,5G | 2G | 2G | 4C,9H | 8H | 4C,9H | 2H |
| Velvetleaf | 5C,8G | 2C,7G | 10C | 3C,7G | 4C,9G | 2C,5G | 5G | 5G | 2C,8G | 8G | 2C,8G | 3G |
| Nutsedge | 2C,8G | 2C,9G | 2C,5G | 4C,9G | 2C,5G | 4G | 0 | 0 | 2C,8G | 3G | 3G | 3G |
| Crabgrass | 5C,9G | 3C,9G | 5C,9G | 5C,9G | 2C,8G | 5G | 4C,8G | 0 | 4C,8G | 3C,7G | 3C,9G | 5G |
| Giant Foxtail | 9C | 9C | 9C | 4C,9G | 2C,8G | 4G | 3G | 2G | 9C | 3C,7G | 5C,9G | 5G |
| Barnyardgrass | 4C,8G | 4C,9G | 4C,9G | 4C,9H | 4C,9H | 3C,7H | 2G | 7H | 9C | 4C,9H | 5C,9H | 9H |
| Cheatgrass | 2C,8G | 2C,8G | 2C,9G | 9C | 3C,8H | 7G | 7H | 2G | 9C | 9C | 9H | 9C |
| Wild Oats | 4C,7G | 3C,7G | 3C,9G | 4C,9G | 3C,7G | 7G | 2G | 2G | 7G | 4G | 0 | 0 |
| Wheat | 1C,5G | 1C,7G | 4C,9G | 9C | 7G | 3G | 3C,9H | 3C,9H | 6G | 7G | 3G | 3G |
| Corn | 8C | 4C,9G | 3C,9G | 9C | 4C,9H | 3C,8H | 0 | 0 | 9C | 4C,9G | 3C,9H | 3C,9H |
| Barley | 5C,9G | 5C,9G | 3C,8G | 4C,9G | 2C,5G | 3G | 2G | 6G | 4C,9G | 4C,9G | 9G | 4G |
| Soybean | 6C,9G | 5C,8G | 4C,9G | 4C,9G | 3H,5G | 3C,8G | 6G | 6G | 9C | 9C | 3H | 0 |
| Rice | 9C | 2C,9G | 9C | 4C,9G | 4C,9G | 2C,8G | 2C,8G | 2C,8G | 4C,9G | 4C,9G | 4C,9G | 8G |
| Sorghum | 3C,9G | 2C,9G | 3C,9G | 4C,9G | 3C,7G | 3C,5G | 2C,9G | 3C,9H | 3C,5G | 5C,9G | 4C,9H | 2C,9G |
| Sugar beet | 10C | 3C,5G | 5C,9G | 7H | 7G | 3C,6G | 8G | 2H | 2H | 2H | 4C,8G | 2C,5G |

TABLE A-continued

| | 10C | 2C,9G | 9C | 6G | 3C,8G | 3C,7G | 4G | 0 | 8G | 2G | 3C,8G | 7G |
|---|---|---|---|---|---|---|---|---|---|---|---|---|
| Cotton | 2C,5G | 5G | 8G | 5G | 2C,5G | 0 | 3G | 0 | 7G | 0 | 0 | 0 |
| Bushbean | 2C,5G | 2C,4G | 8H | — | 2G | 0 | — | — | 7G | 0 | 0 | 0 |
| Cassia | 3C,4G | 0 | 9G | 8G | 4C,9G | 6G | 4G | 2H | 4C,9G | 7H | 5G | — |
| | | | | | PREEMERGENCE | | | | | | | |
| Morningglory | 8G | 2C,8G | 9G | 6G | 2G | 0 | 0 | 0 | 4G | 0 | 8G | 10E |
| Cocklebur | 2C,8G | 2C | 5C,9G | 8G | 9C | 0 | — | 0 | 6G | 0 | 2G | 0 |
| Velvetleaf | 3G | 0 | 9C | 3C,7H | 9H | 5G | 2C | 0 | 9H | 0 | 4G | 0 |
| Nutsedge | 2C,4G | 0 | 9H | 7G | 3C,9H | 6G | 3G | 0 | 9H | 2G | 2C,7G | 2G |
| Crabgrass | 2C,7H | 0 | 8G | 3C,7G | 3C,8G | 6G | 3G | 0 | 8G | 2G | 5G | 0 |
| Giant Foxtail | 2C,2G | 0 | 9G | 2C,7G | 3C,9G | 8G | 3G | 0 | 8G | 2C,6G | 2C,4G | 2G |
| Barnyardgrass | 2C,7G | 0 | 9G | 7G | 9H | 7G | 2C,5G | 0 | 8G | 6G | 0 | 0 |
| Cheatgrass | 2C,5G | 0 | 9G | 2C,5G | 2C,9G | 2C,7G | 3G | 0 | 8G | 6G | 2C,7G | 4G |
| Wild Oats | 4G | 0 | 9G | 8G | 2C,9G | 2C,2G | 3G | 0 | 9G | 4G | 9G | 2G |
| Wheat | 2C,5G | 0 | 2C,7G | 0 | 3C,5G | 2C,2G | 0 | 0 | 5G | 0 | 0 | 0 |
| Corn | 3C,8G | 2C,5G | 3C,9H | 8G | 9H | 3C,8H | 2C,6G | 0 | 3C,9H | 3C,8G | 3C,8H | 5G |
| Barley | 3C,9H | 1C,4G | 9G | 3G | 2C,8G | 2C | 2G | 0 | 2C,9G | 3C,8G | 3C,8G | 0 |
| Soybean | 4C,8G | 4G | 7G | 5G | 7G | 5G | 5G | 2G | 6G | 4G | 8G | 0 |
| Rice | 5G | 1C,3G | 6G | 2G | 6G | 2G | 0 | 0 | 8G | 2G | 0 | 0 |
| Sorghum | | | | | | | | | | | | |
| Sugar beet | | | | | | | | | | | | |
| Cotton | | | | | | | | | | | | |
| Bushbean | | | | | | | | | | | | |
| Cassia | | | | | | | | | | | | |

What is claimed is:

1. A compound of the formula

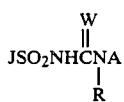   I wherein

J is

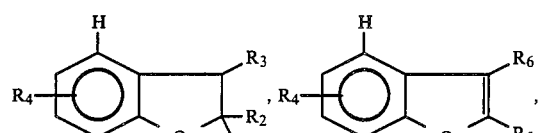

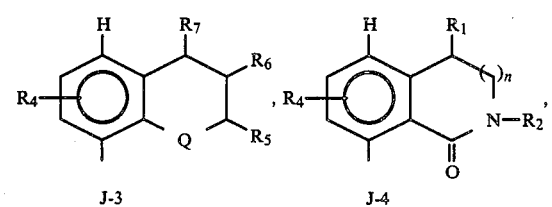

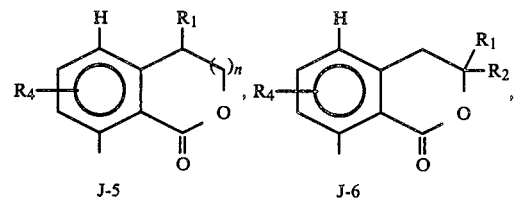

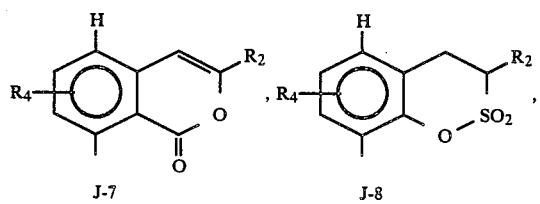

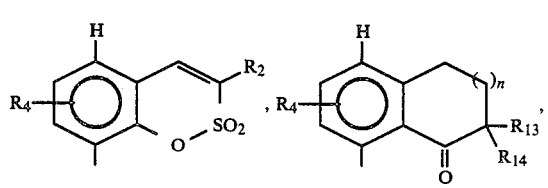

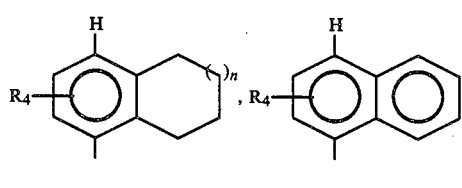

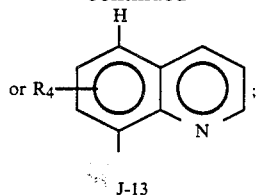

n is 0 or 1;
W is O or S;
Q is O, S, SO or $SO_2$;
R is H or $CH_3$;
$R_1$ is H or $CH_3$;
$R_2$ is H or $C_1-C_3$ alkyl;
$R_3$ is H or $CH_3$;
$R_4$ is $C_3-C_6$ cycloalkyl, $C_5-C_6$ cycloalkenyl,

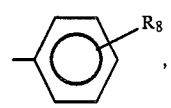

$Si(CH_3)_2(C_1-C_4$ alkyl), $Si(CH_3)_2(C_2-C_4$ alkenyl), $Si(CH_3)_2(C_1-C_3$ alkoxy),

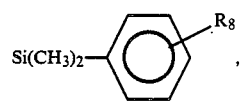

$P(O)(CH_3)_2$, $P(O)(OCH_3)_2$, CN, $C_1-C_4$ alkylcarbonyl, $C_3-C_4$ cycloalkylcarbonyl, $NR_9R_{10}$ or $C_1-C_2$ alkyl substituted with $C_3-C_5$ cycloalkyl, $C_1-C_3$ alkoxy, $C_1-C_3$ haloalkoxy, $C_2-C_3$ alkenyloxy, $C_2-C_3$ haloalkenyloxy, $C_1-C_3$ alkylthio, $C_1-C_3$ haloalkylthio, $C_1-C_3$ alkylsulfinyl, $C_1-C_3$ alkylsulfonyl, $C_1-C_3$ haloalkylsulfinyl, $C_1-C_3$ haloalkylsulfonyl, $Si(CH_3)_2(C_1-C_4$ alkyl), $NO_2$, CN, $C_1-C_2$ alkylcarbonyl, OH, $NR_9R_{10}$, $CO_2(C_1-C_3$ alkyl), SCN, $P(O)(OCH_3)_2$ or $SO_2NR_{11}R_{12}$;

$R_5$ is H or $C_1-C_2$ alkyl;
$R_6$ is H or $CH_3$;
$R_7$ is H or $CH_3$;
$R_8$ is H, F, Cl, Br, $CH_3$, $OCH_3$ or $SCH_3$;
$R_9$ is H or $C_1-C_3$ alkyl;
$R_{10}$ is H or $C_1-C_3$ alkyl; or
$R_9$ and $R_{10}$ may be taken together to form $(CH_2)_4$, $(CH_2)_5$ or $CH_2CH_2OCH_2CH_2$;
$R_{11}$ and $R_{12}$ are independently H or $C_1-C_3$ alkyl;
$R_{13}$ is H, $C_1-C_3$ alkyl, Cl or Br;
$R_{14}$ is H, $CH_3$, Cl or Br;
A is

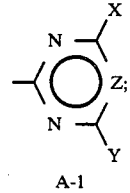

X is H, $C_1-C_4$ alkyl, $C_1-C_4$ alkoxy, $C_1-C_4$ haloalkoxy, $C_1-C_4$ haloalkyl, $C_1-C_4$ haloalkylthio, $C_1-C_4$ alkylthio, halogen, $C_2-C_5$ alkoxyalkyl, $C_2-C_5$ alkoxyalkoxy, amino, $C_1$-$C_3$ alkylamino, di($C_1$-$C_3$ alkyl)amino or $C_3$-$C_5$ cycloalkyl;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_2$-$C_5$ alkylsulfinylalkyl, $C_2$-$C_5$ alkylsulfonylalkyl, $C_1$-$C_4$ haloalkyl, $C_2$-$C_4$ alkynyl, azido, cyano,

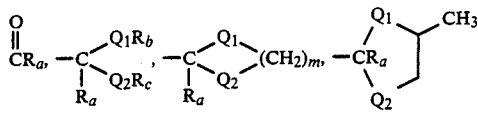

or $N(OCH_3)CH_3$;

m is 2 or 3;

$Q_1$ and $Q_2$ are independently O or S;

$R_a$ is H or $C_1$-$C_3$ alkyl;

$R_b$ and $R_c$ are independently $C_1$-$C_3$ alkyl;

Z is CH, $CCH_3$, $CC_2H_5$, CCl or CBr;

and their agriculturally suitable salts; provided that
(a) when X is Cl, F, Br or I, then Z is CH and Y is $OCH_3$, $OC_2H_5$, $N(OCH_3)CH_3$, $NHCH_3$, $N(CH_3)_2$ or $OCF_2H$; and
(b) when X or Y is $C_1$ haloalkoxy, then Z is CH;
(c) when W is S, then R is H, Z is CH and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or

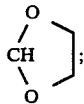

(d) when $R_1$ is $CH_3$, then n is O;
(e) when J is J-6, then $R_1$ is $R_2$ are not both H;
(f) when the total number of carbons of X and Y is greater than four, then the number of carbons of $R_4$ must be less than or equal to three;
(g) when J is J-12, then $R_4$ is other than $C_1$-$C_4$ alkylcarbonyl; and
(h) when J is J-9, then $R_4$ is other than CN.

2. The compounds of claim 1 wherein:
J is J-1, J-2, J-3, J-4, J-5 or J-6; and
$R_4$ is $C_3$-$C_6$ cycloalkyl, $C_5$-$C_6$ cycloalkenyl,

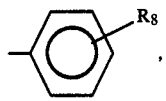

$Si(CH_3)_2(C_1$-$C_4$ alkyl), $Si(CH_3)_2(C_2$-$C_4$ alkenyl), $Si(CH_3)_2(C_1$-$C_3$ alkoxy),

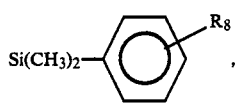

$P(O)(CH_3)_2$, $P(O)(OCH_3)_2$, CN, $NR_9R_{10}$ or $C_1$-$C_2$ alkyl substituted with $C_3$-$C_5$ cycloalkyl, $C_1$-$C_3$ alkoxy, $C_1$-$C_3$ haloalkoxy, $C_2$-$C_3$ alkenyloxy, $C_2$-$C_3$ haloalkenyloxy, $C_1$-$C_3$ alkylthio, $C_1$-$C_3$ haloalkylthio, $C_1$-$C_3$ alkylsulfinyl, $C_1$-$C_3$ alkylsulfonyl, $C_1$-$C_3$ haloalkylsulfinyl, $C_1$-$C_3$ haloalkylsulfonyl, $Si(CH_3)_2(C_1$-$C_4$ alkyl), $NO_2$, CN, $NR_9R_{10}$, $CO_2(C_1$-$C_3$ alkyl), SCN, $P(O)(OCH_3)_2$ or $SO_2NR_{11}R_{12}$.

3. The compounds of claim 1 where
$R_4$ is $C_3$-$C_6$ cycloalkyl, $C_5$-$C_6$ cycloalkenyl,

$Si(CH_3)_2(C_1$-$C_4$ alkyl), $Si(CH_3)_2(C_2$-$C_4$ alkenyl), $Si(CH_3)_2(C_1$-$CH_3$ alkoxy),

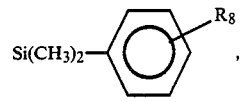

$P(O)(CH_3)_2$, $P(O)(OCH_3)_2$, $C_1$-$C_4$ alkylcarbonyl, $C_3$-$C_4$ cycloalkylcarbonyl, $NR_9R_{10}$ or $C_1$-$C_2$ alkyl substituted with $C_3$-$C_5$ cycloalkyl, $C_1$-$C_3$ alkoxy, $C_1$-$C_3$ haloalkoxy, $C_2$-$C_3$ alkenyloxy, $C_2$-$C_3$ haloalkenyloxy, $C_1$-$C_3$ alkylthio, $C_1$-$C_3$ haloalkylthio, $C_1$-$C_3$ alkylsulfinyl, $C_1$-$C_3$ alkylsulfonyl, $C_1$-$C_3$ haloalkylsulfinyl, $C_1$-$C_3$ haloalkylsulfonyl, $Si(CH_3)_2(C_1$-$C_4$ alkyl), $NO_2$, CN, $C_1$-$C_2$ alkylcarbonyl, OH, $NR_9R_{10}$, $CO_2(C_1$-$C_3$ alkyl), SCN, $P(O)(OCH_3)_2$ or $SO_2NR_{11}R_{12}$.

4. The compounds of claim 1 where
W is O;
R is H;
X is $C_1$-$C_2$ alkyl, $C_1$-$C_2$ alkoxy, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$; and
Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$, $CH_2SCH_2CH_3$, $OCH_2CH_2OCH_3$,

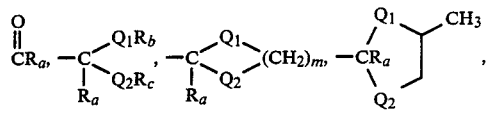

$OCF_2H$, $SCF_2H$, $C\equiv CH$ or $C\equiv CCH_3$; and
Z is CH; and
when $R_4$ is meta to the sulfonylurea bridge, then it is selected from $CH_2OCH_3$, $CH_2OCH_2CH_3$, $CH_2CH_2OCH_3$, $CH_2SCH_3$, $CH_2SCH_2CH_3$, $CH_2CH_2SCH_3$, $CH_2CN$, $NH_2$, $NHCH_3$, $N(CH_3)_2$ or $CH_2OH$.

5. The compounds of claim 4 where
$R_4$ is $C_3$-$C_6$ cycloalkyl, $C_5$-$C_6$ cycloalkenyl, cyclopropylmethyl, $Si(CH_3)_3$, $NH_2$, $NHCH_3$, $N(CH_3)_2$, $CH_2P(O)(OCH_3)_2$, CHO, $C(O)CH_3$, $CH_2CHO$, $CH_2CO_2CH_3$ or $C_1$-$C_2$ alkyl substituted with $C_1$-$C_2$ alkoxy, $C_1$-$C_2$ alkylthio, $C_1$-$C_2$ alkylsulfinyl, $C_1$-$C_2$ alkylsulfonyl, CN, OH or $SO_2N(CH_3)_2$.

6. The compounds of claim 5 wherein
$R_1$ is H;
$R_2$ is H or $CH_3$;
$R_3$ is H;
$R_5$ is H or $CH_3$;

$R_6$ is H;
$R_7$ is H;
$R_8$ is H;
$R_{13}$ is H, $CH_3$ or Cl;
$R_{14}$ is H, $CH_3$ or Cl; and
Q is O, S or $SO_2$.

7. The compounds of claim 6 where
$R_4$ is ortho to the sulfonylurea bridge and is selected from $Si(CH_3)_3$, $NH_2$, $NHCH_3$, $N(CH_3)_2$, $CH_2OCH_3$, $CH_2OCH_2CH_3$, $CH_2CH_2OCH_3$, $CH_2SCH_3$, $CH_2SCH_2CH_3$, $CH_2CH_2SCH_3$, $CH_2SO_2CH_3$, $CH_2SO_2CH_2CH_3$, $CH_2CH_2SO_2CH_3$, $CH_2CN$, $CH_2CH_2CN$ or $CH_2CH_2SO_2N(CH_3)_2$;
X is $CH_3$, $OCH_3$, $OCH_2CH_3$, Cl, $OCF_2H$ or $OCH_2CF_3$; and
Y is $CH_3$, $OCH_3$, $C_2H_5$, $CH_2OCH_3$, $NHCH_3$, $CH(OCH_3)_2$ or cyclopropyl.

8. The compound of claim 1 which is N-[(4,6-dimethoxypyrimidin-2-yl)aminocarbonyl]-2,3-dihydro-6-(methoxymethyl)-2-methylbenzo[b]thiophene-7-sulfonamide, 1,1-dioxide.

9. The compound of claim 1 which is N-[(4,6-dimethoxypyrimidin-2-yl)aminocarbonyl]-2,3-dihydro-2-methyl-6-(trimethylsilyl)benzo[b]thiophene-7-sulfonamide, 1,1-dioxide.

10. The compound of claim 1 which is N-[(4,6-dimethoxypyrimidin-2-yl)aminocarbonyl]-2,3-dihydro-6-(cyanomethyl)-2-methylbenzo[b]thiophene-7-sulfonamide, 1,1-dioxide.

11. An agriculturally suitable composition for controlling the growth of undesirable vegetation comprising an effective amount of a compound of claim 1 and at least one of a surfactant, solid or liquid diluent.

12. An agriculturally suitable composition for controlling the growth of undesirable vegetation comprising an effective amount of a compound of claim 2 and at least one of a surfactant, solid or liquid diluent.

13. An agriculturally suitable composition for controlling the growth of undesirable vegetation comprising an effective amount of a compound of claim 3 and at least one of a surfactant, solid or liquid diluent.

14. An agriculturally suitable composition for controlling the growth of undesirable vegetation comprising an effective amount of a compound of claim 4 and at least one of a surfactant, solid or liquid diluent.

15. An agriculturally suitable composition for controlling the growth of undesirable vegetation comprising an effective amount of a compound of claim 5 and at least one of a surfactant, solid or liquid diluent.

16. An agriculturally suitable composition for controlling the growth of undesirable vegetation comprising an effective amount of a compound of claim 6 and at least one of a surfactant, solid or liquid diluent.

17. An agriculturally suitable composition for controlling the growth of undesirable vegetation comprising an effective amount of a compound of claim 7 and at least one of a surfactant, solid or liquid diluent.

18. An agriculturally suitable composition for controlling the growth of undesirable vegetation comprising an effective amount of a compound of claim 8 and at least one of a surfactant, solid or liquid diluent.

19. An agriculturally suitable composition for controlling the growth of undesirable vegetation comprising an effective amount of a compound of claim 9 and at least one of a surfactant, solid or liquid diluent.

20. An agriculturally suitable composition for controlling the growth of undesirable vegetation comprising an effective amount of a compound of claim 10 and at least one of a surfactant, solid or liquid diluent.

21. A method for controlling the growth of undesired vegetation which comprises applying to the locus to be protected an effective amount of a compound of claim 1.

22. A method for controlling the growth of undesired vegetation which comprises applying to the locus to be protected an effective amount of a compound of claim 2.

23. A method for controlling the growth of undesired vegetation which comprises applying to the locus to be protected an effective amount of a compound of claim 3.

24. A method for controlling the growth of undesired vegetation which comprises applying to the locus to be protected an effective amount of a compound of claim 4.

25. A method for controlling the growth of undesired vegetation which comprises applying to the locus to be protected an effective amount of a compound of claim 5.

26. A method for controlling the growth of undesired vegetation which comprises applying to the locus to be protected an effective amount of a compound of claim 6.

27. A method for controlling the growth of undesired vegetation which comprises applying to the locus to be protected an effective amount of a compound of claim 7.

28. A method for controlling the growth of undesired vegetation which comprises applying to the locus to be protected an effective amount of a compound of claim 8.

29. A method for controlling the growth of undesired vegetation which comprises applying to the locus to be protected an effective amount of a compound of claim 9.

30. A method for controlling the growth of undesired vegetation which comprises applying to the locus to be protected an effective amount of a compound of claim 10.

* * * * *